United States Patent
Harper et al.

(10) Patent No.: US 11,975,220 B2
(45) Date of Patent: May 7, 2024

(54) SYSTEM FOR EMISSION-GUIDED HIGH-ENERGY PHOTON DELIVERY

(71) Applicant: RefleXion Medical, Inc., Hayward, CA (US)

(72) Inventors: Brent Harper, New Glarus, WI (US); David Larkin, Menlo Park, CA (US); David Nett, Danville, CA (US)

(73) Assignee: RefleXion Medical, Inc., Hayward, CA (US)

( * ) Notice: Subject to any disclaimer, the term of this patent is extended or adjusted under 35 U.S.C. 154(b) by 757 days.

(21) Appl. No.: 16/887,852

(22) Filed: May 29, 2020

(65) Prior Publication Data

US 2020/0368557 A1 Nov. 26, 2020

Related U.S. Application Data

(63) Continuation of application No. 15/814,222, filed on Nov. 15, 2017, now Pat. No. 10,695,586.

(Continued)

(51) Int. Cl.
*A61N 5/10* (2006.01)
*A61N 5/00* (2006.01)
*G21K 1/04* (2006.01)

(52) U.S. Cl.
CPC ......... *A61N 5/1081* (2013.01); *A61N 5/1045* (2013.01); *A61N 5/1049* (2013.01);
(Continued)

(58) Field of Classification Search
CPC .............. G21K 1/046; A61N 2005/005; A61N 2005/1094; A61N 2005/1091;
(Continued)

(56) References Cited

U.S. PATENT DOCUMENTS 3,418,475 A   12/1968   Hudgens
3,668,399 A    6/1972   Cahill et al.
(Continued)

FOREIGN PATENT DOCUMENTS

CN   2529663 Y    1/2003
CN   1681436 A   10/2005
(Continued)

OTHER PUBLICATIONS

Chang, J.Y. et al. (2008). "Image-guided radiation therapy for non-small cell lung cancer," *J. Thorac. Oncol.* 3(2):177-186.
(Continued)

*Primary Examiner* — Thaddeus B Cox
*Assistant Examiner* — Joshua Daryl D Lannu
(74) *Attorney, Agent, or Firm* — Cooley LLP

(57) ABSTRACT

Disclosed herein are radiation therapy systems and methods. These radiation therapy systems and methods are used for emission-guided radiation therapy, where gamma rays from markers or tracers that are localized to patient tumor regions are detected and used to direct radiation to the tumor. The radiation therapy systems described herein comprise a gantry comprising a rotatable ring coupled to a stationary frame via a rotating mechanism such that the rotatable ring rotates up to about 70 RPM, a radiation source (e.g., MV X-ray source) mounted on the rotatable ring, and one or more PET detectors mounted on the rotatable ring.

13 Claims, 47 Drawing Sheets

Related U.S. Application Data

(60) Provisional application No. 62/422,404, filed on Nov. 15, 2016.

(52) U.S. Cl.
CPC .... *A61N 2005/005* (2013.01); *A61N 2005/1052* (2013.01); *A61N 2005/1091* (2013.01); *A61N 2005/1094* (2013.01); *G21K 1/046* (2013.01)

(58) Field of Classification Search
CPC ......... A61N 5/1045; A61N 2005/1052; A61N 5/1049; A61N 5/1081
See application file for complete search history.

(56) References Cited

U.S. PATENT DOCUMENTS

| | | |
|---|---|---|
| 3,721,826 A | 3/1973 | Thomas, Jr. |
| 3,767,883 A * | 10/1973 | Staats .................. H05B 6/6482 327/531 |
| 3,773,106 A | 11/1973 | Levy |
| 3,779,135 A | 12/1973 | Sugimura |
| 3,794,840 A | 2/1974 | Scott |
| 3,844,341 A | 10/1974 | Bimshas, Jr. et al. |
| 3,869,615 A | 3/1975 | Hoover et al. |
| 3,906,233 A | 9/1975 | Vogel |
| 4,241,644 A | 12/1980 | Schertler |
| 4,246,488 A | 1/1981 | Hura |
| 4,361,902 A | 11/1982 | Brandt et al. |
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,628,499 A | 12/1986 | Hammett |
| 4,642,464 A | 2/1987 | Mullani |
| 4,647,779 A | 3/1987 | Wong |
| 4,677,299 A | 6/1987 | Wong |
| 4,760,589 A | 7/1988 | Siczek |
| 4,771,785 A | 9/1988 | Duer |
| 4,794,629 A | 12/1988 | Pastyr et al. |
| 4,868,844 A | 9/1989 | Nunan |
| 5,010,312 A | 4/1991 | Motykiewicz |
| 5,075,554 A | 12/1991 | Yunker et al. |
| 5,099,505 A | 3/1992 | Seppi et al. |
| 5,117,445 A | 5/1992 | Seppi et al. |
| 5,168,532 A | 12/1992 | Seppi et al. |
| 5,206,512 A | 4/1993 | Iwao |
| 5,207,223 A | 5/1993 | Adler |
| 5,262,649 A | 11/1993 | Antonuk et al. |
| 5,272,344 A | 12/1993 | Williams |
| 5,299,249 A | 3/1994 | Burke et al. |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,408,591 A | 4/1995 | Shih et al. |
| 5,418,827 A | 5/1995 | Deasy et al. |
| 5,442,675 A | 8/1995 | Swerdloff et al. |
| 5,548,627 A | 8/1996 | Swerdloff et al. |
| 5,577,026 A | 11/1996 | Gordon et al. |
| 5,596,619 A | 1/1997 | Carol |
| 5,661,773 A | 8/1997 | Swerdloff et al. |
| 5,668,371 A | 9/1997 | Deasy et al. |
| 5,724,400 A | 3/1998 | Swerdloff et al. |
| 5,748,703 A | 5/1998 | Cosman |
| 5,751,781 A | 5/1998 | Brown et al. |
| 5,757,881 A | 5/1998 | Hughes |
| 5,813,985 A | 9/1998 | Carroll |
| 5,818,902 A | 10/1998 | Yu |
| 5,851,182 A | 12/1998 | Sahadevan |
| 5,889,834 A | 3/1999 | Vilsmeier et al. |
| 5,917,883 A | 6/1999 | Khutoryansky et al. |
| 5,937,028 A | 8/1999 | Tybinkowski et al. |
| 5,946,425 A | 8/1999 | Bove, Jr. et al. |
| 6,023,494 A | 2/2000 | Senzig et al. |
| 6,052,436 A | 4/2000 | Hutter et al. |
| 6,094,760 A | 8/2000 | Nonaka et al. |
| 6,115,454 A | 9/2000 | Andrews et al. |
| 6,137,114 A | 10/2000 | Rohe et al. |
| 6,180,943 B1 | 1/2001 | Lange |
| 6,184,530 B1 | 2/2001 | Hines et al. |
| 6,188,748 B1 | 2/2001 | Pastyr et al. |
| 6,255,655 B1 | 7/2001 | McCroskey et al. |
| 6,260,005 B1 | 7/2001 | Yang et al. |
| 6,271,517 B1 | 8/2001 | Kroening, Jr. et al. |
| 6,281,505 B1 | 8/2001 | Hines et al. |
| 6,385,288 B1 | 5/2002 | Kanematsu |
| 6,396,902 B2 | 5/2002 | Tybinkowski et al. |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,455,856 B1 | 9/2002 | Gagnon |
| 6,459,769 B1 | 10/2002 | Cosman |
| 6,504,899 B2 | 1/2003 | Pugachev et al. |
| 6,560,311 B1 | 5/2003 | Shepard et al. |
| 6,618,467 B1 | 9/2003 | Ruchala et al. |
| 6,624,451 B2 | 9/2003 | Ashley et al. |
| 6,628,744 B1 | 9/2003 | Luhta et al. |
| 6,661,866 B1 | 12/2003 | Limkeman et al. |
| 6,661,870 B2 | 12/2003 | Kapatoes et al. |
| 6,696,694 B2 | 2/2004 | Pastyr et al. |
| 6,700,949 B2 | 3/2004 | Susami et al. |
| 6,714,076 B1 | 3/2004 | Kalb |
| 6,730,924 B1 | 5/2004 | Pastyr et al. |
| 6,735,277 B2 | 5/2004 | McNutt et al. |
| 6,778,636 B1 | 8/2004 | Andrews |
| 6,792,078 B2 | 9/2004 | Kato et al. |
| 6,794,653 B2 | 9/2004 | Wainer et al. |
| 6,810,103 B1 | 10/2004 | Tybinkowski et al. |
| 6,810,108 B2 | 10/2004 | Clark et al. |
| 6,831,961 B1 | 12/2004 | Tybinkowski et al. |
| 6,865,254 B2 | 3/2005 | Nafstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,110,808 B2 | 9/2006 | Adair |
| 7,129,495 B2 | 10/2006 | Williams et al. |
| 7,154,096 B2 | 12/2006 | Amano |
| 7,167,542 B2 | 1/2007 | Juschka et al. |
| 7,188,999 B2 | 3/2007 | Mihara et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,301,144 B2 | 11/2007 | Williams et al. |
| 7,310,410 B2 | 12/2007 | Sohal et al. |
| 7,331,713 B2 | 2/2008 | Moyers |
| 7,338,207 B2 | 3/2008 | Gregerson et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,405,404 B1 | 7/2008 | Shah |
| 7,412,029 B2 | 8/2008 | Myles |
| 7,433,503 B2 | 10/2008 | Cherek et al. |
| 7,439,509 B1 | 10/2008 | Grazioso et al. |
| 7,446,328 B2 | 11/2008 | Rigney et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,519,162 B2 | 4/2009 | Hoffmann |

(56) References Cited

U.S. PATENT DOCUMENTS

| | | |
|---|---|---|
| 7,545,911 B2 | 6/2009 | Rietzel et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,627,082 B2 | 12/2009 | Kojima et al. |
| 7,639,853 B2 | 12/2009 | Olivera et al. |
| 7,656,999 B2 | 2/2010 | Hui et al. |
| 7,657,304 B2 | 2/2010 | Mansfield et al. |
| 7,679,049 B2 | 3/2010 | Rietzel |
| 7,715,606 B2 | 5/2010 | Jeung et al. |
| 7,742,575 B2 | 6/2010 | Bourne |
| 7,755,054 B1 | 7/2010 | Shah et al. |
| 7,755,055 B2 | 7/2010 | Schilling |
| 7,755,057 B2 | 7/2010 | Kim |
| 7,778,691 B2 | 8/2010 | Zhang et al. |
| 7,783,007 B2 | 8/2010 | Echner |
| 7,792,252 B2 | 9/2010 | Bohn |
| 7,795,590 B2 | 9/2010 | Takahashi et al. |
| 7,800,070 B2 | 9/2010 | Weinberg et al. |
| 7,820,975 B2 | 10/2010 | Laurence et al. |
| 7,831,073 B2 | 11/2010 | Fu et al. |
| 7,839,972 B2 | 11/2010 | Ruchala et al. |
| 7,847,274 B2 | 12/2010 | Kornblau et al. |
| 7,869,562 B2 | 1/2011 | Khamene et al. |
| 7,885,371 B2 | 2/2011 | Thibault et al. |
| 7,939,808 B1 | 5/2011 | Shah et al. |
| 7,942,843 B2 | 5/2011 | Tune et al. |
| 7,952,079 B2 | 5/2011 | Neustadter et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,019,042 B2 | 9/2011 | Shukla et al. |
| 8,059,782 B2 | 11/2011 | Brown |
| 8,063,376 B2 | 11/2011 | Maniawski et al. |
| 8,090,074 B2 | 1/2012 | Filiberti et al. |
| 8,093,568 B2 | 1/2012 | Mackie et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,160,205 B2 | 4/2012 | Saracen et al. |
| 8,193,508 B2 | 6/2012 | Shchory et al. |
| 8,198,600 B2 | 6/2012 | Neustadter et al. |
| 8,232,535 B2 | 7/2012 | Olivera et al. |
| 8,239,002 B2 | 8/2012 | Neustadter et al. |
| 8,269,195 B2 | 9/2012 | Rigney et al. |
| 8,278,633 B2 | 10/2012 | Nord et al. |
| 8,280,002 B2 | 10/2012 | Bani-Hashemi et al. |
| 8,295,906 B2 | 10/2012 | Saunders et al. |
| 8,304,738 B2 | 11/2012 | Gagnon et al. |
| 8,306,185 B2 | 11/2012 | Bal et al. |
| 8,335,296 B2 | 12/2012 | Dehler et al. |
| 8,357,903 B2 | 1/2013 | Wang et al. |
| 8,384,049 B1 | 2/2013 | Broad |
| 8,395,127 B1 | 3/2013 | Frach et al. |
| 8,406,844 B2 | 3/2013 | Ruchala et al. |
| 8,406,851 B2 | 3/2013 | West et al. |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,520,800 B2 | 8/2013 | Wilfley et al. |
| 8,536,547 B2 | 9/2013 | Maurer, Jr. et al. |
| 8,537,373 B2 | 9/2013 | Humphrey |
| 8,581,196 B2 | 11/2013 | Yamaya et al. |
| 8,588,367 B2 | 11/2013 | Busch et al. |
| 8,617,422 B2 | 12/2013 | Koschan et al. |
| 8,641,592 B2 | 2/2014 | Yu |
| 8,664,610 B2 | 3/2014 | Chuang |
| 8,664,618 B2 | 3/2014 | Yao |
| 8,712,012 B2 | 4/2014 | O'Connor |
| 8,745,789 B2 | 6/2014 | Saracen et al. |
| 8,748,825 B2 | 6/2014 | Mazin |
| 8,767,917 B2 | 7/2014 | Ruchala et al. |
| 8,816,307 B2 | 8/2014 | Kuusela et al. |
| 8,873,710 B2 | 10/2014 | Ling et al. |
| 8,884,240 B1 | 11/2014 | Shah et al. |
| 8,992,404 B2 | 3/2015 | Graf et al. |
| 9,061,141 B2 | 6/2015 | Brunker et al. |
| 9,155,909 B2 | 10/2015 | Ishikawa |
| 9,179,982 B2 | 11/2015 | Kunz et al. |
| 9,205,281 B2 | 12/2015 | Mazin |
| 9,360,570 B2 | 6/2016 | Rothfuss et al. |
| 9,370,672 B2 | 6/2016 | Parsai et al. |
| 9,437,339 B2 | 9/2016 | Echner |
| 9,437,340 B2 | 9/2016 | Echner et al. |
| 9,498,167 B2 | 11/2016 | Mostafavi et al. |
| 9,560,970 B2 | 2/2017 | Rose et al. |
| 9,575,192 B1 | 2/2017 | Ng et al. |
| 9,649,509 B2 | 5/2017 | Mazin et al. |
| 9,694,208 B2 | 7/2017 | Mazin et al. |
| 9,697,980 B2 | 7/2017 | Ogura et al. |
| 9,731,148 B2 | 8/2017 | Olivera et al. |
| 9,820,700 B2 | 11/2017 | Mazin |
| 9,878,180 B2 | 1/2018 | Schulte et al. |
| 9,886,534 B2 | 2/2018 | Wan et al. |
| 9,952,878 B2 | 4/2018 | Grimme et al. |
| 9,974,494 B2 | 5/2018 | Mostafavi et al. |
| 10,159,853 B2 | 12/2018 | Kuusela et al. |
| 10,327,716 B2 | 6/2019 | Mazin |
| 10,463,884 B2 | 11/2019 | Dempsey et al. |
| 10,478,133 B2 | 11/2019 | Levy et al. |
| 10,500,416 B2 | 12/2019 | Larkin et al. |
| 10,603,515 B2 | 3/2020 | Olcott et al. |
| 10,695,586 B2 | 6/2020 | Harper et al. |
| 10,702,715 B2 | 7/2020 | Pearce et al. |
| 10,745,253 B2 | 8/2020 | Saracen et al. |
| 10,795,037 B2 | 10/2020 | Olcott et al. |
| 10,959,686 B2 | 3/2021 | Mazin |
| 11,007,384 B2 | 5/2021 | Olcott et al. |
| 11,285,340 B2 | 3/2022 | Larkin et al. |
| 11,287,540 B2 | 3/2022 | Olcott et al. |
| 11,309,072 B2 | 4/2022 | Carmi |
| 11,369,806 B2 | 6/2022 | Laurence, Jr. et al. |
| 11,504,550 B2 | 11/2022 | Maolinbay |
| 11,511,133 B2 | 11/2022 | Olcott et al. |
| 11,627,920 B2 | 4/2023 | Mazin |
| 11,675,097 B2 | 6/2023 | Olcott et al. |
| 2002/0051513 A1 | 5/2002 | Pugachev et al. |
| 2002/0148970 A1 | 10/2002 | Wong et al. |
| 2002/0163994 A1 | 11/2002 | Jones |
| 2002/0191734 A1 | 12/2002 | Kojima et al. |
| 2002/0193685 A1 | 12/2002 | Mate et al. |
| 2003/0036700 A1 | 2/2003 | Weinberg |
| 2003/0043951 A1 | 3/2003 | Akers |
| 2003/0080298 A1 | 5/2003 | Karplus et al. |
| 2003/0105397 A1 | 6/2003 | Tumer et al. |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0120452 A1 | 6/2004 | Shapiro et al. |
| 2004/0158416 A1 | 8/2004 | Slates |
| 2004/0162457 A1 | 8/2004 | Maggiore et al. |
| 2004/0264640 A1 | 12/2004 | Myles |
| 2005/0028279 A1 | 2/2005 | de Mooy |
| 2005/0063516 A1 | 3/2005 | Kato et al. |
| 2005/0089135 A1 | 4/2005 | Toth et al. |
| 2005/0104001 A1 | 5/2005 | Shah |
| 2005/0197564 A1 | 9/2005 | Dempsey |
| 2005/0234327 A1 | 10/2005 | Saracen et al. |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0124854 A1 | 6/2006 | Shah |
| 2006/0173294 A1 | 8/2006 | Ein-Gal |

(56) References Cited

U.S. PATENT DOCUMENTS

| | | |
|---|---|---|
| 2006/0182326 A1 | 8/2006 | Schildkraut et al. |
| 2006/0193435 A1 | 8/2006 | Hara et al. |
| 2006/0193441 A1 | 8/2006 | Cadman |
| 2006/0208195 A1 | 9/2006 | Petrick et al. |
| 2006/0237652 A1 | 10/2006 | Kimchy et al. |
| 2007/0003010 A1* | 1/2007 | Guertin .............. A61B 6/4441 378/63 |
| 2007/0003123 A1 | 1/2007 | Fu et al. |
| 2007/0014391 A1 | 1/2007 | Mostafavi et al. |
| 2007/0023669 A1 | 2/2007 | Hefetz et al. |
| 2007/0025513 A1 | 2/2007 | Ghelmansarai |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0133749 A1 | 6/2007 | Mazin et al. |
| 2007/0164239 A1 | 7/2007 | Terwilliger et al. |
| 2007/0211857 A1 | 9/2007 | Urano et al. |
| 2007/0221869 A1 | 9/2007 | Song |
| 2007/0265528 A1 | 11/2007 | Xu et al. |
| 2007/0270693 A1 | 11/2007 | Fiedler et al. |
| 2008/0002811 A1 | 1/2008 | Allison |
| 2008/0031404 A1 | 2/2008 | Khamene et al. |
| 2008/0031406 A1 | 2/2008 | Yan et al. |
| 2008/0043910 A1* | 2/2008 | Thomas ................. H05H 7/02 378/65 |
| 2008/0103391 A1 | 5/2008 | Dos Santos Varela |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0203309 A1 | 8/2008 | Frach et al. |
| 2008/0205588 A1 | 8/2008 | Kim |
| 2008/0214927 A1 | 9/2008 | Cherry et al. |
| 2008/0217541 A1 | 9/2008 | Kim |
| 2008/0230705 A1 | 9/2008 | Rousso et al. |
| 2008/0235873 A1 | 10/2008 | Farooqui |
| 2008/0251709 A1 | 10/2008 | Cooke et al. |
| 2008/0253516 A1 | 10/2008 | Hui et al. |
| 2008/0262473 A1 | 10/2008 | Kornblau et al. |
| 2008/0272284 A1 | 11/2008 | Rietzel |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0067576 A1 | 3/2009 | Maltz |
| 2009/0086909 A1 | 4/2009 | Hui et al. |
| 2009/0116616 A1 | 5/2009 | Lu et al. |
| 2009/0131734 A1 | 5/2009 | Neustadter et al. |
| 2009/0169082 A1 | 7/2009 | Mizuta et al. |
| 2009/0236532 A1 | 9/2009 | Frach et al. |
| 2009/0256078 A1 | 10/2009 | Mazin |
| 2009/0309046 A1 | 12/2009 | Balakin |
| 2010/0010343 A1 | 1/2010 | Daghighian et al. |
| 2010/0040197 A1 | 2/2010 | Maniawski et al. |
| 2010/0054408 A1 | 3/2010 | Echner |
| 2010/0054412 A1 | 3/2010 | Brinks et al. |
| 2010/0063384 A1 | 3/2010 | Kornblau et al. |
| 2010/0065723 A1 | 3/2010 | Burbar et al. |
| 2010/0067660 A1 | 3/2010 | Maurer, Jr. et al. |
| 2010/0069742 A1 | 3/2010 | Partain et al. |
| 2010/0074400 A1 | 3/2010 | Sendai |
| 2010/0074498 A1 | 3/2010 | Breeding et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0276601 A1 | 11/2010 | Duraj et al. |
| 2011/0006212 A1 | 1/2011 | Shchory et al. |
| 2011/0044429 A1 | 2/2011 | Takahashi et al. |
| 2011/0057122 A1 | 3/2011 | Moyers |
| 2011/0073763 A1 | 3/2011 | Subbarao |
| 2011/0092814 A1 | 4/2011 | Yamaya et al. |
| 2011/0105895 A1 | 5/2011 | Kornblau et al. |
| 2011/0105897 A1 | 5/2011 | Kornblau et al. |
| 2011/0118588 A1 | 5/2011 | Kornblau et al. |
| 2011/0198504 A1 | 8/2011 | Eigen |
| 2011/0200170 A1 | 8/2011 | Nord et al. |
| 2011/0211665 A1 | 9/2011 | Maurer, Jr. et al. |
| 2011/0215248 A1 | 9/2011 | Lewellen et al. |
| 2011/0215259 A1 | 9/2011 | Iwata |
| 2011/0215529 A1 | 9/2011 | Garrison |
| 2011/0228910 A1* | 9/2011 | Gregerson ............. A61B 6/035 324/309 |
| 2011/0272600 A1 | 11/2011 | Bert et al. |
| 2011/0297833 A1 | 12/2011 | Takayama |
| 2011/0301449 A1 | 12/2011 | Maurer, Jr. |
| 2011/0309252 A1 | 12/2011 | Moriyasu et al. |
| 2011/0309255 A1 | 12/2011 | Bert et al. |
| 2011/0313231 A1 | 12/2011 | Guertin et al. |
| 2011/0313232 A1 | 12/2011 | Balakin |
| 2012/0035470 A1 | 2/2012 | Kuduvalli et al. |
| 2012/0068076 A1 | 3/2012 | Daghighian |
| 2012/0076269 A1 | 3/2012 | Roberts |
| 2012/0138806 A1 | 6/2012 | Holmes et al. |
| 2012/0161014 A1 | 6/2012 | Yamaya et al. |
| 2012/0174317 A1 | 7/2012 | Saracen et al. |
| 2012/0203490 A1 | 8/2012 | Sayeh et al. |
| 2012/0213334 A1 | 8/2012 | Dirauf et al. |
| 2012/0230464 A1 | 9/2012 | Ling et al. |
| 2012/0318989 A1 | 12/2012 | Park et al. |
| 2012/0323117 A1 | 12/2012 | Neustadter et al. |
| 2013/0025055 A1 | 1/2013 | Saracen et al. |
| 2013/0060134 A1 | 3/2013 | Eshima et al. |
| 2013/0092842 A1 | 4/2013 | Zhang et al. |
| 2013/0109904 A1 | 5/2013 | Siljamaki et al. |
| 2013/0111668 A1 | 5/2013 | Wiggers et al. |
| 2013/0154647 A1* | 6/2013 | Yang .................. G01R 33/283 324/318 |
| 2013/0193330 A1 | 8/2013 | Wagadarikar et al. |
| 2013/0266116 A1 | 10/2013 | Abenaim et al. |
| 2013/0279658 A1 | 10/2013 | Mazin |
| 2013/0327932 A1 | 12/2013 | Kim et al. |
| 2013/0343509 A1 | 12/2013 | Gregerson et al. |
| 2014/0029715 A1 | 1/2014 | Hansen et al. |
| 2014/0079179 A1 | 3/2014 | Takagaki et al. |
| 2014/0104051 A1 | 4/2014 | Breed |
| 2014/0107390 A1 | 4/2014 | Brown et al. |
| 2014/0110573 A1 | 4/2014 | Wang et al. |
| 2014/0163368 A1 | 6/2014 | Rousso et al. |
| 2014/0184197 A1 | 7/2014 | Dolinsky |
| 2014/0193336 A1 | 7/2014 | Rousso et al. |
| 2014/0217294 A1 | 8/2014 | Rothfuss et al. |
| 2014/0224963 A1 | 8/2014 | Guo et al. |
| 2014/0228613 A1 | 8/2014 | Mazin et al. |
| 2014/0239204 A1 | 8/2014 | Orton et al. |
| 2014/0257096 A1 | 9/2014 | Prevrhal et al. |
| 2014/0275697 A1 | 9/2014 | Filiberti |
| 2014/0341351 A1 | 11/2014 | Berwick et al. |
| 2014/0355735 A1 | 12/2014 | Choi et al. |
| 2014/0378816 A1* | 12/2014 | Oh ........................ A61B 6/54 600/407 |
| 2015/0018673 A1 | 1/2015 | Rose et al. |
| 2015/0035942 A1 | 2/2015 | Hampton et al. |
| 2015/0076357 A1 | 3/2015 | Frach |
| 2015/0078528 A1 | 3/2015 | Okada |
| 2015/0126801 A1 | 5/2015 | Matteo et al. |
| 2015/0131774 A1 | 5/2015 | Maurer, Jr. et al. |
| 2015/0131781 A1 | 5/2015 | Ohashi et al. |
| 2015/0150740 A1 | 6/2015 | Lewald et al. |
| 2015/0168567 A1 | 6/2015 | Kim et al. |
| 2015/0170778 A1 | 6/2015 | Echner et al. |
| 2015/0177394 A1 | 6/2015 | Dolinsky et al. |
| 2015/0190658 A1 | 7/2015 | Yu |
| 2015/0276947 A1 | 10/2015 | Hoenk et al. |
| 2015/0285922 A1 | 10/2015 | Mintzer et al. |
| 2015/0301201 A1 | 10/2015 | Rothfuss et al. |
| 2016/0023019 A1 | 1/2016 | Filiberti et al. |
| 2016/0045173 A1 | 2/2016 | Bailey et al. |
| 2016/0073977 A1 | 3/2016 | Mazin |
| 2016/0097866 A1 | 4/2016 | Williams |
| 2016/0146949 A1 | 5/2016 | Frach et al. |
| 2016/0155228 A1 | 6/2016 | Sakata et al. |
| 2016/0206203 A1 | 7/2016 | Yu et al. |
| 2016/0209515 A1 | 7/2016 | Da Silva Rodrigues et al. |
| 2016/0219686 A1 | 7/2016 | Nakayama et al. |

(56) References Cited

U.S. PATENT DOCUMENTS

| | | |
|---|---|---|
| 2016/0266260 A1 | 9/2016 | Preston |
| 2016/0273958 A1 | 9/2016 | Hoenk et al. |
| 2016/0287347 A1 | 10/2016 | Meier |
| 2016/0299240 A1 | 10/2016 | Cho et al. |
| 2016/0325117 A1 | 11/2016 | Arai |
| 2016/0361566 A1 | 12/2016 | Larkin et al. |
| 2016/0374632 A1 | 12/2016 | David |
| 2017/0014648 A1 | 1/2017 | Mostafavi |
| 2017/0036039 A1 | 2/2017 | Gaudio |
| 2017/0052266 A1 | 2/2017 | Kim et al. |
| 2017/0065834 A1 | 3/2017 | Liu |
| 2017/0082759 A1 | 3/2017 | Lyu et al. |
| 2017/0199284 A1 | 7/2017 | Silari et al. |
| 2017/0220709 A1 | 8/2017 | Wan et al. |
| 2017/0242136 A1 | 8/2017 | O'Neill et al. |
| 2017/0281975 A1 | 10/2017 | Filiberti et al. |
| 2018/0133508 A1 | 5/2018 | Pearce et al. |
| 2018/0292550 A1 | 10/2018 | Xu et al. |
| 2019/0018154 A1 | 1/2019 | Olcott et al. |
| 2019/0070437 A1 | 3/2019 | Olcott et al. |
| 2019/0091487 A1 | 3/2019 | Pal et al. |
| 2019/0126069 A1 | 5/2019 | Nord et al. |
| 2019/0143145 A1 | 5/2019 | Laurence, Jr. et al. |
| 2019/0357859 A1 | 11/2019 | Mazin |
| 2020/0016432 A1 | 1/2020 | Maolinbay |
| 2020/0164230 A1 | 5/2020 | Larkin et al. |
| 2020/0215355 A1 | 7/2020 | Olcott et al. |
| 2020/0222724 A1 | 7/2020 | Mazin et al. |
| 2020/0368551 A1 | 11/2020 | Bassalow et al. |
| 2021/0196212 A1 | 7/2021 | Mazin |
| 2021/0260408 A1 | 8/2021 | Olcott et al. |
| 2021/0267683 A1 | 9/2021 | Brown |
| 2022/0093285 A1 | 3/2022 | Burns |
| 2022/0096867 A1 | 3/2022 | Mazin et al. |
| 2022/0143422 A1 | 5/2022 | Harper |
| 2022/0193451 A1 | 6/2022 | Duval et al. |
| 2022/0296929 A1 | 9/2022 | Laurence, Jr. et al. |
| 2022/0395707 A1 | 12/2022 | Laurence, Jr. et al. |
| 2023/0218928 A1 | 7/2023 | Maolinbay |
| 2023/0256268 A1 | 8/2023 | Olcott et al. |
| 2023/0337991 A1 | 10/2023 | Mazin |

FOREIGN PATENT DOCUMENTS

| | | |
|---|---|---|
| CN | 1799509 A | 7/2006 |
| CN | 1960780 A | 5/2007 |
| CN | 101297759 A | 11/2008 |
| CN | 101378805 A | 3/2009 |
| CN | 101803929 A | 8/2010 |
| CN | 101970043 A | 2/2011 |
| CN | 102160913 A | 8/2011 |
| CN | 102755696 A | 10/2012 |
| CN | 102760505 A | 10/2012 |
| CN | 202620505 U | 12/2012 |
| CN | 103006253 A | 4/2013 |
| CN | 103071241 A | 5/2013 |
| CN | 103126713 A | 6/2013 |
| CN | 103517737 A | 1/2014 |
| CN | 103648392 A | 3/2014 |
| CN | 103650095 A | 3/2014 |
| CN | 103932789 A | 7/2014 |
| CN | 105073188 A | 11/2015 |
| CN | 106461801 A | 2/2017 |
| DE | 199 50 794 A1 | 6/2001 |
| DE | 10-2008-053321 A1 | 5/2010 |
| DE | 10-2013-205606 A1 | 10/2014 |
| EP | 0 437 434 A1 | 7/1995 |
| EP | 0 817 978 A1 | 8/2001 |
| EP | 0 984 393 B1 | 3/2007 |
| EP | 1 762 177 A2 | 3/2007 |
| EP | 1 454 653 B1 | 9/2007 |
| EP | 1 402 761 B1 | 8/2008 |
| EP | 1 501 604 B1 | 12/2009 |
| EP | 1 898 234 B1 | 4/2010 |
| EP | 2 188 815 B1 | 11/2011 |
| EP | 1 660 175 B1 | 2/2012 |
| EP | 2 687 259 A1 | 1/2014 |
| EP | 2 777 768 A1 | 9/2014 |
| EP | 2 872 913 B1 | 2/2016 |
| EP | 2 874 702 B1 | 9/2016 |
| EP | 1 664 752 B1 | 6/2017 |
| FR | 2839894 A1 | 11/2003 |
| GB | 69634119 T2 | 2/2006 |
| GB | 2513596 A | 11/2014 |
| IL | 208396 | 12/2010 |
| JP | S-54-22192 A | 2/1979 |
| JP | S-54-99880 A | 8/1979 |
| JP | S-55-75305 A | 6/1980 |
| JP | S-60-236594 A | 11/1985 |
| JP | S-61-172538 A | 8/1986 |
| JP | H-01-156830 A | 6/1989 |
| JP | H-03-277350 A | 12/1991 |
| JP | H-08-511451 A | 12/1996 |
| JP | 09-33658 A | 2/1997 |
| JP | H-09-122110 A | 5/1997 |
| JP | 9-189769 A2 | 7/1997 |
| JP | H-11-290466 A | 10/1999 |
| JP | H-11-313900 A | 11/1999 |
| JP | 2000-105279 A | 4/2000 |
| JP | 2000-342639 A | 12/2000 |
| JP | 2001-340474 A | 12/2001 |
| JP | 2002-263090 A | 9/2002 |
| JP | 2003-534823 A | 11/2003 |
| JP | 2004-073404 A | 3/2004 |
| JP | 2004-513735 A | 5/2004 |
| JP | 2005-261941 A | 9/2005 |
| JP | 2006-145281 A | 6/2006 |
| JP | 2007-502166 A | 2/2007 |
| JP | 2007-507246 A | 3/2007 |
| JP | 2008-173184 A | 7/2008 |
| JP | 2008-173299 A | 7/2008 |
| JP | 2008-237911 A | 10/2008 |
| JP | 2009-522055 A | 6/2009 |
| JP | 2009-544101 A | 12/2009 |
| JP | 2010-500910 A | 1/2010 |
| JP | 2010-517655 A | 5/2010 |
| JP | 2011-007614 A | 1/2011 |
| JP | 2011-508654 A | 3/2011 |
| JP | 2011-514213 A | 5/2011 |
| JP | 2012-042344 A | 3/2012 |
| JP | 2012-506748 A | 3/2012 |
| JP | 2012-129984 A | 7/2012 |
| JP | 2012-254146 A | 12/2012 |
| JP | 2013-257320 A | 12/2013 |
| JP | 2013-545560 A | 12/2013 |
| JP | 2014-061445 A | 4/2014 |
| JP | 2014-521370 A | 8/2014 |
| JP | 2015-231497 A | 12/2015 |
| NL | 9520013 A | 2/1997 |
| WO | WO-89/10090 A1 | 11/1989 |
| WO | WO-95/22241 A1 | 8/1995 |
| WO | WO-00/15299 A1 | 3/2000 |
| WO | WO-03/076003 A2 | 9/2003 |
| WO | WO-03/076003 A3 | 9/2003 |
| WO | WO-2004/017832 A2 | 3/2004 |
| WO | WO-2004/017832 A3 | 3/2004 |
| WO | WO-2004/105574 A2 | 12/2004 |
| WO | WO-2004/105574 A3 | 12/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/094002 A2 | 8/2007 |
| WO | WO-2007/094002 A3 | 8/2007 |
| WO | WO-2007/124760 A1 | 11/2007 |
| WO | WO-2008/019118 A2 | 2/2008 |
| WO | WO-2008/019118 A3 | 2/2008 |
| WO | WO-2008/024463 A2 | 2/2008 |
| WO | WO-2008/024463 A3 | 2/2008 |
| WO | WO-2009/111580 A2 | 9/2009 |
| WO | WO-2009/111580 A3 | 9/2009 |
| WO | WO-2009/114117 A2 | 9/2009 |

(56) References Cited

FOREIGN PATENT DOCUMENTS

| | | |
|---|---|---|
| WO | WO-2009/114117 A3 | 9/2009 |
| WO | WO-2010/015358 A1 | 2/2010 |
| WO | WO-2010/018477 A2 | 2/2010 |
| WO | WO-2010/018477 A3 | 2/2010 |
| WO | WO-2010/109585 A1 | 9/2010 |
| WO | WO-2010/110255 A1 | 9/2010 |
| WO | WO-2012/135771 A1 | 10/2012 |
| WO | WO-2013/168043 A2 | 11/2013 |
| WO | WO-2013/168043 A3 | 11/2013 |
| WO | WO-2015/038832 A1 | 3/2015 |
| WO | WO-2015/042510 A1 | 3/2015 |
| WO | WO-2015/103564 A1 | 7/2015 |
| WO | WO-2015/134953 A1 | 9/2015 |
| WO | WO-2015/161036 A1 | 10/2015 |
| WO | WO-2016/061877 A1 | 4/2016 |
| WO | WO-2016/097977 A1 | 6/2016 |
| WO | WO-2016/203822 A1 | 12/2016 |
| WO | WO-2017/220116 A1 | 12/2017 |

OTHER PUBLICATIONS

Chen, Y. et al. (2011). Dynamic tomotherapy delivery, *Am. Assoc. Phys. Med.* 38:3013-3024.
Corrected Notice of Allowability dated Jan. 29, 2020, for U.S. Appl. No. 16/100,054, filed Aug. 9, 2018, 4 pages.
Dieterich, S. et al. (2003). "Skin respiratory motion tracking for stereotactic radiosurgery using the CyberKnife," *Elsevier Int'l Congress Series* 1256:130-136.
Erdi, Y.E. (2007). "The use of PET for radiotherapy," *Curr. Medical Imaging Reviews* 3(1):3-16.
Extended European Search Report dated Oct. 7, 2015, for European Application No. 12 763 280.0, filed on Mar. 30, 2012, 11 pages.
Extended European Search Report dated Mar. 31, 2017, for European Application No. 09 719 473.2, filed on Mar. 9, 2009, 8 pages.
Fan, Q. et al. (2012). "Emission Guided Radiation Therapy for Lung and Prostate Cancers: A Feasibility Study on a Digital Patient," *Med. Phys.* 39(11):7140-7152.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Final Office Action dated Aug. 15, 2012, for U.S. Appl. No. 13/209,275, filed Aug. 12, 2011, 8 pages.
Galvin, J.M. (2018). "The multileaf collimator—A complete guide," 17 total pages.
Gibbons, J.P. (2004). "Dose calculation and verification for tomotherapy," 2004 ACMP Meeting, Scottsdale, AZ., 71 total pages.
Glendinning, A.G. et al. (2001). "Measurement of the response of $Gd_2O_2S$:Tb phosphor to 6 MV x-rays," *Phys. Mol. Biol.* 46:517-530.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report dated May 4, 2009, for PCT Application No. PCT/US2009/01500, filed on Mar. 9, 2009, 3 pages.
International Search Report dated Jul. 20, 2012, for PCT Patent Application No. PCT/US2012/031704, filed on Mar. 30, 2012, 2 pages.
International Search Report dated Mar. 7, 2018, for PCT Application No. PCT/US2017/061848, filed on Nov. 15, 2017, 4 pages.
International Search Report dated Oct. 2, 2018, for PCT Application No. PCT/US2018/041700, filed on Jul. 11, 2018, 2 pages.
International Search Report dated Oct. 24, 2018, for PCT Application No. PCT/US2018/046132, filed on Aug. 9, 2018, 2 pages.
International Search Report dated Mar. 13, 2018, for PCT Application No. PCT/US2017/061855, filed on Nov. 15, 2017, 4 pages.
International Search Report dated Jun. 20, 2018, for PCT Application No. PCT/US2018/025252, filed on Mar. 29, 2018, 2 pages.
International Search Report dated Jan. 30, 2019, for PCT Application No. PCT/US2018/061099, filed on Nov. 14, 2018, 4 pages.
Kapatoes, J.M. et al. (2001). "A feasible method for clinical delivery verification and dose reconstruction in tomotherapy," *Med. Phys.* 28:528-542.
Keall, P.J. et al. (2001). "Motion adaptive x-ray therapy: a feasibility study," *Phys. Med. Biol.* 46:1-10.
Kim, H. et al. (2009). "A multi-threshold method for the TOF-PET Signal Processing," *Nucl. Instrum. Meth. Phys. Res. A.* 602:618-621.
Krouglicof, N. et al. (2013). "Development of a Novel PCB-Based Voice Coil Actuator for Opto-Mechatronic Applications," *presented at IEEE/RSJ International Conference on Intelligent Robots and Systems (IROS)*, Tokyo, Japan, Nov. 3-7, 2013, pp. 5834-5840.
Langen, K.M. et al. (2010). "QA for helical tomotherapy: report of the AAPM Task Group 148," *Med. Phys.* 37:4817-4853.
Mackie, T.R. et al. (Nov.-Dec. 1993). "Tomotherapy: A New Concept for the Delivery of Dynamic Conformal Radiotherapy," *Med. Phys.* 20(6):1709-1719.
Mazin, S. R. et al. (2010). "Emission-Guided Radiation Therapy: Biologic Targeting and Adaptive Treatment," *Journal of American College of Radiology* 7(12):989-990.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 8 pages.
Non-Final Office Action dated Sep. 19, 2013, for U.S. Appl. No. 13/895,255, filed May 15, 2013, 8 pages.
Non-Final Office Action dated Jan. 7, 2020, for U.S. Appl. No. 15/814,222, filed Nov. 15, 2017, 13 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated Oct. 5, 2017, for U.S. Appl. No. 14/951,194, filed Nov. 24, 2015, 11 pages.
Notice of Allowance dated Apr. 4, 2019, for U.S. Appl. No. 15/807,383, filed Nov. 8, 2017, 11 pages.
Notice of Allowance dated Dec. 4, 2019, for U.S. Appl. No. 16/100,054, filed Aug. 9, 2018, 13 pages.
Notice of Allowance dated Apr. 10, 2020, for U.S. Appl. No. 16/033,125, filed Jul. 11, 2018, 18 pages.
Notice of Allowance dated Apr. 30, 2020, for U.S. Appl. No. 15/814,222, filed Nov. 15, 2017, 10 pages.
North Shore LIJ (2008). IMRT treatment plans: Dosimetry measurements & monitor units validation, 133 total pages.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," *Med. Phys.* 42:7153-7168.
Partial Supplementary European Search Report dated Jun. 25, 2015, for European Application No. 12 763 280.0, filed on Mar. 30, 2012, 6 pages.
Prabhakar, R. et al. (2007). "An Insight into PET-CT Based Radiotherapy Treatment Planning," *Cancer Therapy* (5):519-524.
Schleifring (2013). Slip Ring Solutions—Technology, 8 total pages.
Tashima, H. et al. (2012). "A Single-Ring Open PET Enabling PET Imaging During Radiotherapy," *Phys. Med. Biol.* 57(14):4705-4718.
TomoTherapy® (2011). TomoHD Treatment System, Product Specifications, 12 total pages.
Varian Medical Systems (2004). "Dynamic Targeting™ Image-Guided Radiation Therapy—A Revolution in Cancer Care," *Business Briefing: US Oncology Review*, Abstract only, 2 pages.
Wikipedia (2016). "Scotch yoke," Retrieved from https://en.wikipedia.org/wiki/Scotch_yoke, 3 pages.

(56) References Cited

OTHER PUBLICATIONS

Willoughby, T. et al. (2012). "Quality assurance for nonradiographic radiotherapy localization and positioning systems: Report of task group 147," Med. Phys. 39:1728-1747.
Written Opinion of the International Searching Authority dated May 4, 2009, for PCT Application No. PCT/US2009/01500, filed on Mar. 9, 2009, 5 pages.
Written Opinion of the International Searching Authority dated Jul. 20, 2012, for PCT Patent Application No. PCT/US2012/031704, filed on Mar. 30, 2012, 10 pages.
Written Opinion of the International Searching Authority dated Mar. 7, 2018, for PCT Application No. PCT/US2017/061848, filed on Nov. 15, 2017, 5 pages.
Written Opinion of the International Searching Authority dated Oct. 2, 2018, for PCT Application No. PCT/US2018/041700, filed on Jul. 11, 2018, 19 pages.
Written Opinion of the International Searching Authority dated Oct. 24, 2018, for PCT Application No. PCT/US2018/046132, filed on Aug. 9, 2018, 7 pages.
Written Opinion of the International Searching Authority dated Mar. 13, 2018, for PCT Application No. PCT/US2017/061855, filed on Nov. 15, 2017, 6 pages.
Written Opinion of the International Searching Authority dated Jun. 20, 2018, for PCT Application No. PCT/US2018/025252, filed on Mar. 29, 2018, 12 pages.
Written Opinion of the International Searching Authority dated Jan. 30, 2019, for PCT Application No. PCT/US2018/061099, filed on Nov. 14, 2018, 11 pages.
Yamaya, T. et al. (2008). "A proposal of an open PET geometry," *Physics in Med. and Biology* 53:757-773.
Black, Q.C. et al. (2004). "Defining a Radiotherapy Target with positron emission tomography," Int. J. Radiation Oncology Biol. Phys. 60:1272-1282.
Li, X. et al. (2016). "Timing calibration for Time-of-Flight PET using positron-emitting isotopes and annihilation targets," IEEE Transactions on Nuclear Science 63:1351-1358.
Non-Final Office Action dated Jul. 5, 2022, for U.S. Appl. No. 17/203,532, filed Mar. 16, 2021, 13 pages.
Notice of Allowance dated Jul. 12, 2022, for U.S. Appl. No. 17/238,113, filed Apr. 22, 2021, 9 pages.
Notice of Allowance dated Jul. 21, 2022, for U.S. Appl. No. 16/582,286, filed Sep. 25, 2019, 7 pages.
Wang, D. et al. (2006). "Initial experience of FOG-PET/CT guided IMRT of head-and-neck carcinoma," Int. J. Radiation Oncology Biol. Phys. 65:143-151.
Corrected Notice of Allowability dated Feb. 3, 2021, for U.S. Appl. No. 16/425,416, filed May 29, 2019, 2 pages.
Corrected Notice of Allowability dated May 17, 2022, for U.S. Appl. No. 16/191,131, filed Nov. 14, 2018, 8 pages.
Extended European Search Report dated Jun. 9, 2020, for EP Application No. 17 871 349.1, filed on Nov. 15, 2017, 6 pages.
Extended European Search Report dated Oct. 30, 2020, for EP Application No. 20 179 036.7, filed on Mar. 9, 2009, 12 pages.
Extended European Search Report dated Apr. 1, 2021, for EP Application No. 18 844 237.0, filed on Aug. 9, 2018, 8 pages.
Extended European Search Report dated May 26, 2021, for EP Application No. 18 832 571.6, filed on Jul. 11, 2018, 9 pages.
Extended European Search Report dated Mar. 30, 2022, for EP Application No. 21 195 331.0, filed on Nov. 15, 2017, 11 pages.
Final Office Action dated Nov. 1, 2018, for U.S. Appl. No. 15/179,823, filed Jun. 10, 2016, 12 pages.
Final Office Action dated Aug. 10, 2021, for U.S. Appl. No. 16/887,896, filed May 29, 2020, 66 pages.
Final Office Action dated Jan. 11, 2022, for U.S. Appl. No. 16/191,131, filed Nov. 14, 2018, 25 pages.
International Search Report dated Sep. 16, 2016, for PCT Application No. PCT/US2016/037051, filed on Jun. 10, 2016, 3 pages.
International Search Report dated Sep. 18, 2020, for PCT Application No. PCT/US2020/038218, filed on Jun. 17, 2020, 4 pages.

Lu, W. (2009). "Real-time motion-adaptive-optimization (MAO) in tomotherapy," Phys. Med. Biol. 54:4373-4398.
Lu, W. (2008). "Real-time motion-adaptive delivery (MAD) using binary MLC: I. Static beam (topotherapy) delivery," Phys. Med. Biol. 53:6491-6511.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action dated Aug. 30, 2018, for U.S. Appl. No. 15/179,823, filed Jun. 10, 2016, 11 pages.
Non-Final Office Action dated Mar. 8, 2019, for U.S. Appl. No. 15/179,823, filed Jun. 10, 2016, 11 pages.
Non-Final Office Action dated Sep. 19, 2019, for U.S. Appl. No. 16/217,417, filed Dec. 12, 2018, 7 pages.
Non-Final Office Action dated Oct. 5, 2020, for U.S. Appl. No. 16/887,896, filed May 29, 2020, 62 pages.
Non-Final Office Action dated Oct. 29, 2020, for U.S. Appl. No. 16/834,956, filed Mar. 30, 2020, 7 pages.
Non-Final Office Action dated Nov. 3, 2020, for U.S. Appl. No. 16/818,325, filed Mar. 13, 2020, 9 pages.
Non-Final Office Action dated May 5, 2021, for U.S. Appl. No. 16/677,200, filed Nov. 7, 2019, 15 pages.
Non-Final Office Action dated Mar. 12, 2021, for U.S. Appl. No. 16/887,896, filed May 29, 2020, 64 pages.
Non-Final Office Action dated Apr. 26, 2021, for U.S. Appl. No. 16/191,131, filed Nov. 14, 2018, 28 pages.
Notice of Allowance dated Jan. 12, 2021, for U.S. Appl. No. 16/425,416, filed May 29, 2019, 13 pages.
Notice of Allowance dated Feb. 22, 2021, for U.S. Appl. No. 16/818,325, filed Mar. 13, 2020, 7 pages.
Notice of Allowance dated Sep. 23, 2019, for U.S. Appl. No. 15/179,823, filed Jun. 10, 2016, 10 pages.
Notice of Allowance dated Oct. 28, 2021, for U.S. Appl. No. 16/677,200, filed Nov. 7, 2019, 11 pages.
Notice of Allowance dated Dec. 22, 2021, for U.S. Appl. No. 16/887,896, filed May 29, 2020, 11 pages.
Notice of Allowance dated Apr. 29, 2022, for U.S. Appl. No. 16/191,131, filed Nov. 14, 2018, 11 pages.
Notice of Allowance dated Jun. 30, 2022, for U.S. Appl. No. 16/582,286, filed Sep. 25, 2019, 10 pages.
Olivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Written Opinion of the International Searching Authority dated Sep. 16, 2016, for PCT Application No. PCT/US2016/037051, filed on Jun. 10, 2016, 5 pages.
Written Opinion of the International Searching Authority dated Sep. 18, 2020, for PCT Application No. PCT/US2020/038218, filed on Jun. 17, 2020, 5 pages.
Extended European Search Report dated Sep. 2, 2020, for EP Application No. 17 871 896.1, filed on Nov. 15, 2017, 9 pages.
International Search Report dated Jan. 30, 2020, for PCT Application No. PCT/US2019/061180, filed on Nov. 13, 2019, 2 pages.
MPO Magazine (2017). "FDA clears ViewRay's MRI-guided radiation therapy system," located at https://www.mpo-mag.com/contents/view_breaking-news/2017-02-28/fda-clears-viewrays-mri-guided-radiation-therapy-system/, 1 total page.
Notice of Allowance dated Apr. 3, 2020, for U.S. Appl. No. 15/814,276, filed Nov. 15, 2017, 10 pages.
Partial Supplementary European Search Report dated Jun. 2, 2020, for European Application No. 17 871 896.1, filed on Nov. 15, 2017, 11 pages.
Supplemental Notice of Allowability dated May 27, 2020, for U.S. Appl. No. 15/814,276, filed Nov. 15, 2017, 2 pages.
ViewRay's MRIDIAN LINAC enables radiosurgery with MRI vision for cancer therapy, (2017). YouTube video located at https://www.youtube.com/watch?v=zm3g-BISYDQ, PDF of Video Screenshot Provided.
Written Opinion of the International Searching Authority dated Jan. 30, 2020, for PCT Application No. PCT/US2019/061180, filed on Nov. 13, 2019, 5 pages.
U.S. Appl. No. 16/887,896, filed May 29, 2020, by Olcott et al.

(56) References Cited

OTHER PUBLICATIONS

U.S. Appl. No. 16/890,194, filed Jun. 2, 2020, by Bassalow et al.
Corrected Notice of Allowability dated Feb. 14, 2023, for U.S. Appl. No. 17/697,828, filed Mar. 17, 2022, 4 pages.
Corrected Notice of Allowability dated Feb. 23, 2023, for U.S. Appl. No. 17/697,828, filed Mar. 17, 2022, 2 pages.
Corrected Notice of Allowability dated Mar. 16, 2023, for U.S. Appl. No. 17/203,532, filed Mar. 16, 2021, 2 pages.
Extended European Search Report dated Mar. 18, 2019, for European Patent Application No. 16 808 458.0, filed on Jun. 10, 2016, 8 pages.
Final Office Action dated Aug. 22, 2023, for U.S. Appl. No. 17/852,067, filed Jun. 28, 2022, 23 pages.
Final Office Action dated Sep. 19, 2023, for U.S. Appl. No. 17/837,900, filed Jun. 10, 2022, 16 pages.
Non-Final Office Action dated Jan. 17, 2023, for U.S. Appl. No. 17/837,900, filed Jun. 10, 2022, 12 pages.
Non-Final Office Action dated Jan. 20, 2023, for U.S. Appl. No. 16/890,194, filed Jun. 2, 2020, 11 pages.
Non-Final Office Action dated Jan. 20, 2023, for U.S. Appl. No. 17/852,067, filed Jun. 28, 2022, 21 pages.
Non-Final Office Action dated Apr. 18, 2023, for U.S. Appl. No. 17/566,212, filed Dec. 30, 2021, 19 pages.
Non-Final Office Action dated Aug. 3, 2023, for U.S. Appl. No. 18/053,874, filed Nov. 9, 2022, 8 pages.
Non-Final Office Action dated Oct. 18, 2023, for U.S. Appl. No. 17/313,736, filed May 6, 2021, 8 pages.
Notice of Allowance dated Aug. 1, 2022, for U.S. Appl. No. 17/238,113, filed Apr. 22, 2021, 8 pages.
Notice of Allowance dated Dec. 15, 2022, for U.S. Appl. No. 17/203,532, filed Mar. 16, 2021, 8 pages.
Notice of Allowance dated Feb. 7, 2023, for U.S. Appl. No. 17/697,828, filed Mar. 17, 2022, 10 pages.
Notice of Allowance dated Jun. 20, 2023, for U.S. Appl. No. 16/890,194, filed Jun. 2, 2020, 11 pages.
Notice of Allowance dated Oct. 16, 2023, for U.S. Appl. No. 17/566,212, filed Dec. 30, 2021, 12 pages.
Zu'an, Z. et al. (2008). "Study on evaluation model of correlation between irradiation field accuracy and sinking of bed board due to gravity," Chin. J. Radiol. Health Deo. 17:484-486, 11 total pages (with English Translation).
Non-Final Office Action dated Nov. 16, 2023, for U.S. Appl. No. 17/543,550, filed Dec. 6, 2021, 8 pages.

\* cited by examiner

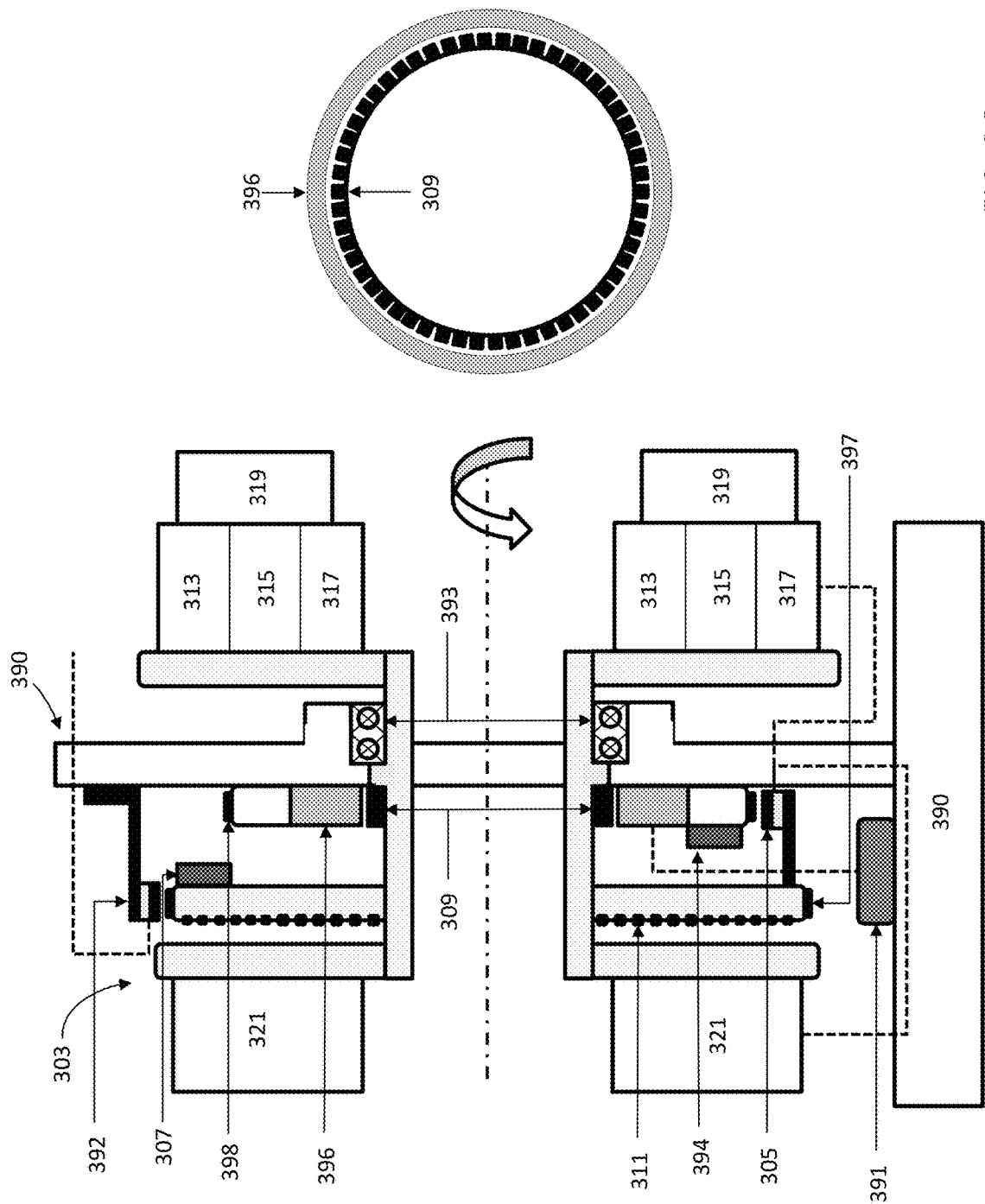

SYSTEM FOR EMISSION-GUIDED HIGH-ENERGY PHOTON DELIVERY

CROSS-REFERENCE TO RELATED APPLICATIONS

This application is a continuation of U.S. patent application Ser. No. 15/814,222 filed Nov. 15, 2017, now issued U.S. Pat. No. 10,695,586, which claims priority to U.S. Provisional Patent Application No. 62/422,404 filed Nov. 15, 2016, the disclosure of each of which is hereby incorporated by reference in its entirety.

STATEMENT REGARDING FEDERALLY SPONSORED RESEARCH OR DEVELOPMENT

This invention was made in part during work supported by grant number 2R44CA153466-02A1 from the National Cancer Institute of the National Institutes of Health. The government may have certain rights in the invention.

FIELD

The current invention relates to systems, devices, and methods for control of radiation therapy. The systems, devices, and methods may be used for emission-guided high-energy photon delivery.

BACKGROUND

Radiation therapy involves aiming radiation at a tumor from one or more directions. In some radiation therapy systems, the radiation source mounted on a gantry rotates around a patient on a table or couch, and directs radiation toward the patient's tumor(s). As the radiation source rotates around the patient, the patient table or couch may be moved in a direction that is parallel to the axis of rotation of the radiation source. In this manner, radiation may be applied to the patient's tumor(s) from various gantry angles and at various patient table or couch positions, based on images of the patient and the tumor(s) generated by various imaging modalities in advance of the treatment session.

Emission-guided radiation therapy (EGRT) applies radiation based on positron emission paths emitted by a positron emission tomography (PET) tracer that are localized to the tumor(s) during the treatment session. In addition to a radiation source to therapeutically irradiate a tumor region, an EGRT system also has an array of PET detectors to sense positron emission paths that originate within the tumor region, which may provide real-time location data. This may reduce the latency between the localization of a tumor and irradiation to that tumor. In order to timely respond to the detection of a positron emission path that indicates the real-time location of a tumor, the gantry of an emission-guided radiation therapy system may rotate at speeds ranging from about 10 rotations per minute (RPM) to about 70 RPM. Improvements to the gantry rotation mechanisms, the radiation source, and/or radiation sensors (e.g., PET detectors, gamma ray or X-ray detectors, etc.) may be desirable in order to accommodate this increased gantry rotation speed. Conversely, an increase in time resolution in the PET detectors may decrease the required rotational latency due to the confined spatial extents of the PET events that are coupled to the time resolution of those events.

BRIEF SUMMARY

Disclosed herein are radiation therapy systems and methods. The radiation therapy systems may comprise a gantry comprising a stationary frame and a rotatable ring that is configured to rotate up to about 70 RPM. The radiation therapy system may comprise a therapeutic radiation source, one or more beam-shaping components, imaging system(s) (e.g., one or more PET detectors, a kV CT imaging system), and supporting electronics mounted on the rotatable ring. These components may be mounted and arranged on the rotatable ring such that mechanical forces and/or other perturbations resulting from rapid ring rotation (e.g., about 50 RPM or more) do not interfere with their function. The radiation therapy system may also comprise a temperature management system that is configured to transfer heat generated by the components on the rotatable ring (and the heat generated by rotating the ring at speeds up to 70 RPM) to a facility cooling system via the stationary frame. These radiation therapy systems and methods may be used for biologically-guided radiation therapy, such as emission-guided radiation therapy, where gamma rays from markers or tracers that are localized to patient target region(s) (e.g., tumor regions) may be detected and used to direct radiation to the target region(s). These systems and methods may also help to reduce radiation exposure or delivery to non-target regions, such as normal or healthy tissue surrounding a tumor and/or radiation sensitive structures or organs (e.g., organs at risk).

One variation of a radiation therapy system may comprise a gantry comprising a stationary frame and a rotatable ring configured to rotate up to about 70 RPM, where the rotatable ring may comprise a drum having a first ring-shaped end surface, a second ring-shaped end surface opposite the first end surface, and a length therebetween such that deflection of the first and second end surfaces is less than about 0.5 mm when the ring rotates up to about 70 RPM. The system may further comprise a slip-ring located between the stationary frame and the rotatable ring and configured to communicate electrical signals therebetween while the rotatable ring rotates up to about 70 RPM, a therapeutic radiation source comprising a linear accelerator (linac) and a magnetron, one or more PET detectors mounted along the length of the drum, and a temperature management system that transfers heat from the rotatable ring to a cooling fluid on the stationary frame. The linac may be attached along the length of the drum by a first mounting assembly and enclosed in a radiation shield that is separate from the linac and first mounting assembly, and the magnetron may be radially mounted along the length of the drum such that a cathode support of the magnetron is aligned with a direction of a centripetal force that is generated while the rotatable ring rotates up to about 70 RPM. The radiation shield may be mounted to the gantry using a second mounting assembly that is separate from the first mounting assembly. For example, the second mounting assembly may not directly contact the first mounting assembly, and/or the first mounting assembly and the second mounting assembly may be separated by an air gap, and/or the linac and the radiation shield are separated by an air gap. The radiation shield and the second mounting assembly may not contact the linac. Optionally, some variations may comprise an actuator coupled to the linac and the first mounting assembly using a ball screw, such that a location of the linear accelerator is configured to be adjusted by the actuator. The actuator may or may not be removable, and/or may be controllable from a remote location, such as a location that is outside of the room within which the rotatable gantry is located.

The system may also comprise a first controller located on the rotatable ring and a second controller on the stationary frame. The first controller may generate control commands for the therapeutic radiation source and the one or more PET detectors, the second controller may generate control commands for a gantry motion system, and synchronization data between the first controller and the second controller may be transferred via the slip-ring. Activation of the therapeutic radiation source and acquisition of PET data may be based on a signal generated by the first controller, rotation of the ring may be based on a signal generated by the second controller, and a synchronization signal may be transmitted between the processors via the slip-ring to synchronize activation of the therapeutic radiation source, acquisition of PET data and gantry motion. In some variations, the slip-ring may comprise a data brush block and a power brush block. The system may further comprise a first communication interface comprising a first receiver element mounted to the rotatable ring and a first transmitter element mounted to the stationary frame that is configured to transmit a first plurality of signals to the first receiver element while the rotatable ring is moving, and a second communication interface comprising a second transmitter element mounted to the rotatable ring and a second receiver element mounted to the stationary frame. The second transmitter element may be configured to transmit a second plurality of signals to the second receiver element while the rotatable ring is moving. The first plurality of signals may be transmitted across the first communication interface and the second plurality signals (e.g., gantry rotation speed data, positron emission data from the one or more positron emission detectors, radiation data from a radiation detector mounted on the rotatable ring across from the therapeutic radiation source) may be transmitted across the second communication interface concurrently. In some variations, a system may comprise a multi-leaf collimator disposed in front of the radiation source, and the multi-leaf collimator may be configured to transmit position data of individual leaves of the multi-leaf collimator to the second transmitter element for transmission to the second receiver element. The second controller may be in communication with the first transmitter element, and the first plurality of signals comprises radiation source commands from the second controller. Alternatively or additionally, the first plurality of signals may comprise multi-leaf collimator commands, and/or gantry rotation commands from the second controller. The first communication interface and the second communication interface may transmit signals using inductive signal transfer methods or capacitive signal transfer methods.

Some variations may further comprise a first position sensor mounted to the rotatable ring and in communication with the first receiver element, and a second position sensor mounted to the stationary frame and in communication with the second receiver element. The rotatable ring may comprise a plurality of locator or index markers located around the circumference of the ring and detectable by the second position sensor, and the stationary frame may comprise a plurality of locator or index markers located around the circumference of the frame and detectable by the first position sensor. The first plurality of signals may comprise index marker data from the first position sensor and the second plurality of signals may comprise index marker data from the second position sensor. The first and/or second controller may be configured to receive and compare the first and second plurality of signals to identify a difference in the first and second plurality of signals. The first and/or second controller may be configured to generate a signal to indicate the difference between the first and second plurality of signals. The first plurality of signals may comprise angular position data of rotatable ring from the first position sensor and the second plurality of signals may comprise angular position data of the rotatable ring from the second position sensor. The system may further comprise a controller configured to receive and compare the first and second plurality of signals to identify a difference in the first and second plurality of signals. One variation of a method for identifying the difference between the first plurality of signals and second plurality of signals may comprise calculating a derivative of the first plurality of signals over time, calculating a derivative of the second plurality of signals over time, determining a difference between the calculated derivatives, and if the difference exceeds a predetermined threshold, generating a position sensor fault signal.

In some variations, the system may further comprise comprising a housing that defines a volume that encloses the gantry. The housing may comprise one or more lateral hatches along the length of the drum that are configured to allow access to the therapeutic radiation source and one or more PET detectors. A radiation therapy system may also comprise a motion system comprising a plurality of rotor elements around the rotatable ring, a stator element enclosed within the stationary frame across from the rotor elements, and ball bearings located adjacent to the plurality of rotor elements. The one or more rotor elements may comprise one or more magnetic or inductive elements, and the stator element may comprise a coil.

A radiation therapy system may also comprise a therapeutic radiation source that is configured to generate a radiation beam emitted along a beam path, the radiation beam having a two-dimensional projection having a x-axis aspect and a y-axis aspect, and the system further comprises a beam-limiting assembly disposed in the beam path. One variation of a beam-limited assembly may comprise upper jaws configured to shape the y-axis aspect of the radiation beam, a multi-leaf collimator configured to shape the x-axis aspect of the radiation beam, and lower jaws configured to shape the y-axis aspect of the radiation beam. The multi-leaf collimator may be located between the upper jaw and the lower jaw. The upper jaw may be located closer to the radiation source than the multi-leaf collimator and the lower jaw, and the lower jaw may be located further from the radiation source than the multi-leaf collimator and the upper jaw. The upper jaws may comprise inward faces that are angled at a first angle with respect to a vertical axis, and the lower jaws may comprise inward faces that are angled at a second angle with respect to a vertical axis, and the first angle may be less than the second angle. The radiation beam may have a beam spread and beam boundary defined by a focal line, and the upper jaws may comprise inward faces that are not aligned along the focal line, and the lower jaw. The inward faces of the upper jaws may be angled at a first angle with respect to a vertical axis, the inward faces of the lower jaws may be angled at a second angle with respect to the vertical axis, and the focal line may be angled at a third angle with respect to the vertical axis. The first angle may be less than the second angle.

The magnetron of a radiation therapy system may be configured to provide RF energy for accelerating electrons in the linac. The magnetron may comprise a ring anode having one or more cavities including a central cavity, a cathode located in the central cavity of the ring anode, and the cathode support may couple the cathode to the ring anode such that a longitudinal axis of the cathode support is aligned along the radial axis of the gantry.

In some variations, the temperature management system may comprise a first set of heat exchangers configured to transfer heat generated from the rotating ring to the stationary frame and a second set of heat exchangers configured to transfer the heat from the stationary frame to an external heat sink. For example, the external heat sink may be a closed-loop, facility liquid system.

Optionally, some variations of a radiation therapy system may comprise a second gantry mounted to the rotatable ring, and a kV system mounted on the second gantry. The kV system may comprise a kV radiation source and a rotatable collimator disposed in a beam path of the kV radiation source. The rotatable collimator may have a first configuration that blocks the beam and a second configuration that transmits the beam. Rotating the rotatable collimator may transition between the first and second configurations. The rotatable collimator may comprise a cylinder made of a radiation-blocking material and an aperture that is transverse to a longitudinal axis of the cylinder. In the first configuration, the aperture may not be aligned along the beam path and in the second configuration, the aperture may be aligned along the beam path.

One variation of a radiotherapy device may comprise a rotatable gantry comprising a bore and a radiation source coupled to the gantry. The bore of the rotatable gantry may comprise a first portion and a second portion, where the second portion diameter is greater than a first portion diameter. In one variation, at least a region of the second portion may comprise an ellipsoid. The radiotherapy device may further comprise an image projector configured to illuminate at least a region of the second portion. The illumination may comprise one or more images and/or videos. The radiotherapy device or system may optionally comprise a flexible display disposed along the surface of the bore. The flexible display may be an organic light-emitting diode (OLED) display. In some variations, a radiotherapy device may comprise an audio device configured to output sound within the bore. Optionally, a radiotherapy system may comprise an airflow device configured to direct airflow through the second portion of the bore. Some variations may comprise an optical eye tracker configured to detect one or more of an eye position and eye gaze of a patient in the bore, and a processor configured to change the illumination using the eye position and the eye gaze. The gantry corresponding to the first portion may be rotatable, and one or more of the gantry corresponding to the second portion and the radiation source may be stationary. The first portion may comprise a first end and a second end, where the first end may comprise a circular opening and the second portion may comprise an enclosure coupled to the second end. In some examples, the first portion diameter may be substantially constant and the second portion diameter may vary. In other examples, the second portion diameter may be greater than the first portion diameter by up to about four times.

Described herein is another variation of a radiotherapy system comprising a rotatable gantry comprising a patient region and configured to receive a patient on a patient platform and output a beam from a radiation source, a patient location system configured to locate the patient in the patient region, a microphone array and speaker array disposed in the patient region, and a processor configured to locate a patient's ears using the patient location system and to generate a noise cancellation signal using the microphone array and the ear locations. The speaker array may be configured to output the noise cancellation signal. In some variations, the microphone array and speaker array may be disposed in an end of the gantry. Also described herein is a method of noise cancellation for a radiotherapy system, which may comprise receiving ear location data of a patient disposed in a patient treatment area of a radiotherapy system, receiving noise generated from the radiotherapy system using a microphone array, generating a noise cancellation signal using the ear location data and the received noise, outputting the cancellation signal from a speaker array. The method may optionally comprise imaging the patient to generate the ear location data.

Also disclosed herein is a method of processing radiotherapy patients. One variation of such a method may comprise registering a first patient's body to a first patient platform using a registration system disposed in a registration room, moving the first patient's body on the first patient platform from the registration room to a radiotherapy room, docking the first patient platform to a radiotherapy system disposed in the radiotherapy room, where docking the first patient platform may comprise moving the first patient platform into a patient treatment region of the radiotherapy system, and treating the first patient using the radiotherapy system. Some methods may further comprise performing each step above for a second patient and a second patient platform after completing each step by the first patient. Methods may comprise administering a radioisotope to the first patient in an administering room and moving the first patient from the administering room into the registration room. These steps may be performed for a second patient and a second patient platform after completing each step for the first patient, and further for a third patient after completing each step for the second patient.

Disclosed herein is one variation of a method of operating a radiotherapy system, the method comprising providing the radiotherapy system comprising a rotatable gantry, a patient platform disposed in a patient region of the gantry and configured to move relative to the gantry, a collimator mounted to the gantry, the collimator comprising a plurality of leaves configured to open and close from a plurality of gantry angles, and a radiation source coupled to the collimator, receiving a treatment plan of a patient comprising a set of open leaves and corresponding gantry angles, outputting a radiation beam from the collimator using the radiation source and the treatment plan, and varying a speed of one or more of the patient platform and gantry using the treatment plan. In some variations, the method may comprise prioritizing a speed of the collimator over the speed of the patient platform and gantry. Prioritizing the speed of the collimator may comprise varying the speed of one or more of the patient platform and gantry to maintain a speed of the collimator. In some methods, the patient platform speed may be increased in absence of the radiation beam emission. Alternatively or additionally, the gantry speed may be constant and the patient platform speed may vary or the patient platform speed may be constant and the gantry speed may vary.

Disclosed herein is one variation of a method of locating a patient body structure, where the method may comprise coupling a radioactive fiducial to an external portion of the patient (where the radioactive fiducial corresponds to the patient body structure), locating the radioactive fiducial and the patient coupled to a patient platform, and registering the patient body structure to the patient platform using the location of the radioactive fiducial. The radioactive fiducial may comprise a hydrogel, and/or may be a 500 kilovolt point source. In some variations, the method may comprise treating the patient using a radiotherapy beam with the radioactive fiducial coupled to the patient. The method may optionally comprise locating the radioactive fiducial in parallel with the treating step, and determining movement of the patient body structure using the location data. In some variations, the method may comprise coupling a metal fiducial to the external portion of the patient, where the metal fiducial corresponds to the patient body structure, and locating the metal fiducial. The external portion may comprise one or more of skin, an orifice of the patient, a sternum, and a hip. In some variations, the method may comprise marking the patient at a first skin location corresponding to the patient body structure, where the radioactive fiducial may be coupled to the patient at the first location. Alternatively or additionally, the radioactive fiducial may comprise an orifice block configured for insertion in the orifice, and/or may be coupled to patient clothing configured to be worn on the patient.

Another variation of a method for locating a patient body structure may comprise locating an internal region of interest of a patient, implanting a radioactive fiducial into the region of interest, locating the radioactive fiducial and the patient coupled to a patient platform, and registering the region of interest to the patient platform using the location of the radioactive fiducial. The implanted radioactive fiducial may comprise one or more of a hydrogel and a tracer.

Also disclosed herein is a variation of a radiation therapy system that may comprise a rotatable gantry, a linear accelerator mounted to the gantry using a first mounting assembly, and a radiation shield disposed over the linear accelerator and mounted to the gantry using a second mounting assembly that is separate from the first mounting assembly. For example, the second mounting assembly may not directly contact the first mounting assembly, and/or the first mounting assembly and the second mounting assembly are separated by an air gap. The radiation shield and the second mounting assembly may not contact the linear accelerator, for example, the linear accelerator and the radiation shield may be separated by an air gap. In some variations, the gantry may comprise a housing with an exterior surface and an interior surface, and the first mounting assembly may be attached to the interior surface and the second mounting assembly may be attached to the exterior surface. The system may optionally comprise an actuator coupled to the first mounting assembly using a ball screw such that the actuator is coupled to the linear accelerator. The actuator may be configured to adjust the location of the linear accelerator. The actuator may be removable, and/or may be controllable from a remote location. For example, the rotatable gantry may be located in a room and the remote location may be outside of the room.

Disclosed herein is a variation of a radiation therapy system that may comprise a rotatable gantry comprising a rotatable ring movably coupled to a stationary frame, a radiation source mounted on the rotatable ring, a first communication interface comprising a first receiver element mounted to the rotatable ring and a first transmitter element mounted to the stationary frame that is configured to transmit a first plurality of signals to the first receiver element while the rotatable ring is moving, and a second communication interface comprising a second transmitter element mounted to the rotatable ring and a second receiver element mounted to the stationary frame, where the second transmitter element is configured to transmit a second plurality of signals to the second receiver element while the rotatable ring is moving. In some variations, the first plurality of signals may be transmitted across the first communication interface and the second plurality signals may be transmitted across the second communication interface concurrently. Some variations may comprise a multi-leaf collimator disposed in front of the radiation source, where the multi-leaf collimator may be configured to transmit position data of individual leaves of the multi-leaf collimator to the second transmitter element for transmission to the second receiver element. The second plurality of signals may comprise gantry rotation speed data. Some variations may also comprise one or more positron emission detectors, where the second plurality of signals comprises positron emission data from the one or more positron emission detectors. The system may comprise a radiation detector mounted on the rotatable ring across from the radiation source, where the second plurality of signals comprises radiation data from the radiation detector. A controller may be located on the stationary frame and in communication with the first transmitter element, where the first plurality of signals may comprise radiation source commands from the controller. The system may comprise a multi-leaf collimator disposed in front of the radiation source, where the first plurality of signals comprises multi-leaf collimator commands from the controller. The first plurality of signals may comprise gantry rotation commands from the controller. In some variations, the first communication interface and the second communication interface may transmit signals using inductive signal transfer methods. Optionally, the system may comprise a first position sensor mounted to the rotatable ring and in communication with the first receiver element, and a second position sensor mounted to the stationary frame and in communication with the second receiver element. The rotatable ring may comprise a plurality of index markers located around the circumference of the ring and detectable by the second position sensor, and the stationary frame may comprise a plurality of index markers located around the circumference of the frame and detectable by the first position sensor. The first plurality of signals may comprise index marker data from the first position sensor and the second plurality of signals comprises index marker data from the second position sensor. The system may further comprise a controller configured to receive and compare the first and second plurality of signals to identify a difference in the first and second plurality of signals. For example, the controller may be configured to generate a signal to indicate the difference between the first and second plurality of signals. The first plurality of signals may comprise angular position data of rotatable ring from the first position sensor and the second plurality of signals comprises angular position data of the rotatable ring from the second position sensor. The system may further comprise a controller configured to receive and compare the first and second plurality of signals to identify a difference in the first and second plurality of signals. Identifying the difference between the first plurality of signals and second plurality of signals may comprise calculating a derivative of the first plurality of signals over time, calculating a derivative of the second plurality of signals over time, determining a difference between the calculated derivatives, and if the difference exceeds a predetermined threshold, generating a position sensor fault signal.

Described herein is a variation of a radiation therapy system that may comprise a radiation source configured to generate a radiation beam emitted along a beam path, the radiation beam having a two-dimensional projection having a x-axis aspect and a y-axis aspect, and a beam-limiting assembly disposed in the beam path. The beam-limiting assembly may comprise upper jaws configured to shape the y-axis aspect of the radiation beam, a multi-leaf collimator configured to shape the x-axis aspect of the radiation beam, and lower jaws configured to shape the y-axis aspect of the radiation beam, where the multi-leaf collimator is located between the upper jaw and the lower jaw. In some examples, the upper jaw may be located closer to the radiation source than the multi-leaf collimator and the lower jaw, and the lower jaw may be located further from the radiation source than the multi-leaf collimator and the upper jaw. The radiation source may comprise a linear accelerator. The upper jaws may comprise inward faces that are angled at a first angle with respect to a vertical axis, and the lower jaws may comprise inward faces that are angled at a second angle with respect to a vertical axis, where the first angle is less than the second angle. The radiation beam may have a beam spread and beam boundary defined by a focal line, and the upper jaws may comprise inward faces that are not aligned along the focal line, and the lower jaw. The inward faces of the upper jaws may be angled at a first angle with respect to a vertical axis, the inward faces of the lower jaws may be angled at a second angle with respect to the vertical axis, and the focal line may be angled at a third angle with respect to the vertical axis, where the first angle may be less than the second angle.

Also disclosed herein is a variation of a radiation therapy system that may comprise a rotatable gantry comprising a rotatable ring movably coupled to a stationary frame, the rotatable gantry having a radial axis, a linear accelerator mounted on the rotatable ring, and a magnetron mounted on the rotatable ring configured to provide RF energy for accelerating electrons in the linear accelerator. The magnetron may comprise a ring anode having one or more cavities including a central cavity, a cathode located in the central cavity of the ring anode, and a cathode support that couples the cathode to the ring anode, wherein a longitudinal axis of the cathode support is aligned along the radial axis of the gantry. Rotation of the rotatable ring may generate a centripetal force having a direction, and where the longitudinal axis of the cathode support may be aligned along the direction of the centripetal force.

Described herein is a radiation therapy system that may comprise a gantry configured to rotate at speeds of at least 30 RPM, the gantry comprising a stationary frame and a rotatable ring coupled to the stationary frame, a radiation source mounted on the rotatable ring, and a temperature management system comprising first set of heat exchangers configured to transfer heat generated from the rotating ring to the stationary frame and a second set of heat exchangers configured to transfer the heat from the stationary frame to an external heat sink. The external heat sink may be a closed-loop, facility liquid system.

BRIEF DESCRIPTION OF THE DRAWINGS

FIG. 1A is a perspective view of a variation of a gantry and patient platform. FIG. 1B depicts a cross-sectional view of the gantry and patient platform of FIG. 1A. FIG. 1C depicts another perspective view of the gantry and patient platform of FIG. 1A.

FIG. 3F depicts a schematic side view of a variation of a gantry. FIG. 3G depicts a front view of rotor and stator elements for one variation of a gantry.

FIG. 4A is a cross-sectional view of a variation of a linac. FIG. 4B depicts an exploded perspective view of the linac of FIG. 4B.

FIG. 5A is a block diagram that represents one variation of a heat transfer or cooling pathway from a rotatable ring of the gantry to a stationary frame of the gantry. FIG. 5B is a front view of the gantry with one variation of a temperature management system. FIG. 5C is a side view of the gantry of FIG. 5B. FIG. 5D is a perspective view of the gantry of FIG. 5B. FIG. 5E is another perspective view of the gantry of FIG. 5A.

FIG. 6A is a cross-sectional side view of the gantry. FIG. 6B is a partial cut-away perspective view of the gantry of FIG. 6A.

FIG. 9A is a side view of the magnetron. FIG. 9B is a cross-sectional side view of a gantry and the magnetron of FIG. 9A.

DETAILED DESCRIPTION

Figure 1A:
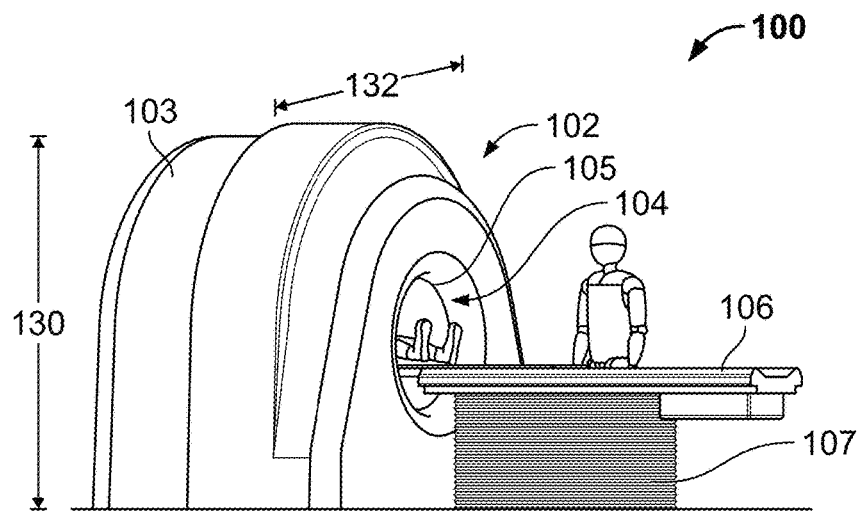
FIGS. 1A-1C are illustrative depictions of variations of an emission-guided radiation therapy system.

Generally described herein are systems, devices, and methods for emission-guided high-energy photon delivery. In some variations, the systems, devices, and methods may be used to deliver a radiation dose to a desired region of a patient (e.g., therapeutic dose to a patient tumor). Generally, the radiation therapy systems described herein may comprise a gantry comprising a rotatable ring coupled to a stationary frame via a rotating mechanism such that the rotatable ring rotates from about 10 RPM to about 70 RPM, a radiation source (e.g., MV X-ray source) mounted on the rotatable ring, and one or more PET detectors mounted on the rotatable ring. The radiation source mounted on the rotatable ring may deliver the radiation dose to the patient, and the PET detectors mounted on the rotatable ring may detect PET events. The radiation source and the PET detector may be co-planar (e.g., both mounted on the rotatable ring, arranged such that a beam plane of the radiation source is co-planar with a detection plane of the PET detector), and the PET detector may be arranged to avoid intersecting a therapeutic radiation beam path. The radiation therapy system may comprise a patient treatment area comprising a longitudinal bore or channel extending through the gantry. In some variations, the rotating ring may comprise a first communication interface and the stationary frame may comprise a second communication interface. In some of these examples, the first and second communication interfaces may both be configured to transmit and receive data therebetween while the ring is rotating.

In some variations, a gantry may comprise a temperature management system configured to dissipate any heat generated due to the motion of the rotatable ring. The temperature management system may comprise two sets of heat exchangers and ducting, the first set may be configured to transfer heat from the rotating gantry to the stationary frame and a second set located on the stationary frame may be configured to transfer heat from the stationary frame to an external thermal system (e.g., a closed-loop, facility liquid system). For example, the first set may comprise forced-air heat exchangers and/or radiative heat exchangers, and the second set may comprise heat exchangers coupled to external, chilled fluid of the external thermal system.

In some variations, a radiation therapy system may further comprise a radiation source mounted on the rotatable ring of the gantry. For example, the radiation source may comprise a linear accelerator (linac) and a radially-mounted magnetron. A cathode support of the magnetron may be oriented in a radial direction with respect to the gantry. Alternatively, the radiation source may comprise a linac and a klystron. A radiation beam pulse rate of the radiotherapy system may be varied by varying the pulse rate or length of the radiofrequency (RF) pulses generated by the radiation source (e.g., magnetron or klystron) with respect to an electron injection rate or length of the electron beam gun. In some variations, the linac may be mounted to the rotatable gantry using a first mounting assembly and a radiation shield disposed over the linac may be mounted to the gantry using a second mounting assembly separate from the first mounting assembly. In some variations, the second mounting assembly does not directly contact the first mounting assembly, and/or the first and second mounting assemblies may be separated by an air gap.

In other variations, one or more collimating elements may be located in the radiation beam path. For example, a radiation therapy system may comprise an upper jaw configured to shape a radiation beam along a first axis or dimension (e.g., y-axis or width), a multi-leaf collimator configured to shape the radiation beam along a second axis or dimension that is orthogonal to the first axis or dimension (e.g., x-axis or length), and a lower jaw configured to shape the radiation beam along the first axis or dimension or dimension. The position of the linac with respect to one or more collimating elements may be adjusted by a motor (e.g., actuator) that may be remotely-controlled. For example, the radiation therapy system may be in a room or bunker, and an operator located in a different room (e.g., control room) may be able to adjust the position of the linac by controlling the motor coupled to the linac. Optionally, a radiation therapy system may comprise an imaging radiation source (e.g., a kV X-ray source) mounted on the rotatable ring in addition to a therapeutic radiation source (e.g., a MV X-ray source), where the imaging radiation source may be configured to acquire images of the patient just before, and/or during, and/or after a treatment session. The imaging radiation source and the therapeutic radiation source may be located at different longitudinal locations along the length of the gantry bore (such that the radiation beam generated by the imaging radiation source is not co-planar with the therapeutic radiation source) or located at the same longitudinal location (such that the radiation beam plane generated by the imaging radiation source may be co-planar with the radiation beam plane generated by the therapeutic radiation source). In some variations, the imaging radiation source and the therapeutic radiation source may have a separate linac, radiation source, electron injector and beam converter assemblies, while in other variations, the imaging radiation source and the therapeutic radiation source may have the same linac, radiation source, electron injector and beam converter assembly.

In some variations of the system, a radiotherapy device having a rotatable gantry may comprise a bore configured to reduce patient discomfort due to confinement within a small space (e.g., claustrophobia). In some cases, a patient may be sedated during treatment to avoid claustrophobia and to limit patient movement on a patient platform. However, sedation poses risks and may be undesirable for some patient groups such as the elderly, patients with advanced disease, and/or patients taking medication. The radiotherapy devices, as described herein, may facilitate patient comfort related to confinement and encourage the patient to remain motionless for longer periods of time to receive radiotherapy treatment and may help to reduce the use of sedatives. In some variations, the bore may increase in diameter toward the end of the bore (i.e., a variable-diameter bore or stepped bore) with audio/visual sensory cues that simulate an enlarged space in order to reduce patient anxiety. In some variations, the rotatable gantry may be enclosed within a housing. The housing may comprise a longitudinal channel or bore that is sized for patient. The channel or bore may be open on one end and closed on an opposite end (e.g., closed bore) or may be open on both ends (e.g., open bore). The patient's comfort may further be enhanced by providing airflow over the patient while they are in the delivery system.

The radiation therapy systems disclosed herein may also be used in tomotherapy methods where the therapeutic radiation source rotates around a patient treatment region as the patient couch moves through the region. This may provide a helical or spiral pattern of X-ray irradiation. In some methods, the radiation directed toward the patient treatment area may be intensity-modulated, for example, where the intensity of the radiation beam at each gantry angle and each couch position may vary. For example, when higher levels of modulation are required by a treatment plan, the gantry and/or patient platform may slow down, and when less modulation is required, the gantry and/or patient platform may increase speed.

I. Systems

Gantry

Generally, the systems described herein may comprise a gantry having a stationary frame and rotatable ring coupled to the stationary frame via a rotating mechanism, a therapeutic radiation source (e.g., MV X-ray source) mounted on the rotatable ring, and one or more PET detectors mounted on the rotatable ring. The radiation therapy system may also comprise a MV detector mounted on the rotatable ring opposite the therapeutic radiation source. The beam emitted from the therapeutic radiation source may be shaped by one or more jaws, and/or a multi-leaf collimator (e.g., a binary multi-leaf collimator), and/or any number of beam-shaping components, such as additional collimators or jaws, as may be desirable. The rotating mechanism may comprise a slip ring and a drive train that are capable of rotating the ring from about 10 RPM to about 70 RPM. The rotatable ring may rotate about a patient treatment area, which may comprise a bore or channel through the gantry. The gantry may be enclosed within a housing that may have a housing bore or channel that corresponds to the gantry bore or channel. The gantry housing may be a mechanical and/or visual barrier between the patient and the gantry.

A radiation therapy system may also comprise a patient platform that is configured to move the patient into and out of the patient treatment area. The position of the patient platform within the bore or channel of the gantry, the position of the radiation source (which may be a therapeutic radiation source) around the patient treatment area (e.g., circumferential location of the radiation source around the gantry bore or channel) and the radiation pulses from the radiation source may be timed by a controller such that a desired dose is delivered to a desired region of the patient (e.g., a tumor region). In some variations, the rotatable ring may be configured to continuously rotate 360 degrees in one or more directions (e.g., clockwise and/or counterclockwise), while in other variations, the rotatable ring may be configured to rotate less than 360 degrees in one or more directions (e.g., rotate clockwise about 270 degrees and counterclockwise about 270 degrees, rotate clockwise about 150 degrees from a vertical axis and counterclockwise about 135 degrees from the vertical axis, rotate clockwise about 180 degrees from the vertical axis and about 150 degrees from the vertical axis, etc.).

The one or more PET detectors may be mounted along at least a portion of the circumference of the rotatable ring (e.g., inner circumference, outer circumference, or any location between the inner and outer circumference). The location of the PET detectors with respect to the length of the bore or patient area may be the same as the location of the MV or therapeutic radiation source and MV detector (e.g., on the same "slice" of the rotating ring). That is, the radiation beam emitted by the therapeutic radiation source may be on the same plane as the PET detectors. The PET detectors may be arranged to avoid intersecting with the radiation beam path, and instead, a MV detector may be located in the therapeutic radiation beam path. In some variations, the PET detectors may span a subset of the circumference of the ring (e.g., 180 degrees). For example, a first array of PET detectors may be mounted on a first segment or length of the rotatable ring that has a length of about 25% of the circumference of the ring and a second array of PET detectors may be mounted on a second segment or length of the ring that has a length of about 25% of the circumference of the ring. In this variation, the portion of the ring circumference that is covered by PET detectors is about 50% of the circumference. The first and second arrays of PET detectors may be located generally opposite each other (e.g., directly opposite each other, such that the center of each of the PET detector arrays are about 180 degrees from each other), or alternatively, the first array of PET detectors may be offset from the second array of PET detectors so that they are not opposite each other (e.g., the center of each of the PET detector arrays are less than about 180 degrees from each other, for example, about 45 degrees, about 90 degrees, or about 120 degrees, or about 150 degrees, etc.). In variations where the PET detectors are not on the same plane or "slice" of the rotating ring as the therapeutic radiation source (i.e., where the PET detectors are not co-planar with the therapeutic radiation source), the PET detectors may span the entire circumference of the ring (e.g., 360 degrees).

Figure 1B:
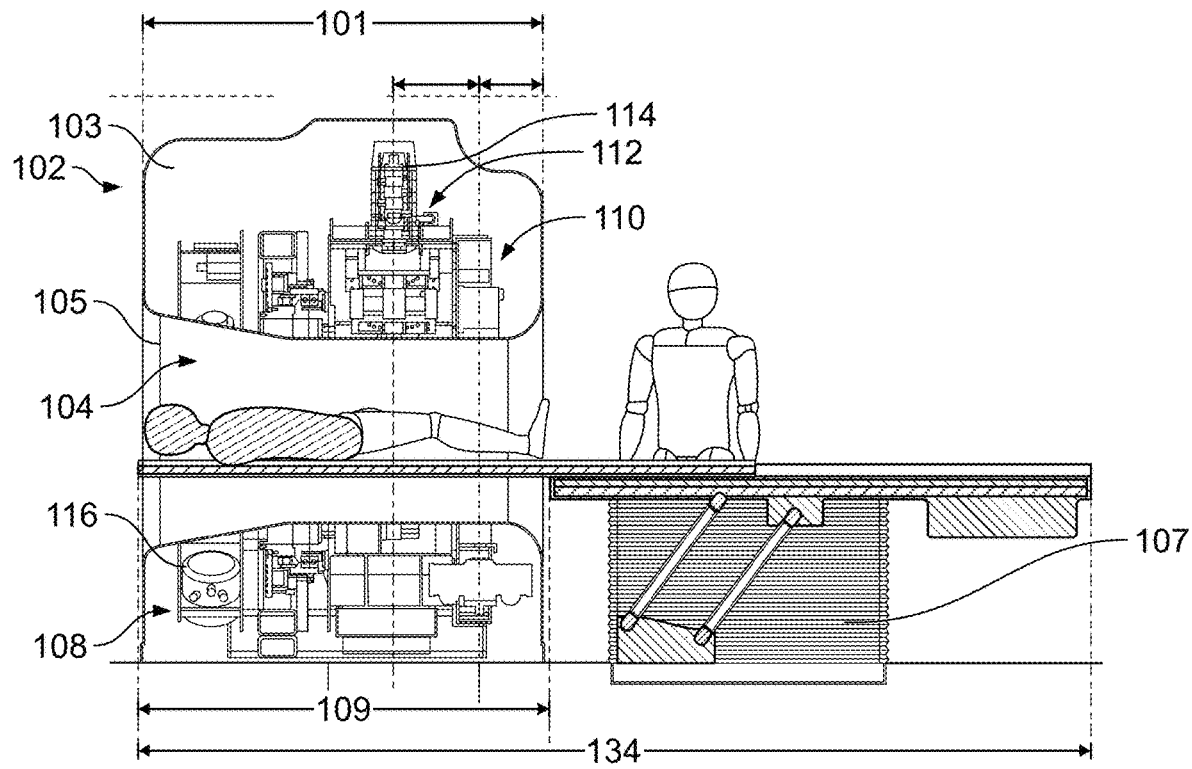

FIGS. 1A-B depict one variation of a radiation therapy system (100) (which may be an emission-guided radiation therapy system) comprising a gantry (102) enclosed within a housing (103), a patient treatment area (104) within a bore (105) of the gantry, and a patient platform (106). The gantry (102) may be a rotatable gantry, such as a circular gantry, comprising a stationary frame (108) and a rotatable ring (110) that may be configured to continuously rotate 360 degrees clockwise or counterclockwise (e.g., continuously rotating) from about 10 RPM to about 70 RPM with respect to the stationary frame (108). The housing (103) may have a shape that generally follows the contours of the gantry (102) such the patient platform (106) may be advanced into and out of the bore (105). Enclosed within the internal volume of the housing (103) and depicted in FIG. 1B, the radiation therapy system (100) may further comprise a therapeutic X-ray source or radiation source (112) such as a linear accelerator (linac) (114) mounted on the rotating ring (110) at a first longitudinal location along the bore (105) and an imaging X-ray source or radiation source (116) mounted on the rotating ring (110) at a second longitudinal location along the bore (105). In this variation, the radiation beams generated by the imaging radiation source (116) may not be co-planar with the radiation beams generated by the therapeutic radiation source (112). The length (101) of the bore (105) may be between about 120 cm and about 210 cm. In some variations, the length (101) of the bore (105) may be about 185 cm. A diameter of the bore (105) may be between about 60 cm and about 120 cm. In some variations, a diameter of the bore (105) may be about 85 cm. The patient platform (106) may be configured to extend from the platform base (107) such that the extension length (109) may be between about 150 cm and 250 cm. In some variations, the extension length (109) may be about 190 cm. The housing (103) may have a height (130) of between about 220 cm and about 280 cm. In some variations, the housing (103) may have a height of about 250 cm. The housing (103) may have a width (132) of between about 225 cm and 325 cm. In some variations, the housing (103) may have a width (132) of about 276 cm. The housing (103) may have a length between about 120 cm and 230 cm. In some variations, the housing (103) may have a length of about 185 cm. The length (134) of the radiation therapy system (100), including the gantry and the patient platform may be between about 400 cm and about 500 cm. In some variations, the length (134) of the radiation therapy system (100) may be about 439 cm. In some variations, the depth (e.g., pit) may be such that the axis of the bore (105) is about 110 cm from the bottom of the system (100). In some variations, the depth may be between about 10 cm and 60 cm. In some variations, the depth may be about 32 cm.

Figure 1C:
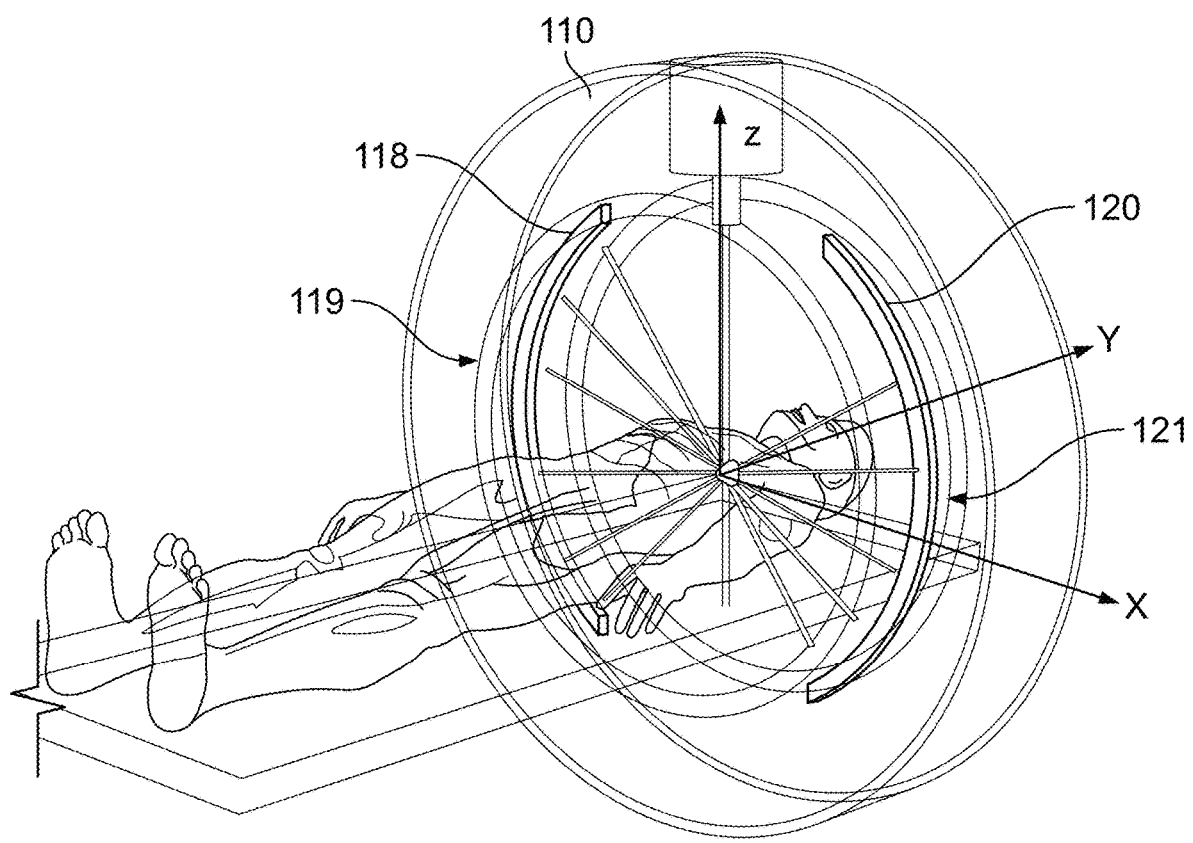

The radiation therapy system (100) may also comprise one or more PET detectors mounted on the rotating ring (110). For example, as depicted in FIG. 1C, the system (100) may comprise a first array (118) of PET detectors mounted along a first length (119) of the circumference (e.g., inner circumference) of the rotating ring and a second array (120) of PET detectors mounted along a second length (121) of the circumference (e.g., inner circumference) of the rotating ring. The first array (118) may be located directly across from (e.g., 180 degrees from) the second array. The length of the first and second arrays may be the same or may be different. In the variation in FIG. 1C, the length of the first and second arrays is the same, and each may have a length that is about 25% of the inner circumference of the rotating ring (110). The arc occupied by the first array (118) (and the second array (120)) may have an angular sweep of about 90 degrees, but may have any desired angular sweep (e.g., from about 45 degrees to about 180 degrees, about 60 degrees, about 75 degrees, about 120 degrees, about 135 degrees, about 140 degrees, about 150 degrees, about 155 degrees, etc.). In other variations, the PET detectors (118, 120) may be arranged around the entire length of circumference of the ring except for the portions of the circumference that may be occupied by the therapeutic radiation source and a MV detector located opposite the therapeutic radiation source. In some variations, one or more PET detector arrays or modules mounted on the rotatable ring may be co-planar with the radiation beam emitted by the therapeutic radiation source, and may each provide approximately 25% coverage (e.g., 50% coverage together) azimuthally such that as they rotate, they are compatible with being co-planar with the radiotherapy beamline (i.e., the PET detector arrays or modules are not located in the therapeutic beam path). That is, each array may cover about 25% of the total angular sweep of the rotatable gantry. The width of the PET detector arrays or modules (i.e., along the length of the bore) may be selected at least in part to help facilitate the acquisition and detection of PET events (e.g., emission paths). For example, the width of the PET detector arrays or modules may be between about 4 cm and about 20 cm. In some variations, the width of the PET detector arrays or modules may be about 5 cm.

Alternatively, PET detector arrays may be located on a separate ring or gantry from the therapeutic radiation source and/or MV detector. In some variations, the PET detector ring or gantry may be non-rotatable while in other variations, the PET detector ring or gantry or may be rotatable. A rotatable PET detector ring or gantry may rotate in concert or synchrony with the therapeutic radiation source ring or gantry. For example, the PET ring or gantry may be mechanically mounted to the therapeutic radiation source ring or gantry such that rotating one of the gantries causes rotation of the other. Alternatively, the PET ring or gantry may be separately rotatable from the therapeutic radiation source ring or gantry. For example, a motion controller may rotate the two gantries or rings together or separately, as may be desirable.

Optionally, in addition to a therapeutic radiation source, a radiation therapy system may comprise a kV X-ray source or imaging radiation source mounted on the rotatable ring and a kV X-ray detector also located on the rotatable ring opposite to the kV X-ray source or imaging radiation source. The radiation from the kV X-ray source or imaging radiation source may be emitted along a first plane, while the radiation from the therapeutic radiation source may be emitted along a second plane. The first plane and the second plane may not be co-planar. For example, the imaging radiation source may be mounted on a rotatable ring at a first longitudinal location of the bore or channel extending through the gantry, while the therapeutic radiation source may be mounted a rotatable ring at a second longitudinal location of the bore or channel. The rotatable ring(s) to which the imaging radiation source and the therapeutic radiation source are mounted may be the same or different rotatable rings, which may be configured to rotate together (e.g., in synchrony) or rotate independently (e.g., rotation of one gantry is separate from rotation of the other gantry). The first and second planes may be generally parallel to each other, or may be at a non-zero angle with respect to each other. In other variations, the first plane and the second plane may be co-planar. For example, the imaging radiation source may be mounted at the same longitudinal location of the bore or channel as the therapeutic radiation source. Alternatively or additionally, there may be a single X-ray source or radiation source that may be used to treat patient regions with radiation, as well as help to provide data that may be used for image or dose reconstruction. The radiation therapy system may comprise a kV detector mounted on the rotatable ring opposite the kV or imaging radiation source. Data from the kV detector may be used for registering the position of the patient within the radiation therapy system, and/or generating an anatomical image of the patient. Although the MV radiation source may be described as a therapeutic radiation source, it should be understood that data acquired as a result of irradiation from the MV radiation source may be used in the computation and generation of images and/or dose maps. The therapeutic radiation source may be any type of ionizing radiation, for example, photon radiation (e.g., X-rays and gamma rays) and/or particle radiation (e.g., electrons, protons, neutrons, carbon ions, alpha particles, and beta particles).

A radiation therapy system may comprise a controller in communication with the gantry. The controller may comprise one or more processors and one or more machine-readable memories in communication with the one or more processors. The controller may be connected to the gantry by wired or wireless communication channels. The controller may be located in the same room or bunker as the gantry, or may be located in a different room or bunker from the gantry. In some variations, the controller may be located on the gantry, and may be, for example, mounted on the stationary frame of the gantry. The controller may be configured to coordinate the movement of the couch with the rotation of the gantry (e.g., speed), activate the radiation source(s), open or close collimator leaves/jaws, detect the position of the collimator leaves/jaws, detect positron emission paths, detect MV radiation applied to the patient, compute delivered dose based on detected MV radiation data, store treatment plan data, anatomical data from other imaging modalities including, but not limited to, MRI, CT, ultrasound, etc. The transfer of data and command signals between the stationary frame and the rotating ring may be facilitated by one or more communication interfaces that are configured to continuously transmit signals while the ring is rotating. Real-time positron emission data collected by the PET detectors and/or gantry rotational data (e.g., speed) and/or gantry positional data (e.g., gantry angle) may be transmitted across the one or more communication interfaces to the controller. The controller may use such data to update the treatment plan, for example, by adjusting the rotation speed of the ring, opening or closing certain leaves of a multi-leaf collimator disposed over the therapeutic radiation source, and/or by adjusting the timing of the therapeutic radiation pulses.

Rotatable Ring and Stationary Frame

Generally, the systems described herein may comprise a gantry comprising attachment or mounting assemblies that may help to reduce the effect of vibrational and/or centripetal forces of a rapidly rotating ring (e.g., about 50 RPM, about 60 RPM, about 70 RPM) that may cause shifts in position. For example, the components mounted on a ring rotating at about 60 RPM or more may be subject to greater levels of centripetal forces than on a gantry rotating at slower speeds (e.g., about 10 RPM, about 20 RPM). The components mounted on the rotatable ring, such as the radiation source(s), various detector(s) (e.g., MV detectors, kV detectors, PET detectors), as well as the multi-leaf collimator(s), jaw(s), linac, and all supporting structures, may have a total weight on the order of about two tons. Rotating two tons on a ring having a diameter of about 1.4 meters at a speed of about 60 RPM may generate forces that may cause deflections on the ring itself, and may also generate forces that could impact the reliable functioning of the ring-mounted components. The various component and sub-systems of the radiation therapy system described herein may comprise specialized mount assemblies and/or arrangements and/or orientations to help mitigate the effect of these forces. In some variations, the gantry may also comprise motors or actuators to facilitate positional adjustments of radiation source(s) should they shift or become misaligned with other components of the radiation therapy system (e.g., multi-leaf collimator(s), jaw(s), detector(s)). While some radiation therapy systems may comprise all of the components described herein, it should be understood that some variations may comprise a subset of these components, as may be desired.

Some radiation therapy systems may comprise a continuously-rotating gantry comprising a rotatable ring and a stationary frame. The gantry may be configured to rotate 360 degrees or more in one or more directions (e.g., capable of rotating 360 degrees or more counterclockwise and/or rotating 360 degrees or more clockwise). A continuously-rotating gantry may receive its rotational force from a traditional motor and coupled drive system or from an integrated rotor and stator design. For example, a continuously-rotating gantry may comprise one or more embedded magnetic elements or inductive elements located on the rotatable ring. The stationary frame of the gantry may comprise embedded inductive elements or magnetic elements. In this arrangement, the rotatable ring may rotate with respect to the stationary frame in a similar fashion as a rotor rotates with respect to a stator of a rotary system. In order to reduce latencies from the time a lesion or target region is located to therapeutic radiation delivery, the system may rotate the therapeutic radiation source and delivery hardware at much higher speeds than traditional radiotherapy systems. A radiation therapy system may comprise rotor and stator elements that are integrated into the same structure that supports the bearings, which may help the gantry rotate several tons of hardware continuously (e.g., 360 degrees) at speeds up to about 70 RPM (e.g., at least about 50 RPM, about 60 RPM, etc.).

Figure 2:
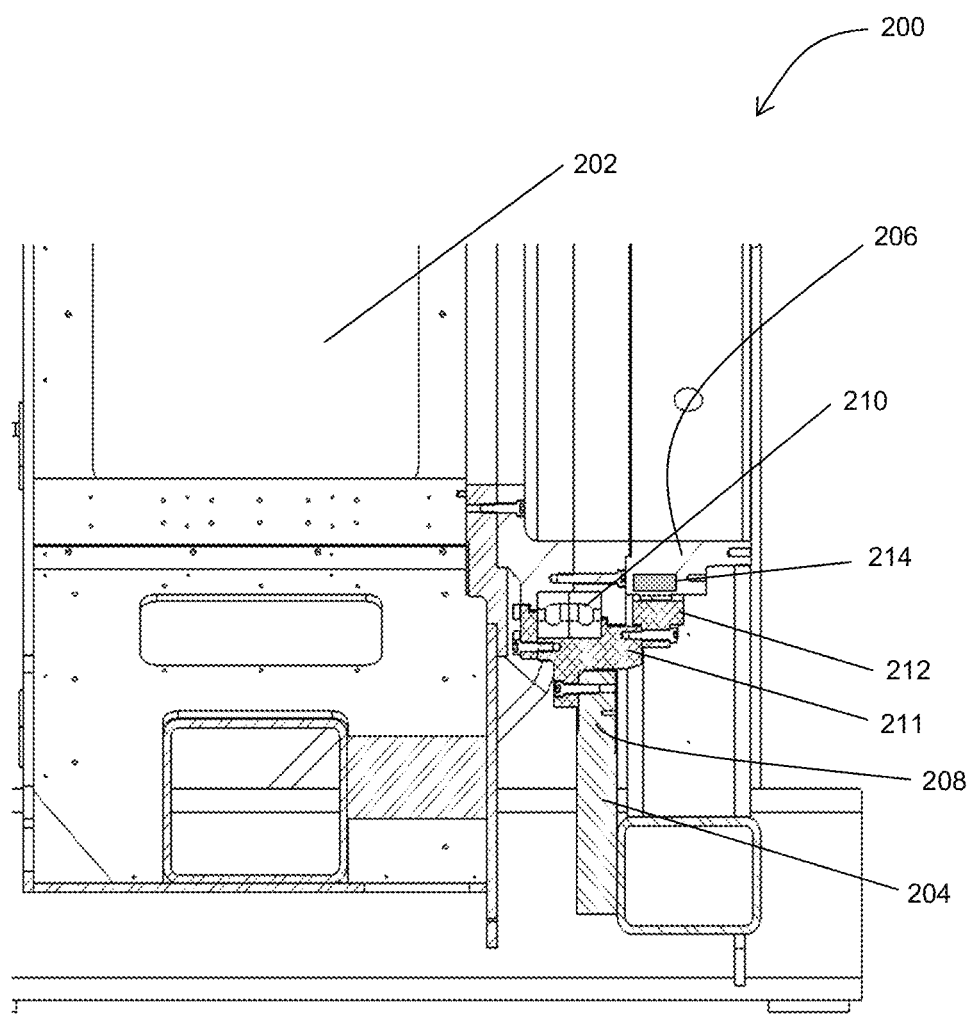
FIG. 2 is an illustrative cross-sectional view of a variation of a gantry.

FIG. 2 is a cross-sectional schematic view of one variation of a gantry (200) comprising a rotatable ring (202) and a stationary frame (204). The rotatable ring (202) may comprise an arm (206) having one or more rotor elements, which may be embedded magnetic or inductive elements (214). The rotor elements may be enclosed within a housing of the ring arm (206) or rotatable ring (202). For example, the embedded magnetic or inductive elements may comprise rare-earth magnets and/or electromagnetics and/or coils enclosed in steel. There may be a plurality of rotor elements (214) disposed around the circumference of the rotatable ring (202), for example, 3, 4, 5, 7, 8, 10, 12, 15, 19, 20, 24, 25, 28, 30, 50, 64, 75, 100, 125, 128, 135, 150, 175, 200, 256, etc. In some variations, the rotor elements (214) may be evenly distributed around the rotatable ring (202). The stationary frame (204) may comprise an arm (208) configured to rotatably engage with the ring arm (206) via a ball bearing assembly (210). The ball bearing assembly (210) may be at least partially enclosed and secured by a bearing housing or bearing plate (211). One or more stator elements or drive motors (212) may be mounted on frame arm (208) at a location that is in proximity to the enclosed or embedded rotor elements (214) on the ring arm (206), and there may be a space or gap between the drive motor and the rotor elements (e.g., a gap between the drive motor and the rotor element housing). Optionally, the drive motor (212) may be integrated or embedded within in the bearing housing or plate (211). In some variations, the motor (212) may be an inductive motor that is configured to exert a motive force on a rotatable ring with an inertia of about 3400 kg*$m^2$ from rest to about 60 RPM within about 20 seconds. Activation of the motor (212) may then induce a magnetic field in the arm (208) that applies a magnetic force on the enclosed or embedded rotor elements (214) generating a motive force to cause rotation of the rotatable ring (202). The rotation of the ring (202) with respect to the stationary frame (204) may be supported by the ball bearing assembly (210). The ball bearing assembly (210) may be located between the ring arm (206) and the frame arm (208), adjacent to the interface between the rotor elements (214) and the drive motor or stator elements (212). For example, the ball bearing housing (211) may have a recess and the ring arm (206) may have a corresponding recess, and the ball bearing assembly (210) may be located within a cavity formed by the recesses. In some variations, stator elements may comprise a plurality of individual coils that are arranged in a ring-shaped band (also depicted in FIG. 3G). The mechanical contact between the components of the ball bearing assembly (210), the ring arm (206), and the frame arm (208), may comprise one or more lubricants and/or surface modifications to reduce the friction between the components. Optionally, certain weld joints of the ball bearing assembly (210) and/or the ball bearing housing or plate (211) and/or between the frame arm (208) and the stationary frame (204) may be omitted or reduced to help reduce frame and rotating gantry deflections, which may help to improve bearing life while maintaining required structural support. Embedding or enclosing the magnetic or inductive elements (214) within a casing or housing may help to reduce the amount of stray magnetic fields that may perturb the electron beam in the linac. Increasing the number of rotor elements and/or distributing the rotor elements around the gantry may help to reduce or eliminate cogging torque, which may occur when a rotor element is not aligned with the drive motor.

The rotation of up to several tons of mass at high rotational speeds produces high levels of kinetic energy. The components mounted on the rotatable ring may be secured such that they remain attached despite the high levels of kinetic energy (e.g., so they do not pose a threat to safety). The system bearing tolerances are configured such that they reduce vibration that can lead to fasteners loosening. For example, fasteners for the components on the rotatable ring may be secured using industry practices such as bonding epoxies, torque wrenches, mechanical locking fasteners, and controlled assembly procedures. Some variations may comprise one or more accelerometers mounted on the rotatable ring, and data from the accelerometer(s) may be analyzed to detect loose fasteners or components. When the radiation therapy system is in use, rotation of the gantry may exhibit periodic accelerations that manifest from vibrations and motion, and may be measured using the one or more accelerometers. In some variations, a Fourier analysis of the acceleration data from the one or more on-board accelerometers while the gantry is rotating (e.g., during a treatment session) can be compared to baseline acceleration data. Detected differences may indicate when components on the rotatable begin to loosen, and a notification may be generated to the operator.

The structure of the rotatable ring may be configured to withstand forces and/or stresses that are generated during rotations up to about 70 RPM with deflections of about 0.5 mm or less. Rotating about two tons of mass that are located about 1.4 meters from the rotational axis at about 60 RPM can generate forces (e.g., deflection forces) and/or stresses (e.g., hoop stresses) that are orders of magnitude greater than the forces and stresses of slower rotating rings (e.g., about 10 RPM or less) or rings loaded with less mass (e.g. CT imaging rings). Traditional radiotherapy and CT imaging rings usually comprise a disk and with a bearing that is approximately co-planar with the disk. Components, such as any radiation sources, radiation detectors, image detectors, controllers, may be mounted to a front surface or plane of the disk. This may cause a cantilevered load off the surface of the disk, which may cause instabilities and/or deflections during rotation at speeds at about 60 RPM or more, especially when the disk is loaded with heavy components (e.g., radiation shields, linac, etc.).

Deflection of a disk may be approximately cubic to the thickness of the disk. Although increasing the thickness of the disk may help to increase the stiffness of the disk, components mounted to a front surface or plane of the disk may still result in instabilities during rotation at speeds of about 60 RPM or more. A rotatable ring comprising a drum structure may help address instabilities and deflections during rotation at speeds of about 60 RPM or more. A drum structure may comprise a first ring-shaped end surface or plane, a second ring-shaped end surface or plane, and lateral support or rib structures that extend along a length between the first and second ring-shaped end surfaces. The length of the lateral supporting structures may be from about 45 cm to about 95 cm, e.g., about 60 cm, about 75 cm, etc. The lateral support or rib structures may comprise a plurality of support beams, and/or brackets, and/or cage structures, and/or struts that extend between and attach to the first and second end surfaces. The lateral support structures may have mounting surfaces for the various components of the radiation therapy system. A roughly cubic relationship of deflection to thickness (which in the case of a drum, is the separation distance of the two end surfaces, or the length of the lateral support or rib structures) may provide, for example, approximately 0.001 times the deflection for a 10× separation (i.e. 60 cm separation versus 6 cm thick disk). In addition to increasing the overall stiffness of the rotatable ring (thereby reducing its deflection when fully-loaded and rotating at speeds of about 60 RPM or more), the drum structure may also allow components of the radiation therapy system to be mounted on the inner surfaces (e.g., radially-inward surfaces along lateral support structures, inner-facing surfaces of the ring-shaped end surfaces), as well as the outer surfaces (e.g., radially-outward surfaces along lateral support structures, outer-facing surfaces of the ring-shaped end surfaces) of the drum. Increasing the number of locations for mounting components by using a drum structure instead of a disk may allow the same number of components to be mounted but on a ring with a smaller outer diameter. Reducing the overall outer diameter of the rotatable ring may also reduce its overall mass and rotating inertia. The radial mounting of the components on the lateral support structures along the length of the drum may also help facilitate service of the components mounted on the ring. Rotatable rings where the components are mounted on a surface or plane of a disk may require the removal of the entire housing or enclosure(s) to access and service components mounted on the disk surface. A rotatable ring comprising a drum structure may allow access and service of the radially-mounted component via an opening and a panel (e.g., a hatch) located on a lateral side of the housing. The drum can be rotated to the access panel or hatch, and the components may be serviced or removed radially, without requiring the removal of the entire housing. Optionally, a hand-actuated brake may be provided to stop rotation of the ring or lock its position during repair or servicing.

Figure 15A:
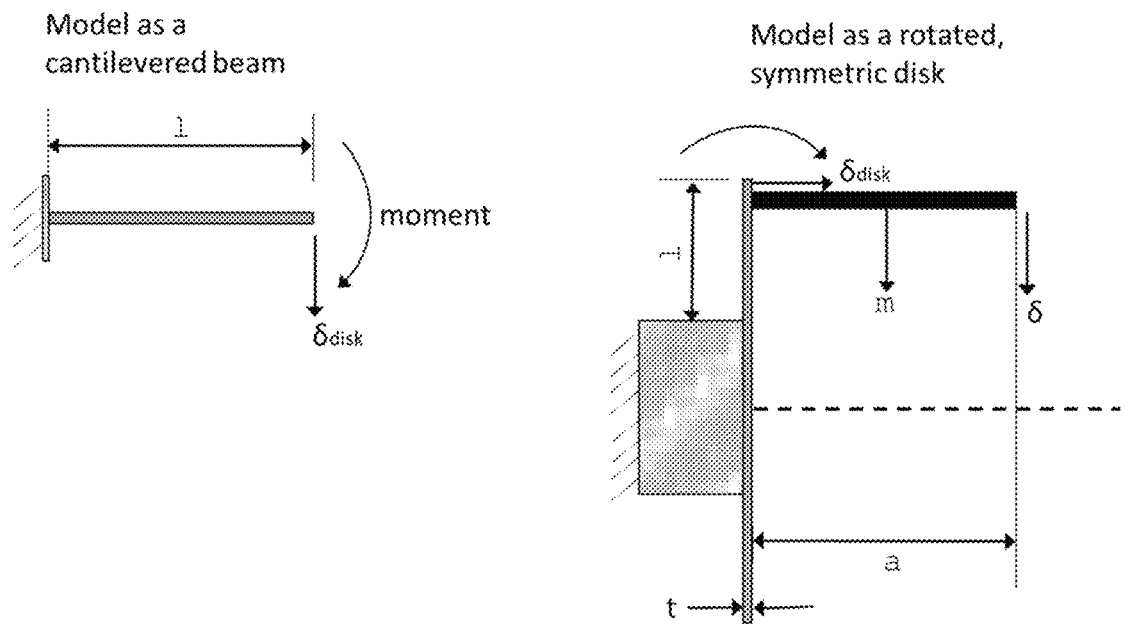
FIG. 15A diagrammatically depicts the forces sustained by a rotatable ring comprising a disk.
Figure 15B:
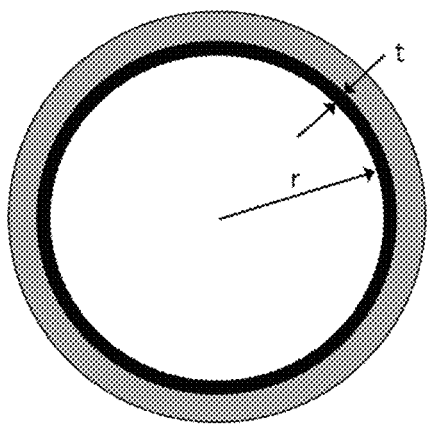
FIG. 15B diagrammatically depicts the forces sustained by a rotatable ring comprising a drum structure.
Figure 15B:
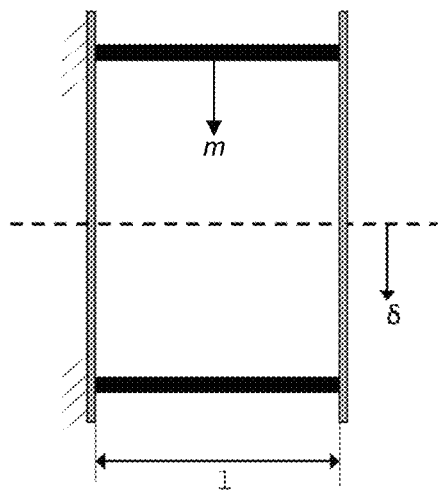

FIGS. 15A and 15B diagrammatically depict the different forces sustained by a disk and a drum structure. The deflection of a disk, δ, is approximately proportional to the mass times the length of the drum squared divided by the thickness of the drum cubed. The deflection of a disk is calculated by starting with the bending moment for a beam, as depicted in FIG. 15A.

$$\delta_{disk} = \frac{ma l^2}{4EI}$$

Where:
E=Young's Modulus
m=Total Mass
I=Moment of Inertia $$I \cong \frac{bt^3}{12}$$

Where:
b=width of section in bending which approximately equals the outside diameter of the disk.

$$\delta_{disk} \cong \frac{3ma l^2}{Ebt^3}$$

-continued $$\delta \cong \frac{3mla^2}{Ebt^3}$$

In contrast, the deflection of a drum structure, 6, may be approximately proportional to the mass times the length of the drum squared divided by the longitudinal length of the drum (i.e., the distance between the two end surfaces or planes). This may provide an advantage for the stiffness versus mass for a drum structure versus a cantilevered disk. FIG. 15B depicts the forces sustained by a drum structure having a mass mounted thereon.

$$\delta = \frac{\omega l^3}{8EI} \cong \frac{m\ l^2}{8EI}$$

Where:
E=Young's Modulus
M=Total Mass
I=Moment of Inertia $I \approx \pi r^3 t$

Where:
r=inner radius of the drum structure
t="thickness" or longitudinal length of the drum structure $$\delta \cong \frac{m\ l^2}{8E\ \pi r^3 t}$$

Figure 16A:
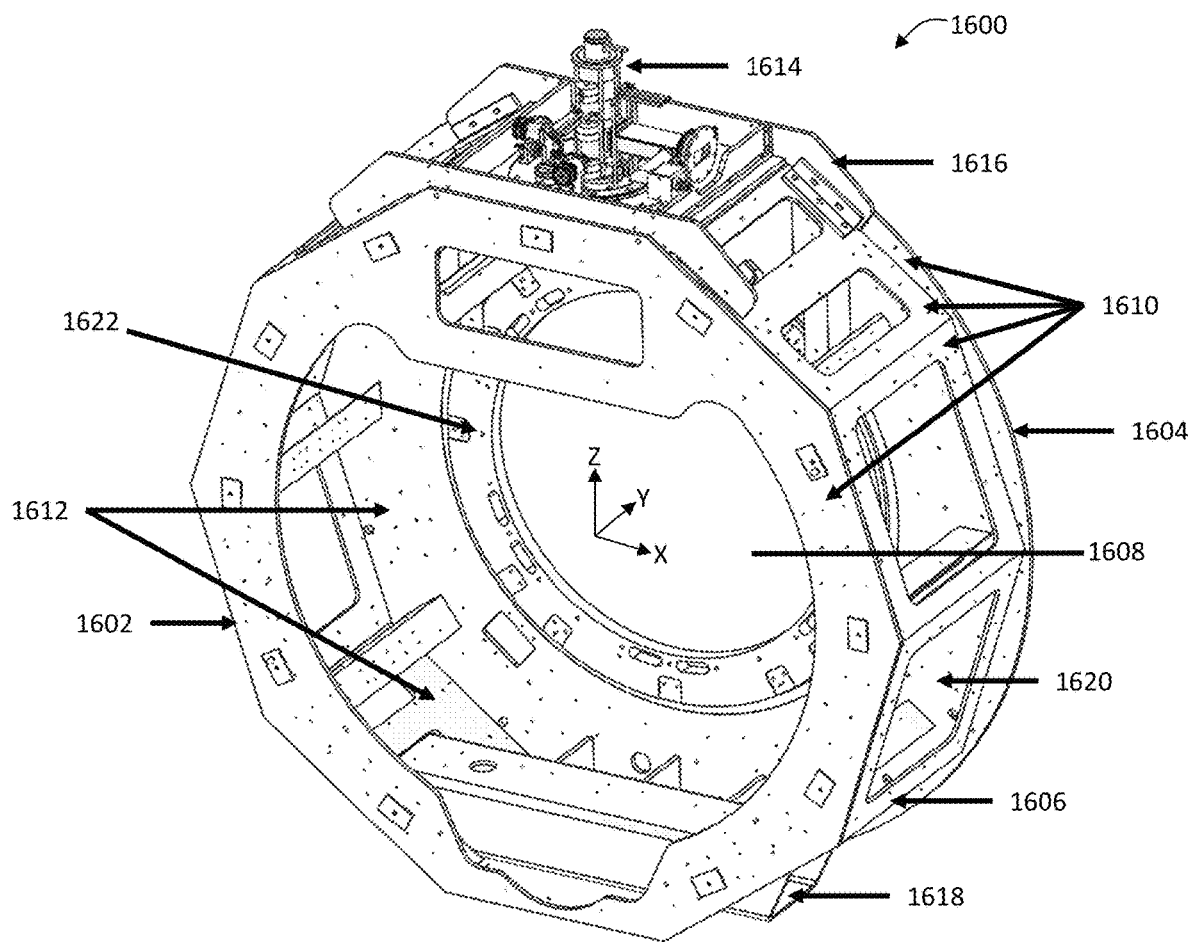
FIG. 16A depicts one variation of a rotatable gantry comprising a drum structure.
Figure 16B:
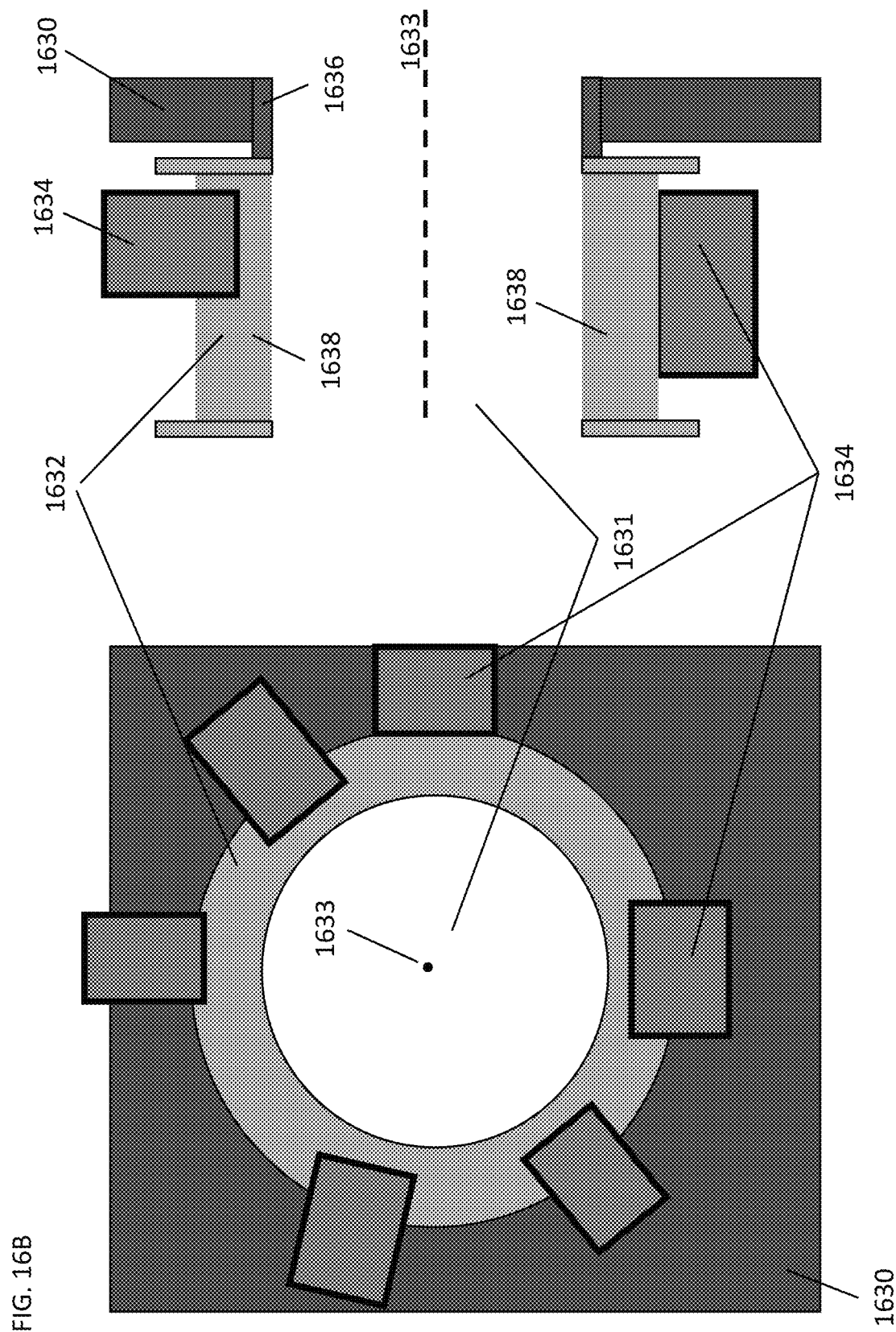
FIG. 16B depicts schematic front view (left side) and side views (right side) of one variation of a rotatable ring comprising a drum structure.
Figure 16C:
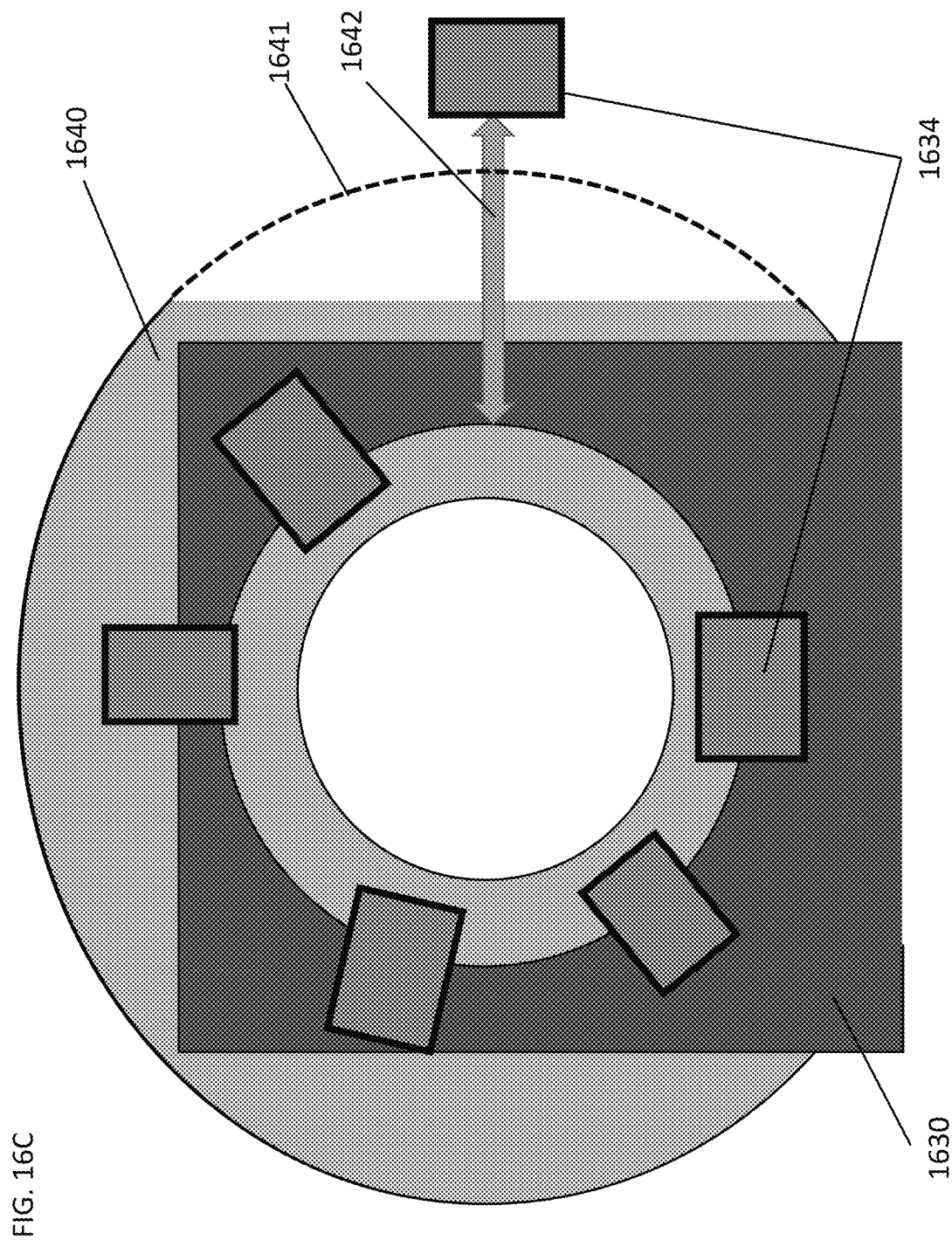
FIG. 16C depicts schematic front view of one variation of a rotatable gantry comprising a drum structure.
Figure 17A:
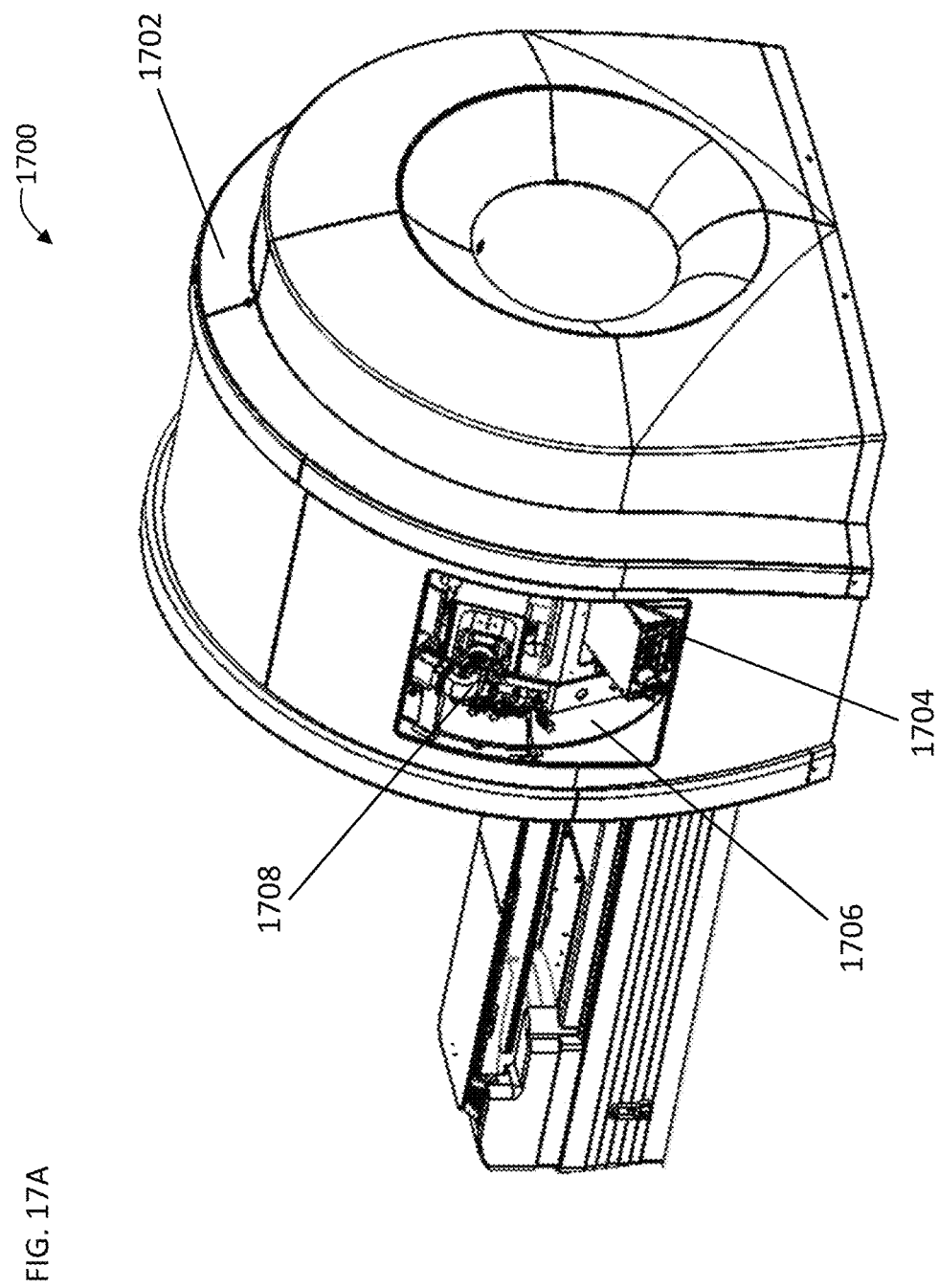
FIG. 17A depicts a rear side perspective view of one variation of a radiation therapy system.
Figure 17B:
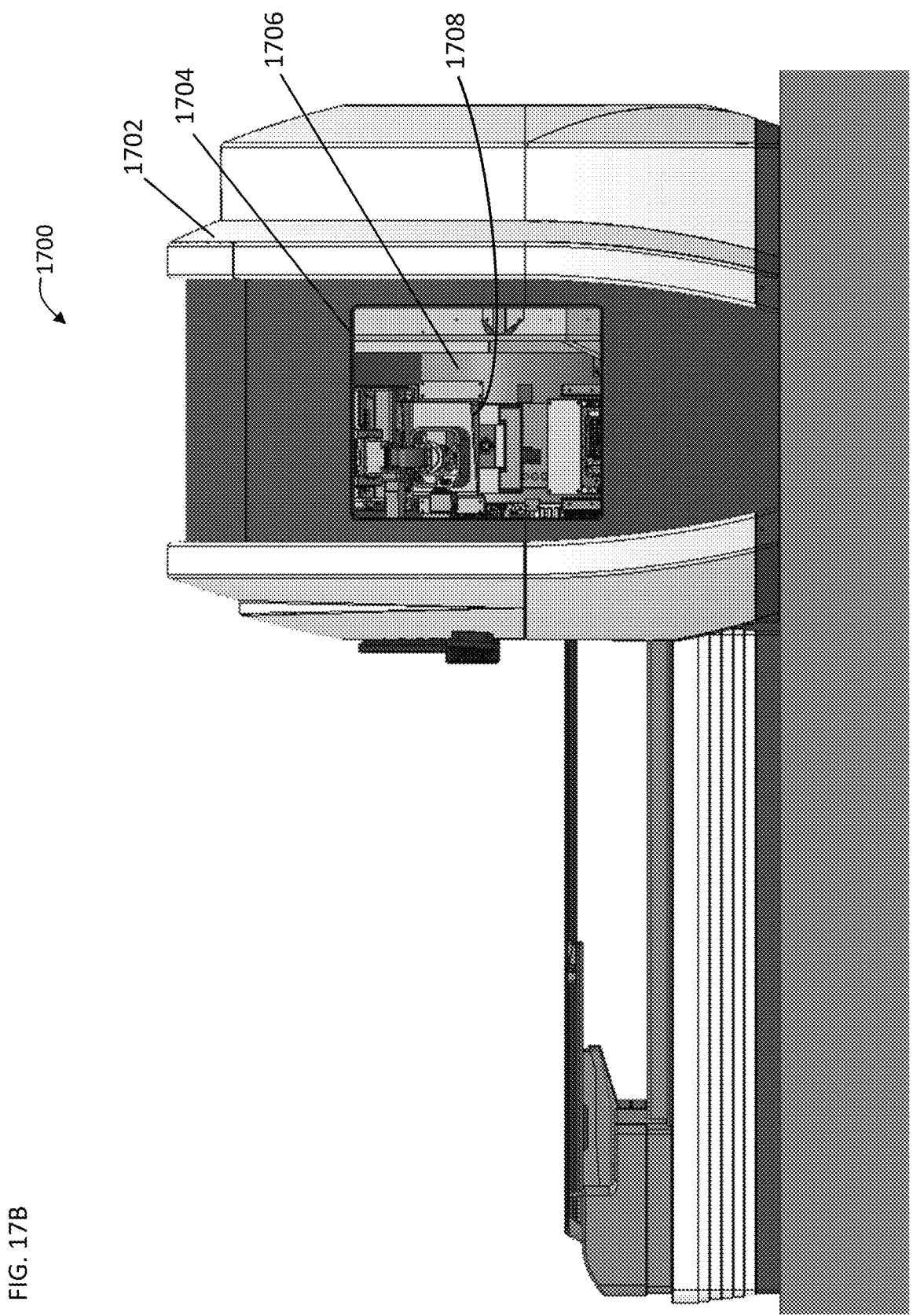
FIG. 17B depicts a side view of one variation of a radiation therapy system.

FIGS. 16A-16C depict one variation of a rotatable ring comprising a drum structure (1600). The drum structure (1600) may comprise a first end surface (1602), a second end surface (1604) opposite the first end surface, and lateral support structures (1606) disposed along a longitudinal distance or length between the first and second end surfaces. The first and second end surfaces may each comprise a ring-shaped plate with a central opening (1608). The drum structure (1600) may comprise a plurality of outer surfaces (1610) and inner surface (1612) that may be suitable for mounting various components and electronic circuits. As described previously, various components may be mounted on the rotatable ring, for example, the therapeutic radiation source, and/or PET detectors, and/or MV detector, and/or kV detector, and/or imaging systems or radiation sources, heat exchangers, etc. In some variations, larger and/or more massive components may be mounted on the lateral support structures while smaller and/or less massive components may be mounted along the first and second end surfaces or plates. As an example, FIG. 16A depicts a linac (1614) radially mounted on the lateral support beams (1606), and a radiation shield mounting assembly (1616) mounted on the lateral support beams (1606) and also along the first and second end plates (1602, 1604). A beam stop or counterweight (1618) may be mounted on the lateral support beams (1606) across from the linac (1614). The beam stop (1618) may be located under a MV detector (not shown). The second end surface or plate (1604) may comprise a plurality of recesses (1622) for ball bearings and rotor supports. The lateral support structures or beams may comprise a plurality of cutouts or openings (1620) disposed about the circumference of the drum structure (1600) for mounting components and/or to provide access pathways to service or remove/replace components. FIG. 16B is a schematic depiction of a front-view of a gantry comprising a stationary frame (1630) and a rotatable ring with a drum structure (1632) and side views of a top portion of the gantry (above the rotational axis (1633)) and a bottom portion of the gantry (below the rotational axis (1633)). Components (1634) mounted on the drum (1632) may be circumferentially disposed about a bore (1631), and the drum may be configured to rotate about the rotational axis (1633). The drum structure (1632) may be coupled to the stationary frame (1630) via a bearing (1636), e.g., ball bearings, as described above. The drum (1632) may comprise lateral support structures or beams (1638), upon which the components (1634) may be radially mounted. As depicted in FIG. 16C, the gantry may be enclosed in a housing or enclosure (1640). Mounting the components (1634) upon the lateral support beams (1638) may allow radial access (e.g., in the direction of arrow 1642) to the components. For example, the component (1634) may be moved or installed in a radial direction (1642) via a lateral access panel or hatch, which may be represented by the dotted lines (1641). FIGS. 17A-17C depict one variation of a system comprising gantry having a rotatable drum structure and a housing enclosing the gantry. The housing may comprise one or more lateral access panels or hatches. The radiation therapy system (1700) may comprise a gantry enclosed in a housing (1702) comprising a lateral access panel or hatch (1704). The gantry may comprise a rotatable ring (1706) having a drum structure as described above, and components (1708) that are radially mounted on the lateral support beams or structures. When a component on the rotatable ring needs to be serviced or replaced, the ring may be rotated such that the component is aligned with the one or more access panels or hatches. Opening the panel or hatch may allow a technician to repair or remove or install a component (e.g., by moving the component along a radial direction), without further disassembling larger portions of the housing (e.g., the front or back faces of the housing).

Figure 16D:
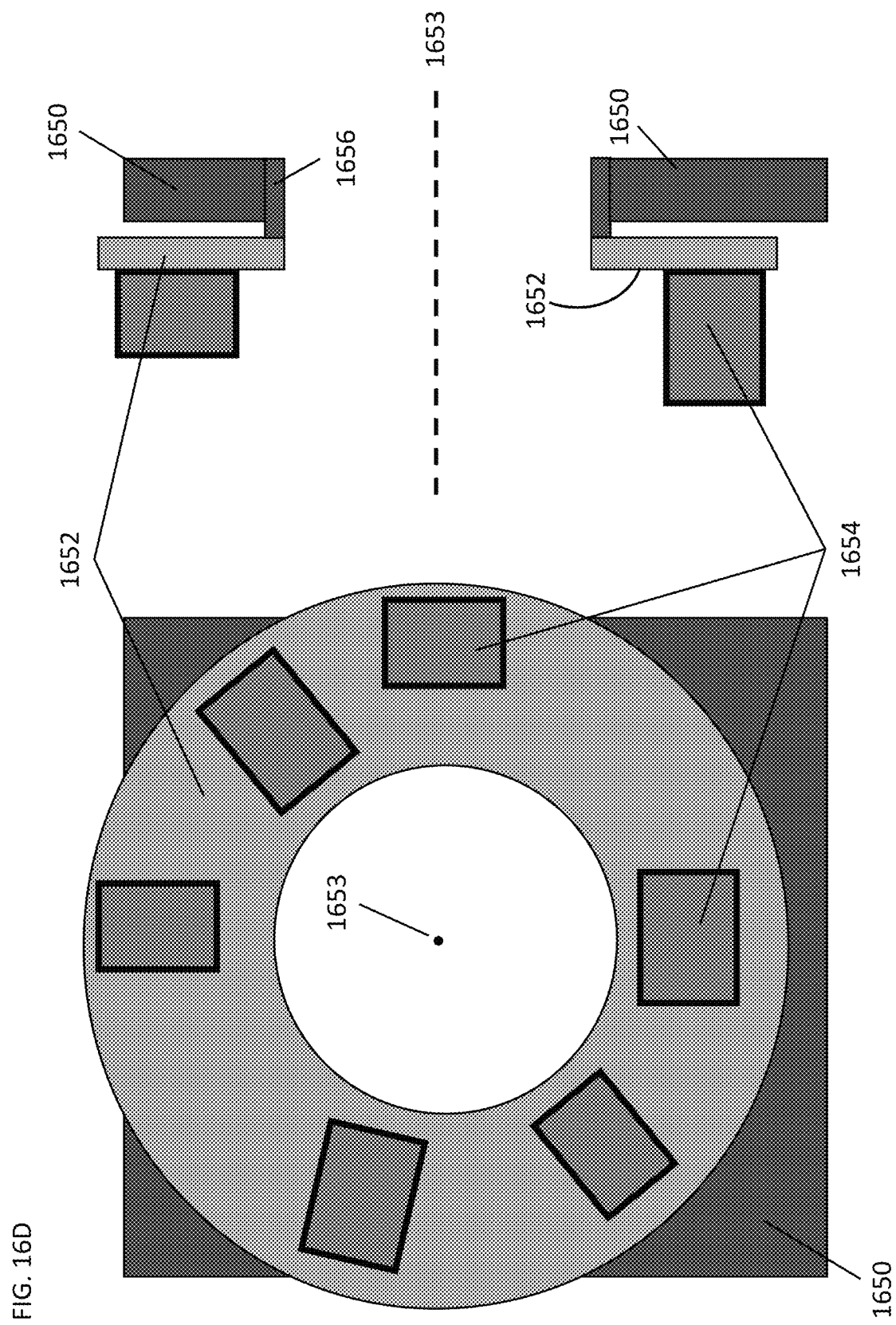
FIG. 16D depicts schematic front view (left side) and side views (right side) of one variation of a rotatable ring comprising a disk.
Figure 16E:
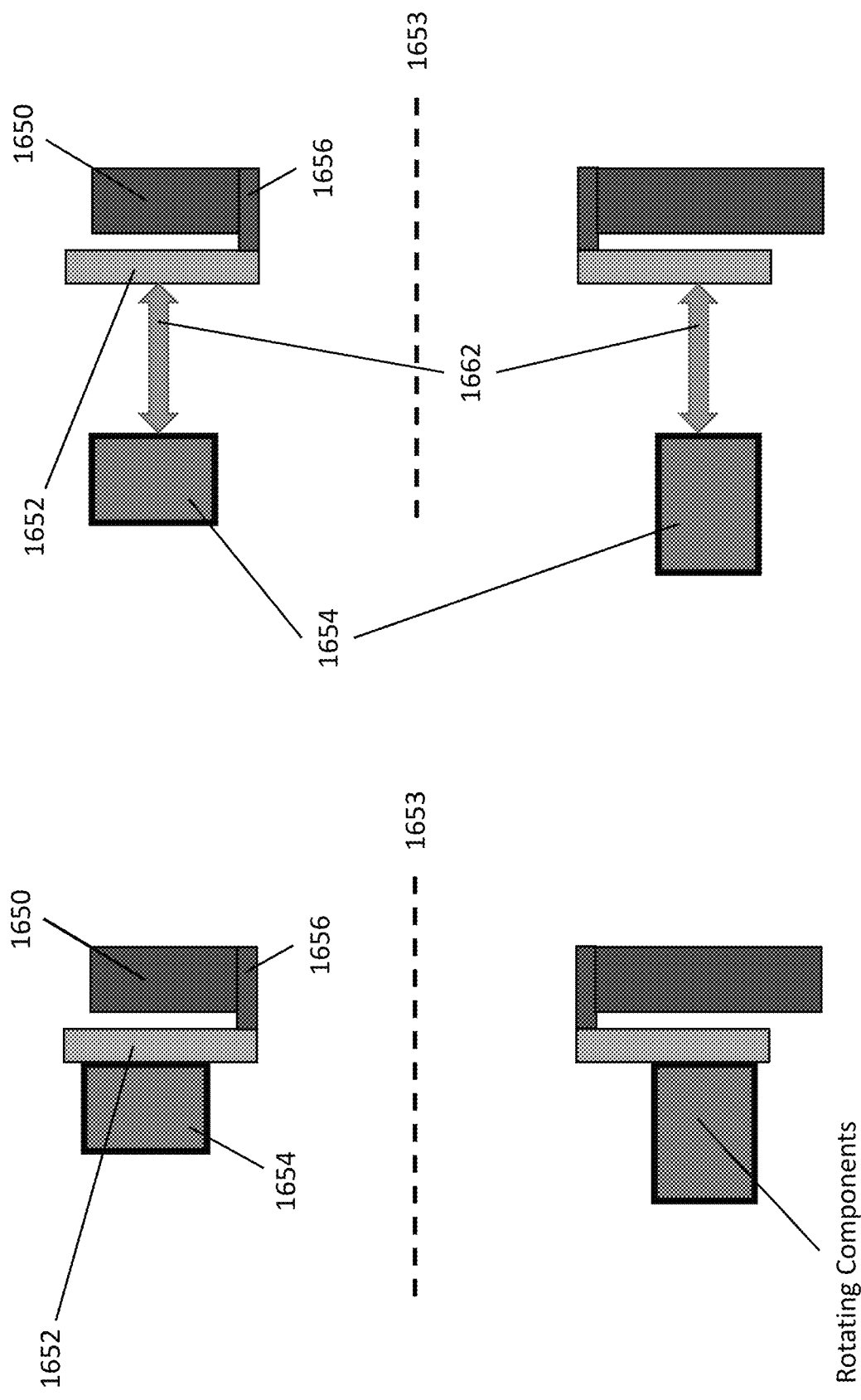
FIG. 16E depicts schematic side views of one variation of a rotatable gantry comprising a disk.

FIGS. 16D-16E depict one variation of a gantry comprising a rotatable ring comprising a disk. In contrast to a rotatable ring comprising a drum structure (as depicted in FIGS. 16A-16C), the components are mounted onto the front surface of the disk, and are not mounted in a radial direction. FIG. 16D is a schematic depiction of a front-view of a gantry comprising a stationary frame (1650) and a rotatable ring with a disk (1652), and side views of a top portion of the gantry (above the rotational axis (1653)) and a bottom portion of the gantry (below the rotational axis (1653)). Components (1654) may be mounted on a front surface of the disk (1652), and the disk may be configured to rotate about the rotational axis (1653). The disk (1652) may be coupled to the stationary frame (1650) via a bearing (1656), e.g., ball bearings, as described above. As depicted in FIG. 16E, mounting the components (1654) on the front face or surface of the disk takes place along a direction that is perpendicular to the face of the disk, as indicated by the direction of arrow 1642). That is, the components (1654) may be installed or removed in a direction that is orthogonal to the radius of the disk. In some variations, access to components (1654) through a gantry housing may be provided through a front or back face of the housing, and not from the lateral sides of the housing. This may involve disassembling substantial portion of the front and/or back face of the housing in order to service, install, and/or replace components mounted on the disk (1652).

Communication Interface

Generally, the systems described here may comprise a data interface to facilitate continuous and rapid transfer of data and command signals. The data interface may be provided between the rotatable portion and the stationary portions of the gantry and may comprise motion-independent communication interfaces that transfer data between the rotatable and stationary portions while the rotatable portion is rotating. In some variations, a radiation therapy system may comprise one or more signal transfer or communication interfaces between the components mounted on the rotatable ring and a controller that is not located on the rotatable ring (e.g., mounted to the stationary frame, and/or in communication with the stationary frame). The types of signals and data transferred between the rotatable and stationary portions of the radiation therapy system may comprise operational command signals (e.g., from the controller to the linac to fire radiation pulses or to the multi-leaf collimator to open or close certain leaves), positron emission data from the PET detectors, radiation data from the MV detector and/or kV detector, as well as positional data of the components on the rotatable ring (e.g., rotation speed, linac location/gantry angle/firing position or index, position of the collimator leaves, jaws, etc.) and system status data (e.g., temperature, ambient radiation levels, etc.).

In one variation, a radiation therapy system may comprise a combined static and rotating/dynamic gantry communication interface to accommodate a relatively fast (e.g., 60 RPM) continuously-rotating gantry, while maintaining high angular precision for capturing PET data and delivering radiation. A radiation therapy system comprising a fast, rotatable gantry may comprise a slip ring-based communications interface or linkage. That is, in order to correctly latch angular position to each detected PET event (or radiation delivery angle), the time delay between the detection or measurement of the position of the PET detectors and the detection or measurement of PET events should be reduced.

In many radiation therapy systems, the inherent time lag for position information from a static read head coming across a slip-ring based communication link is too great for the desired temporal precision, and may result in unacceptable treatment accuracy. Contact slip rings (which are often used) are not ideal for use in rapidly-rotating gantry systems (e.g., 60 RPM or more), since the rapid rotation may expedite the wear and tear on the contacting components and compromise the data connection and signal integrity.

A rotating and stationary encoder may help to facilitate timely and rapid transfer of system feedback to the controller so that PET data may be precisely linked with the location of where that PET data was collected, and so the linac and collimator may be activated when rotated to the desired gantry angle or firing position. Additionally, positional data feedback of the drive motor and/or controller regarding the rotation speed may help to maintain a desired (which may be steady or varied) rotation speed within a specified motion error. System status data that is consistently and rapidly transferred to the system controller may help to timely identify any failures (even single points of failure) in the system before such failures escalate into safety hazards or substantial system damage. Furthermore, precise synchronization across stationary and rotating components may help to regulate gantry rotation with respect to linac firing.

To accommodate rapid and robust transfer of data, the radiation therapy systems described herein may comprise two or more independent communication interfaces that provide redundant feedback data for verification of gantry rotation and signal synchronization (e.g., dual feedback communication channels). This data may help the controller to rapidly and accurately detect when any system component deviates from a desired standard or tolerance, to generate the appropriate notification(s) to the operator, and/or to automatically generate diagnostic and/or repair commands to correct such deviations. In some variations, the feedback data from two or more communication interfaces may be continuously compared and monitored for any timing deviations that exceed a prescribed tolerance. For example, angular alignment data transmitted across two feedback data channels may be compared and monitored at regular intervals (e.g., at frequencies from about 500 Hz to about 2000 Hz, about 1000 Hz) to help ensure that the rotating ring and the stationary frame are precisely aligned. In some variations, the two or more independent communication interfaces have separate read heads (e.g., receiver elements) and separate encoders (e.g., transmitter elements). In one variation, a first communication interface may comprise a first read head mounted on the rotatable ring of the gantry, where the first read head is in communication with a first position sensor that is also mounted on the rotatable ring, and a second communication interface may comprise a second read head mounted on the stationary frame, where the second read head is in communication with a second position sensor that is also mounted on the stationary frame. The first and second position sensors may be magnetic and measure incremental position around the gantry (e.g., relative position between the rotatable ring and the stationary frame). In one variation, the rotatable ring and the stationary frame may each have index marks spaced at about 15 to about 18 degrees intervals around their circumference, which may allow the first and second position sensors to identify the angular or rotational location of the rotatable ring relative to the stationary frame. As the first position sensor moves across an index marker on the stationary frame (and/or as an index marker on the rotatable ring moves across the second position sensor), the first position sensor may output a first index signal (and/or the second position sensor may output a second index signal). The absolute position of the rotatable ring may be computed by the controller after the ring has rotated through at least two index markers. Additionally or alternatively, the first and second position sensors may each output a signal that represents the rotary or angular position of the rotatable ring with respect to the stationary frame. In one variation, the stationary frame and the rotatable ring may each comprise a plurality of locator marks and a plurality of counts located between the locator marks. The number of counts between locator marks of a rotatable ring may be different from the number of counts between locator marks of a stationary frame. Locator marks and counts may comprise a strip of magnetic and/or metallic material that is detectable by a sensor (e.g., a read head or receiver unit) on the rotatable ring and/or stationary frame (e.g., a magnetic flux may induce a current in the sensor as it moves past the locator mark or count). A plurality of locator marks distributed around the circumference of the rotatable ring or stationary frame may comprise an encoder strip. In some variations, a system may comprise a first encoder strip on an outer circumference of a slip ring rotor, and a second encoder strip on the outer circumference of a slip ring stator. The encoder strips may be flat bands that are built into the structure (e.g., located within a recess of a rotatable ring and/or stationary frame) so that a receiver or sensor can detect information as it sweeps over the encoder strip. For example, a rotatable ring may comprise a feedback or encoder strip comprising 22 locator marks and 114,400 counts, and a stationary frame may comprise a feedback or encoder strip comprising 20 locator marks and 136,000 counts. By having locator marks that are differently or uniquely spaced by counts, the location of the rotatable ring may be identified after a sensor or receiver unit of the rotatable ring and/or stationary frame has swept over two consecutive locator marks on the stationary frame and/or rotatable ring. Each set of counts between the locator marks may be associated with a specific arc length of the 360 degree rotation. In some variations, as a safety feature, the feedback strips may be uniquely patterned with different numbers of counts between the locator marks to allow for independent confirmation of the rotatable ring location.

The function of the first and second position sensors may be monitored to help ensure that the position of the rotatable ring is accurately measured. If the precision or accuracy of one or both of the position sensors falls outside of a prescribed tolerance, an error or fault signal may be generated, indicating to the operator that one or both of the position sensors has failed. One method of evaluating the functionality of the position sensors may comprise comparing the derivative of a position sensor signal (e.g., a signal representing the rotary or angular position of the rotatable ring) over time. This may help facilitate a faster, more robust indication of a problem or fault of one of the position sensors. The derivative may be generated by several methods including first difference equations, digital filters, Kalman estimators, or utilizing other estimation techniques. In one example, data from the position sensors indicative of the rotary or angular position of the rotatable ring is transmitted to a system controller. A controller processor may then compute the derivative of the rotary or angular position signal for each of the position sensors by any appropriate method, such as first difference equations, digital filters, Kalman estimators, or utilizing other estimation techniques. The computed derivatives from each position sensor may be compared, and if the difference between the computed derivatives of the two position sensors exceeds an error threshold, the processor may then generate a signal indicating that one or both of the position sensors need to be checked, repaired, or replaced. In some variations, the error threshold may be a difference in the derived rotation speed between the first and second position sensors of about 0.5 RPM, and/or a difference in computed rotary or angular position of the rotatable ring or the derivative of the rotary or angular position signal of about 0.5 degrees. The data output from the position sensors may be continuously monitored and compared, and in some variations, may be polled and compared at a frequency from about 500 Hz to about 2000 Hz, e.g., about 600 Hz, about 750 Hz, about 900 Hz, about 1000 Hz, about 1400 Hz, about 1500 Hz, etc. The data output from the position sensors may be polled and compared from about 12 to about 100 times per gantry rotation, e.g., about 20 times per rotation, about 24 times per rotation, about 25 times per rotation, about 50 times per rotation, about 65 times per rotation, about 75 times per rotation, about 80 times per rotation, about 90 times per rotation, about 100 times per rotation, etc.

In some variations, a synchronization check between two or more communication interfaces may occur whenever the gantry rotates through a particular gantry angle (e.g., whenever the linac location on the gantry rotates through gantry angle 180 or the bottom of the gantry). Alternatively or additionally, a synchronization check may occur at particular time intervals or frequencies. For example, synchronization between the rotating phase (e.g., rotatable ring and all components mounted thereon) and the stationary phase (e.g., stationary frame and all components mounted thereon or coupled thereto) of the radiation therapy system may occur about every 0.1 second or at about 1 kHz. In some variations, synchronization across communication interfaces or channels may comprise transmitting only the data that is different between the channels, i.e., offset data. Offset data may be used, for example, to autocorrect differences between the position sensors. In some variations, the first read head (i.e., the rotatable read head) may be located at or near the circumferential position of the linac, or about 180 degrees from the linac (e.g., opposite or across from the linac) and the second read head (i.e., the stationary read head) may be located at the 9 o'clock position of the stationary frame when viewed from the front (couch side) of the gantry. In other variations the first and second read heads may be located at any circumferential position along the rotatable ring and stationary frame, respectively, as may be desired.

In one variation, a rotating ring may comprise a slip ring assembly that comprises a plurality of concentric power rings and data signal rings. For example, a slip ring assembly may comprise six power rings and six data signal rings. The power rings and data rings may be concentric and have the same axis of rotation. The power rings may comprise an inner set of rings that transfer power between the rotating ring and stationary frame via power brush blocks (e.g., two power brush blocks). The data signal rings may comprise an outer set of rings that transfer information between the rotating ring and stationary frame via one or more data brush blocks. The brush blocks that contact the power rings and/or the data rings may comprise metal-graphite brush tips. Examples of data signals transmitted between the rotatable ring and stationary frame via data brush blocks may include synchronization signals and/or timing or data offset signals. Alternatively or additionally, data signals transmitted between the rotatable ring and stationary frame may be transmitted via contactless links, including wireless communication or capacitive links. Wireless communication links may use a custom or recognized protocol such as IEEE 802.11b, and may comprise one or more rotating and one or more stationary antennas that receive (e.g., receivers or read heads) and/or transmit (e.g., transmitter elements) data signals. Capacitive links may include two separate links: one for transmitting signals from the stationary frame to the rotatable ring, and one for transmitting signals from the rotatable ring to the stationary frame. In some variations, a contactless data and/or power transmission link may comprise platter-integrated emitting structures, such as one or more GIGACAP® stators and one or more GIGACAP® rotors mounted on the stationary frame and/or rotatable ring. Examples of data signals transmitted between the rotatable ring and stationary frame via contactless mechanisms may include image data (e.g., PET detector data, MV detector data, and/or kV detector data), and/or synchronization signals and/or timing or data offset signals.

Figure 3A:
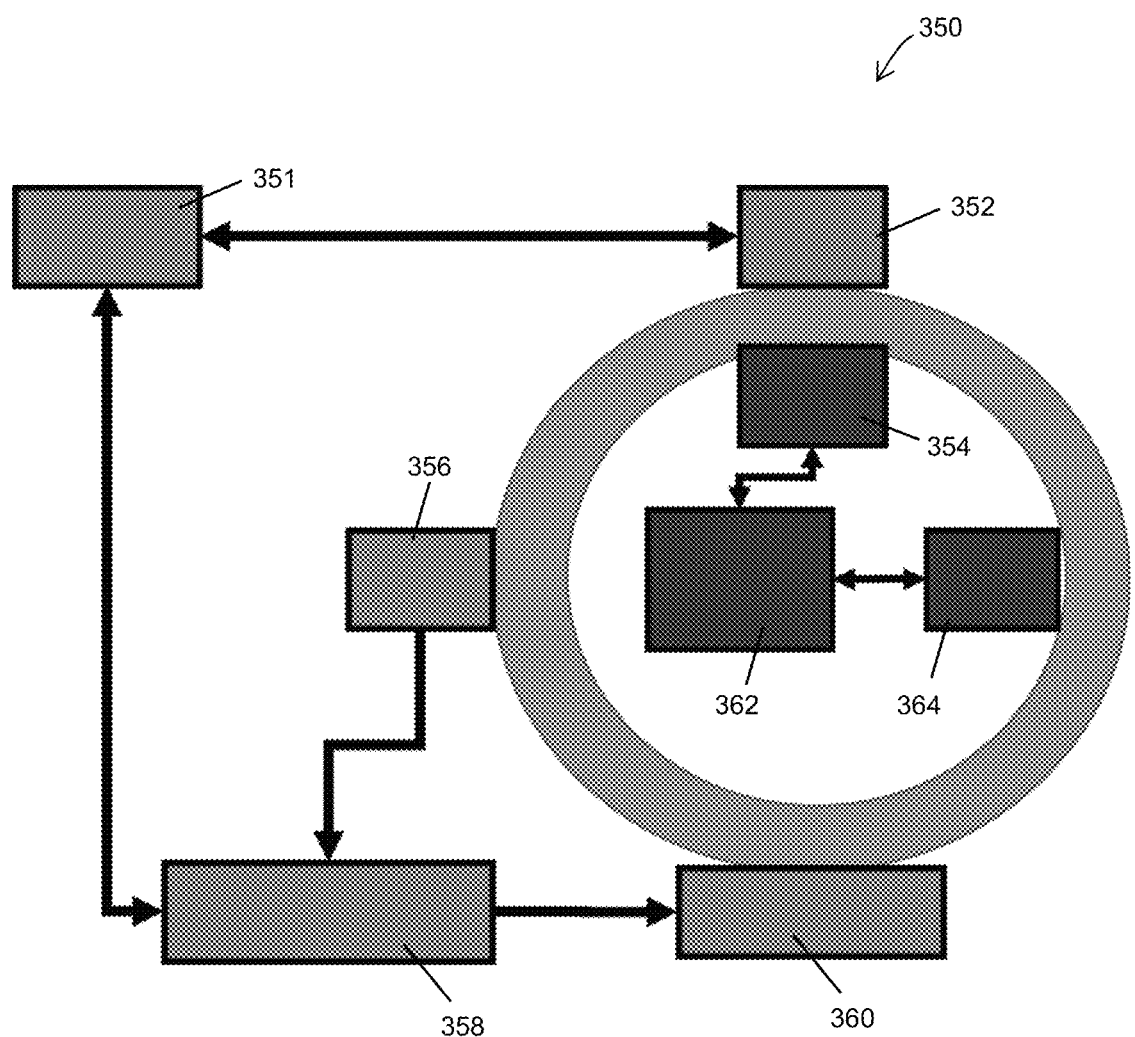
FIG. 3A is a block diagram representation of one variation of a communication interface that may be used in a radiation therapy system.

FIG. 3A depicts a block diagram representation of one variation of a communication interface that may be used in a radiation therapy system comprising a rotatable gantry having a rotatable ring and a stationary frame. The communication interface may comprise a stationary communication link (352) located on the stationary frame and a rotatable communication link (353) located on the rotatable ring. Signals may be transferred between the stationary frame and the rotatable ring via the stationary and rotatable communication links. The communication links may transmit signals wirelessly and/or via brush blocks. The stationary frame may comprise a stationary controller (351) comprising a processor in communication with the stationary communication link (352), stationary encoder (356), a gantry drive controller (358), and a gantry drive motor (360). The gantry drive controller (358) may be in communication with the stationary controller (351), the stationary encoder (356) and the gantry drive motor (360). The rotatable ring may comprise a rotatable controller (362) comprising a processor, and rotatable encoder (364). The rotatable controller (362) may be in communication with the rotatable communication link (354) and the rotatable encoder (364). The rotatable and stationary encoders may operate independently, and their encoder data (e.g., rotatable ring location data) may be checked against each other periodically via signals transferred across the communication links (352, 354). The rotatable encoder and/or the rotatable controller data may be the reference against which the stationary encoder and stationary controller are compared (e.g., the rotatable controller is the "master" while the stationary controller is the "slave"). In some variations, the rotatable controller (362) generates commands for radiation delivery components (e.g., therapeutic radiation source commands, multi-leaf collimator commands, etc.) based on the rotatable ring position data from the rotatable encoder (364). The rotatable controller (362) may read and timestamp data from the rotatable encoder (364), and/or PET detectors and/or a CT imaging system that are mounted to the rotatable ring. The controller (362) may timestamp data acquired from components on the rotatable ring at a rate of about 0.5 kHz or more (e.g., about 1 kHz, about 1.5 kHz, etc.). The timing of commands for the radiation delivery components and synchronization may be determined based on the gantry angle derived from rotatable encoder data. In some variations, the operation of the gantry drive motor (360) may be based on the data from the stationary encoder (356). For example, ring position and/or velocity data from the stationary encoder (356) may be communicated to the gantry drive controller (358). The gantry drive controller (358) may also receive commands from the stationary controller (351) and generate commands and instructions to the gantry drive motor (360). The gantry drive controller (358) may timestamp the data from the stationary encoder (356) at a rate of about 250 Hz, and the timestamped encoder data may be transmitted to the rotatable controller (362) via the rotatable communication link (354) where it may be compared against timestamped rotatable encoder data for accuracy. Optionally, a couch position encoder may also provide timestamped couch position and/or velocity data to the rotatable controller via the rotatable communication link.

Figure 3B:
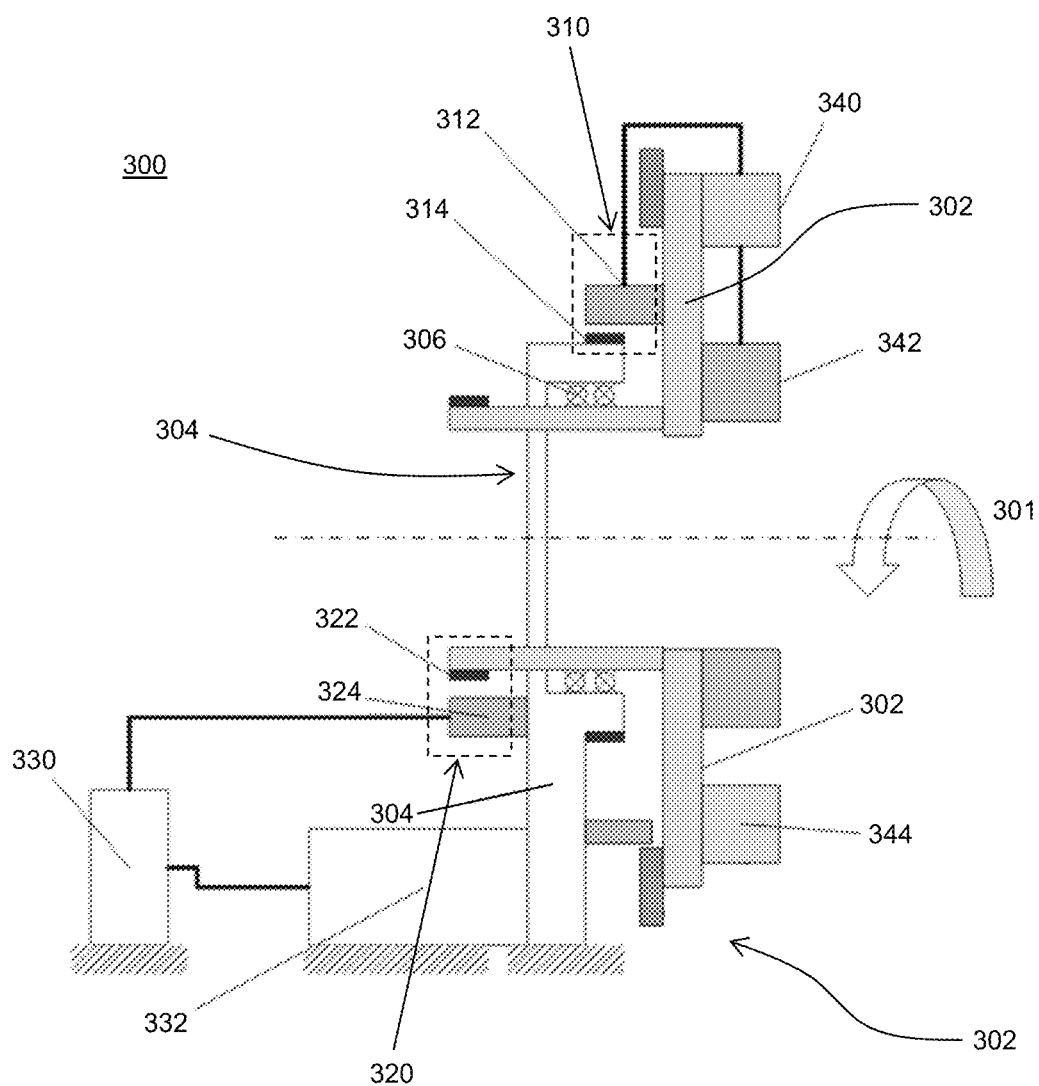
FIG. 3B is a cross-sectional view of a variation of the gantry.

FIG. 3B depicts a schematic cross-sectional view of one variation of a communication interface or slip-ring linkage that may be used in a radiation therapy system comprising a rotatable gantry. The rotatable gantry (300) may be a circular gantry comprising a rotatable ring (302) and a stationary frame (304). The rotatable ring (302) may be coupled to the frame (304) via gantry bearings (306), and may be configured to rotate about an axis of rotation, represented by dotted line (301). A first communication interface (310) may comprise a rotating receiver element (312) mounted to the rotatable ring (302) and a static transmitter element (314) mounted to the stationary frame (304) and configured to transfer command signals from a non-rotating motion controller (330) to the rotatable components. For example, a command signal representing controller instructions for linac firing and multi-leaf collimator operation (e.g., opening and/or closing of certain leaves) may be transferred from a stationary controller to the static transmitter element (314) to the rotating receiver element (310). A second communication interface (320) may comprise a rotating transmitter element (322) mounted to the rotatable ring (302) and a static receiver element (324) mounted to the stationary frame (304). The rotating transmitter element (322) may be configured to transfer data signals from the rotatable components to the non-rotating controller (330). For example, data signals representing positional information of the linac, positional information of collimator leaves, measured rotation speed data of the rotatable ring, PET detector data, MV detector data and/or kV detector data, etc. may be transferred from the rotating ring (302) to the stationary motion controller (330) and/or a stationary controller. Some of this data may be transmitted to a controller on the rotatable ring that generate commands for gantry rotation and collimator leaf actuation to adjust for any system deviations or shifts (e.g., positional drifts of any of these components), as well as to coordinate the timing of firing radiation pulses with linac location with collimator leaf configurations. The transmitter and receiver elements of the first and second communication interfaces may communicate commands and/or data using inductive and/or capacitive signal transfer methods.

Figure 3C:
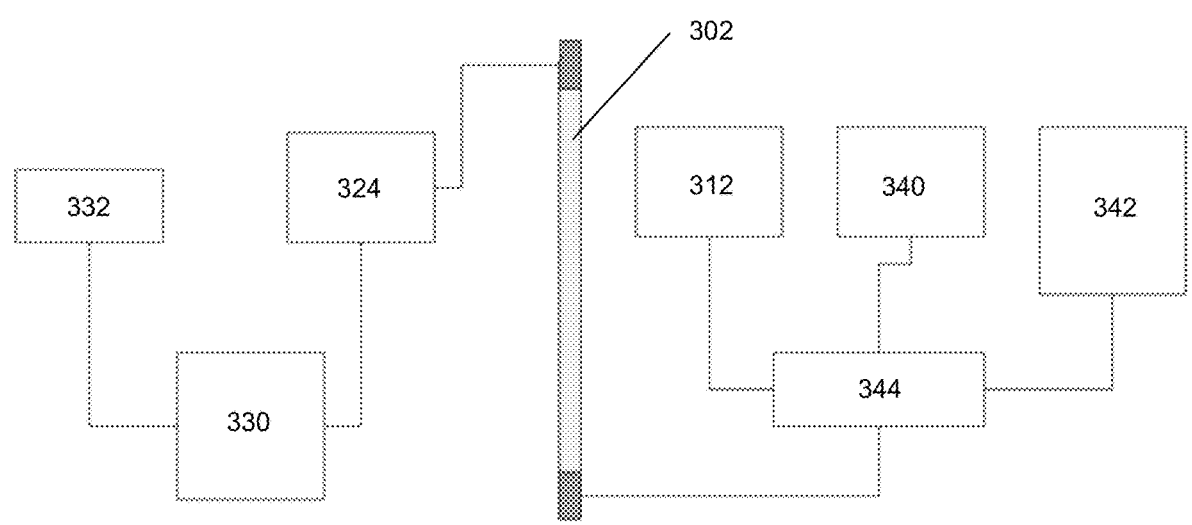
FIG. 3C is a block diagram of the gantry.

FIG. 3C is a functional block diagram that depicts the flow of data between stationary or static components of a gantry and rotatable or dynamic components of the gantry. The static feedback is the precise, low-latency position data on the stationary side. The stationary high-bandwidth data in this subsystem, such as the position and/or velocity of the rotatable ring, may be detected by the stationary read head (324) or stationary encoder, and transmitted to the stationary motor controller (330) and motor (332). The operation of the motor controller and motor may not rely on data signals transmitted across the slip ring. The rotating high-bandwidth data in this subsystem, such as the position and/or velocity of the rotatable ring, may be detected by the rotating read head (312) or rotatable encoder, and transmitted to other modules on the rotatable ring, such as the radiation delivery module (340), PET detectors (340) and other electronics (344). The signals that are transmitted across the slip ring may include a relatively low-latency signal, such as a synchronization signal, data from the rotatable PET detectors (342) and MV detectors (not shown). These signals may be transmitted across the slip ring to the motion controller (330), which may help better regulate the control of the motor (332) that drives the rotatable ring (302). Multi-leaf collimator and linac firing commands generated by a system controller (not shown) (e.g., based on treatment plans and/or feedback data from the PET detectors and/or MV detectors) may be transmitted from the system controller to the rotating collimator and linac. Angular location of the linac, collimator, and PET detectors may be tracked by the system controller. The latency between the detection of a positron emission event and the application of a therapeutic radiation pulse may contribute to inaccuracies in treatment, since a delay of several seconds may hinder the ability of the system to apply radiation treatment before tumor movement. Synchronizing location data of the PET detectors, linac and collimators and reducing the latency of the data transfer between these components and the system controller may help to facilitate more precise application of therapeutic beams (that is, the linac emits therapeutic beams at the specified gantry angles at the specified time points).

Figure 3E:
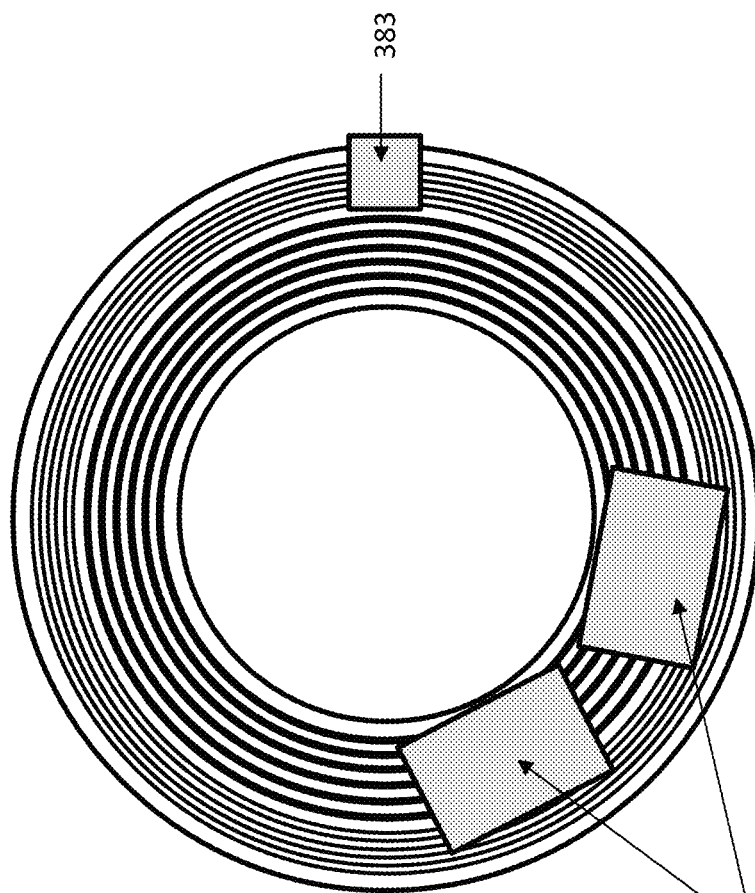
FIG. 3E depicts a front view of a slip-ring for a variation of a gantry.
Figure 3D:
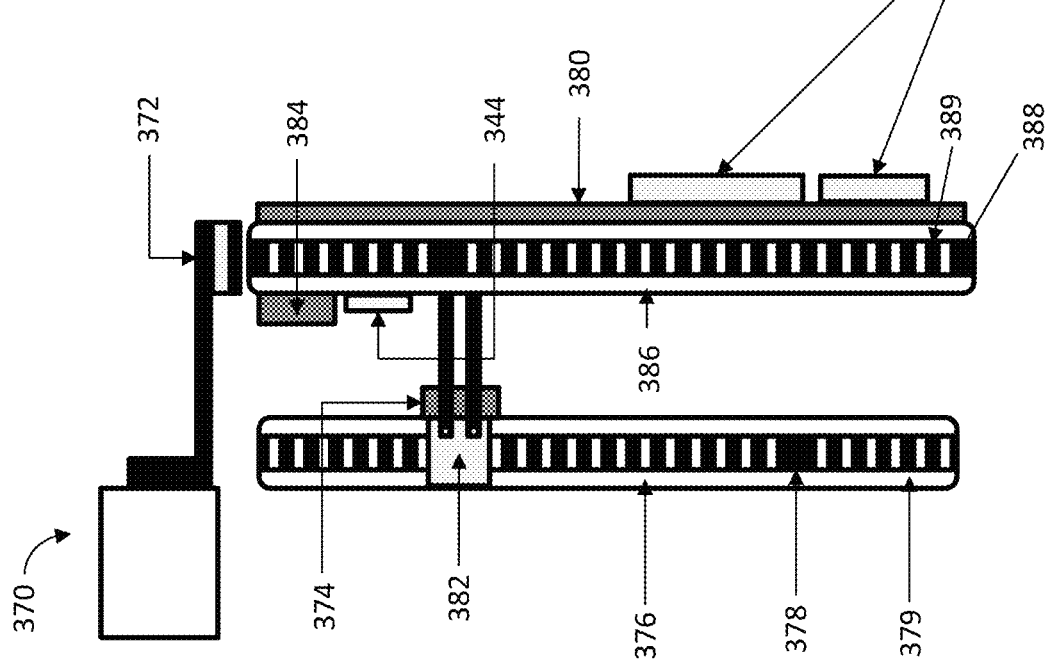
FIG. 3D depicts a schematic side view of a variation of a gantry.

FIGS. 3D-3F depict one variation of a communication interface across a slip ring between a stationary frame and a rotatable ring. The stationary frame (370) may comprise a stationary receiver unit (372), a stationary transmitter unit (374), and a stator ring (376). The stator ring (376) may comprise a plurality of locator marks (378) and counts (379) between the locator marks (378). The rotatable ring (380) may comprise a rotatable receiver unit (382), a rotatable transmitter unit (384), and a rotor ring (386). The rotor ring (386) may comprise a plurality of locator marks (388) and counts (389) between the locator marks (388). The number of counts between the locator marks of the stator ring may be different from the number of counts between the locator marks of the rotor ring. The stator ring and rotor ring may have from about 10 locator marks to about 50 locator marks each, with about 100,000 counts to about 200,000 counts each. For example, the stator ring may comprise 20 locator marks and 136,000 counts and the rotor ring may comprise 22 locator marks and 114,400 counts. The receiver units may comprise a capacitive or inductive sensor configured to detect the locator marks and counts as the receiver units move over the locator marks and counts. The rotatable receiver unit (382) may comprise an encoder, and as the rotatable receiver unit sweeps across the stator locator marks (378) and counts (379) on the stator ring (376), the position and/or velocity of the rotatable ring (380) may be used to control operation of the therapeutic radiation source, multi-leaf collimator, MV detector, PET detectors and other components on the rotatable ring. The stationary receiver unit (372) may comprise an encoder, and as the stationary receiver unit sweeps across the rotor locator marks (388) and counts (389) on the rotor ring (386), the position and/or velocity of the rotatable ring (380) may be used to control operation of the gantry drive controller and/or gantry drive motor. Timestamped stationary receiver or encoder data may be transmitted to a controller on the rotatable ring via the stationary transmitter unit (374) and compared with the timestamped rotatable receiver or encoder data to confirm/check the position and/or velocity of the rotatable ring. Timestamped stationary receiver or encoder data may optionally be transmitted via the data brush block. In some variations, data from the GIGACAP® rotor/stator and/or data from the encoders may be transmitted via a transmitter unit, and 10 BaseT data may be transmitted across the brush blocks. The rotatable ring (380) may also comprise one or more brush blocks (381) located at various circumferential locations for the transmission of data or power. For example, the rotatable ring (380) may comprise two power brush blocks (381) across which electrical power may be transferred from a stationary power source (not shown) to the rotatable ring. The rotatable ring may also comprise a data brush block (383) across which synchronization and/or offset data signals, including 10 BaseT data, may be transferred.

FIG. 3F depicts a schematic side cross-sectional view of a communication interface between a rotatable ring and stationary frame, as well as the rotor and stator that mechanically drive the rotation of the ring, cooling systems, and the various components and modules mounted on the rotatable ring. The stationary frame (390) may comprise a stationary receiver unit (392), a stationary transmitter unit (394), stator coils (396), stationary feedback or locator marks (398), and a motion controller (391). The rotatable ring (303) may comprise a rotatable receiver unit (305), a rotatable transmitter unit (307), rotor magnets (309), slip rings (311), a radiation delivery assembly (313), a PET detection system (315), electronics circuitry and components (317), a KVCT system (319), and a cooling system (321). The rotatable ring may also comprise a plurality of locator marks (397), as previously described. FIG. 3G depicts a front view of the stator coils (396) and rotor magnets (309). The stator coils may comprise a plurality of coils arranged in a ring-shaped band. The motion controller (391) may generate current through the stator coils (396) that may induce a magnetic flux that results in a motive force against the rotor magnets (309) that cause rotation of the ring. Gantry bearings (393) on the stationary frame (390) may help to guide the movement of the ring when subject to the motive force generated by the rotor/stator interaction, as previously described and depicted in FIG. 2. In some variations, the ball bearing assembly and the stator (e.g., stator coil(s)) may be retained by the same structure or housing, which may help generate sufficient motive force to rotate a ring with a few tons of components mounted thereon. The cooling system (321) may be located adjacent to the slip rings (311) to facilitate transfer of heat generated at the slip ring interface to the cooling system. For example, the cooling system may be configured to facilitate heat transfer between components at about 40° C. and a heat sink at about 20° C. Optionally, thermal conductors may couple the cooling system (321) with the radiation delivery assembly (313), and/or PET detection system (315), and/or electronics (317), and/or KVCT system (319). Additional description of variations of cooling systems is provided below.

Although these communication interfaces and/or slip-ring based communication links are described in the context of a continuously-rotating gantry driven by a rotary drive motor, it should be understood that such communication interfaces and/or links may be included in any type of rotatable gantry, including a rotatable gantry that uses a drive train mechanism comprising a static motor and static motion controller.

Radiation Shield Mounting

In radiotherapy, it is desirable for the therapeutic radiation beam to be well-controlled and characterized. For a therapeutic radiation source or linac mounted on a rotatable gantry, regulating the radiation beam while the gantry is rotating at different speeds and/or where the radiation beam may be projected from different gantry angles may be particularly challenging. Typical approaches to addressing this issue may comprise tightly mounting the linac onto the gantry using a stiff mounting mechanism, such that under the different conditions (speed, angle) the emitted radiation beam deviates as little as possible. Any beam generation components and beam limiting devices may be similarly mounted to the gantry to reduce deviation during these different conditions. Additionally, it may be desirable to provide a radiation shield around the body of the linac to help reduce any stray radiation that may be undesirably emitted from anywhere except through the desired aperture. Typically, this shielding is heavy (in some systems, may be on the order of about 400-500 pounds) and may pull significantly on the structure holding it around the linac. Currently, radiation therapy systems include a heavy/massive structure holding the linac, beam limiting devices and a radiation shield, which may be acceptable for relatively slow-rotating gantries (e.g., rotation speeds of less than about 10 RPM). However, due to the rapid rotation of the gantry at about 50 RPM to about 70 RPM or more (e.g., 60 RPM or more), the centripetal forces acting on this heavy mounting structure may give rise to mechanical stresses that may result in linac deviation and/or structural failures of the gantry.

The radiation therapy systems disclosed herein may comprise a linac (e.g., therapeutic radiation source) and a radiation shield disposed over the linac without contacting the linac, a first mounting assembly to mount the linac to the rotatable ring of a rotatable gantry, and a second mounting assembly that is separate from first mounting assembly to mount the radiation shield to the rotating ring. The second mounting assembly may comprise a shelf or bridge structure that securely attaches the radiation shield to the rotatable ring of the gantry. The first mount assembly and the second mounting assembly may be separated by an air gap, and/or may not directly contact each other. Mounting the linac and the radiation shield with separate mounting assemblies may help isolate any structural deflections or mechanical forces that may be generated by rotating the radiation shield from the linac and beam limiting devices. Isolating these mechanical forces may help promote the stability and/or precision of delivered radiation under different operating configurations, while still having a radiation shield.

Figure 4A:
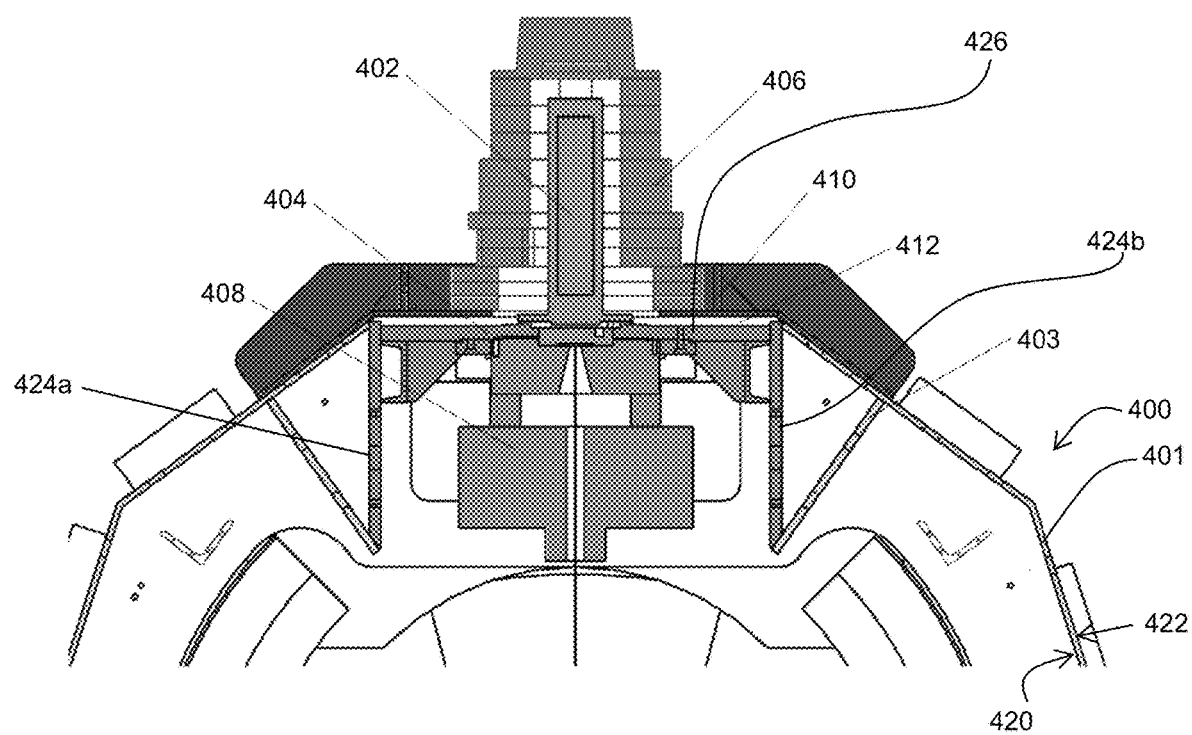
FIGS. 4A-4B are illustrative depictions of variations of a linear accelerator (linac).
Figure 4B:
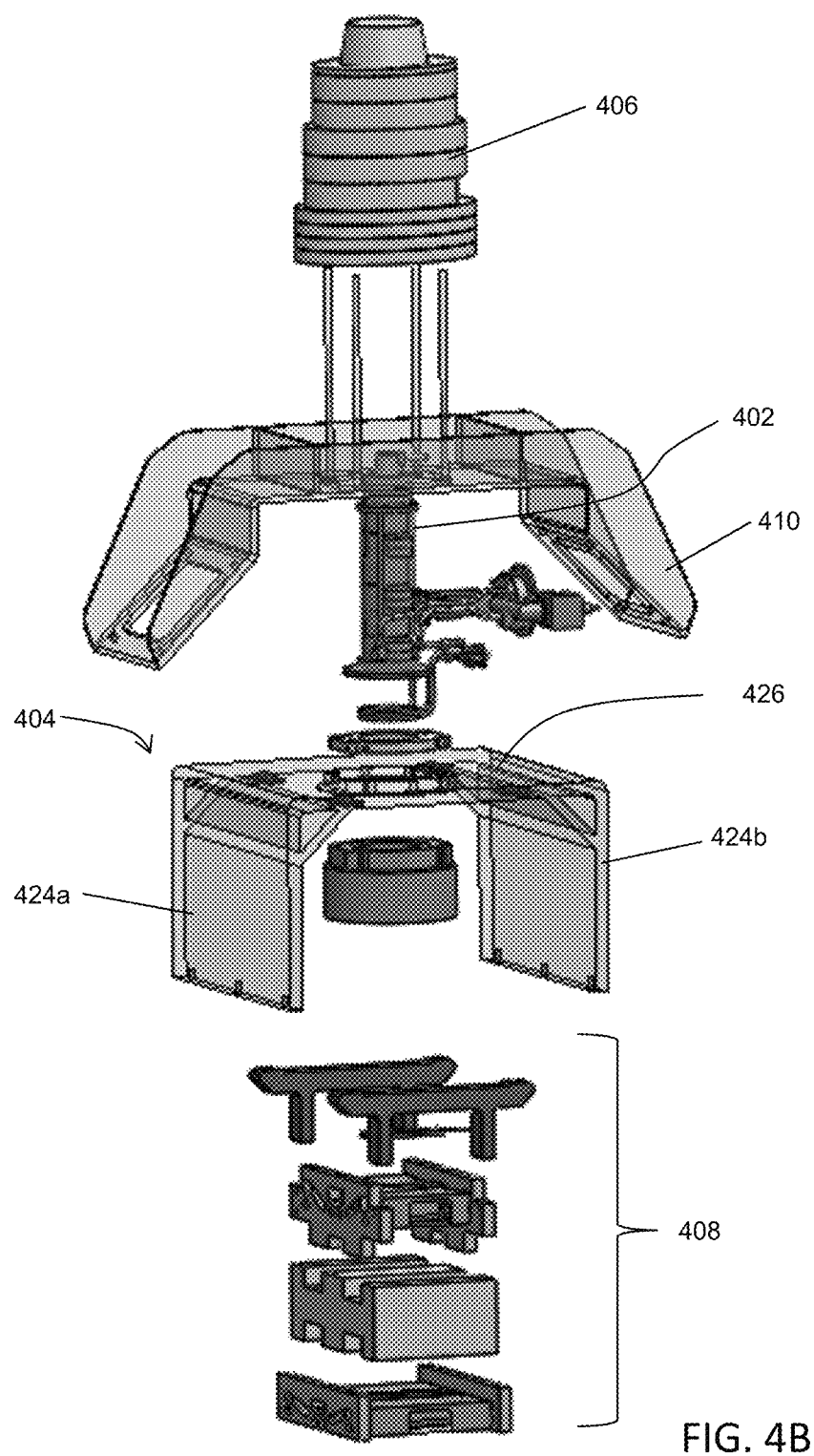

FIG. 4A depicts a one variation of a linac, radiation shield and corresponding mounting assemblies for a rotatable gantry and FIG. 4B depicts an exploded view of the linac, radiation shield and corresponding mounting assemblies of FIG. 4A. Turning to FIG. 4A, the rotatable ring (400) of a gantry may comprise a chassis or support structure (401) upon which a linac (402) and a linac radiation shield (406) are mounted. The support structure (401) may comprise a first interior side (420) and a second exterior side (422), and may further comprise a mounting bracket (403) located on the first interior side (420). The mounting bracket (403) may compromise one or more beam(s) or plate(s). The linac (402) may be mounted on the rotatable ring (400) by a first mounting assembly (404), which may have two panels (424a, 424b) connected to a top plate (426), as depicted in FIG. 4B. In some variations, the panels (424a, 424b) and top plate (426) may be welded together, and may be welded into the support structure (401) of the gantry. The linac (402) may be disposed over an opening in the top plate (426) and fixedly attached to the top plate (426). The top plate (426) may lay flush with the exterior side (422) of the gantry support structure (401), or may be set slightly in from the exterior side (422). The panels (424a, 424b) may extend towards the interior side (420) of the support structure (401) and attach to the mounting bracket (403). Any beam limiting or shaping devices (408) may optionally be attached to the first mounting assembly (404). This may help maintain the relative positioning between the linac and the beam limiting or shaping devices. In the variation depicted in FIGS. 4A and 4B, the radiation shield (406) may be disposed over the linac (402) and mounted on the rotatable ring (400) by a second mounting assembly (410), which may have a bridge-shape with two sloped panels extending from an upper, generally horizontal panel. That is, the top portion of the second mounting assembly (410) may have a curve, shape, or surface that tracks along a length of the circumference of the gantry ring, e.g., tangential to the curvature of the ring, and two side portions that curve or bend from the top portion, following along the curvature of the ring. More generally, the radiation shield mounting assembly may have a shape that corresponds to the curvature of the gantry and/or the surface contours of the gantry, which may help to secure the shield the gantry by increasing the contact surface area and attachment points between the mounting assembly and the gantry. For example, a mounting assembly that approximately tracks the curve of the gantry may help to distribute forces along the support structure of the gantry, and/or allow for more surface area for weld joints, solder joints, screw joints, and other mechanical attachments. The second mounting assembly (410) may be attached to the exterior side (422) of the support structure (401) and separated by an air gap (412) from the first mounting assembly (404). For example, the first mounting assembly (404) and the second mounting assembly (410) may be attached to different supporting structures or beams of the rotatable ring. The linac (402) and the radiation shielding (406) may also be separated by a gap as well.

Linac Alignment

A radiation beam or spot emitted by the linac may be precisely aligned with beam limiting or shaping devices (e.g., multi-leaf collimator), which may help attain and maintain precise and/or accurate therapy beam performance. In some variations, the alignment between the linac radiation beam or spot and the collimator may be within a predetermined tolerance threshold of about 200 microns or less. The alignment of the linac spot to the collimator may be checked in at least three circumstances: in the factory, upon delivery of the system to a clinic, and in the event that the linac or beam converter is serviced in the field. Alignment may comprise the steps of firing a pulse from the linac though the collimator and measuring the incidence of the pulse on the detector located opposite the linac (e.g., MV detector). Based on the known configuration of the collimator (e.g., certain leaves open, certain other leaves closed) and the data from detector, the controller may determine whether the linac alignment is within the predetermined tolerance. If the radiation beam or spot is not aligned to the collimator within the predetermined tolerance, the location of the linac may be adjusted. Such adjustment has typically been performed manually, and is often considered to be cumbersome to open the bunker door, move the linac, close the bunker door, fire the linac pulse, and measure the linac location and beam spot with respect to the collimator, as these steps can be repeated several times before the desired alignment is achieved.

The radiation therapy systems described herein may optionally comprise an intermediate adjustor plate to which the linac is mounted, an alignment actuator, and a lock-down mechanism that secures the position of the intermediate adjustor plate once the desired alignment between the linac and the collimator is attained. In some variations, the alignment actuator may be removable so that the actuator may be removed after the linac has been aligned, which may help to limit exposure of the actuator to the radiation generated by the system during a therapy session. The linac (and optionally, the beam converter and/or beam-limiting components associated with the beam converter) may be mounted to the adjustor plate, and the plate may be moved with respect to the collimator by the actuator. In one variation, the adjustor plate may be coupled to the actuator via a screw, and the motor of the actuator may rotate the screw to move the adjustor plate. In some variations, the adjustor plate may be coupled to one or more actuators via two screws, where rotation of a first screw moves the plate along a first axis (e.g., x-axis) and rotation of a second screw moves the plate along a second axis that may be orthogonal to the first axis (e.g., y-axis).

The alignment actuator may be controlled remotely by an operator located in a room separate from the radiation therapy treatment room. For example, the alignment actuator may optionally be in communication with a wireless transceiver that may receive remote operator commands. Alternatively or additionally, the alignment actuator may be connected by one or more wires to a controller in another room. This may allow the linac radiation spot to be aligned with the collimator by an operator located outside the bunker and when the desired alignment is attained, the operator may lock the linac and the plate to the desired location, and may optionally remove the alignment actuator before the treatment session. Radiation therapy systems comprising a kV or imaging radiation source may optionally comprise the same mechanism to adjust the alignment of the kV or imaging radiation source with respect to the kV detector. Radiation therapy systems comprising an MV detector may include an angle adjustment mechanism having an anchor on one end and an adjustment screw on the other end to align the MV detector array to a jaw face.

Figure 4C:
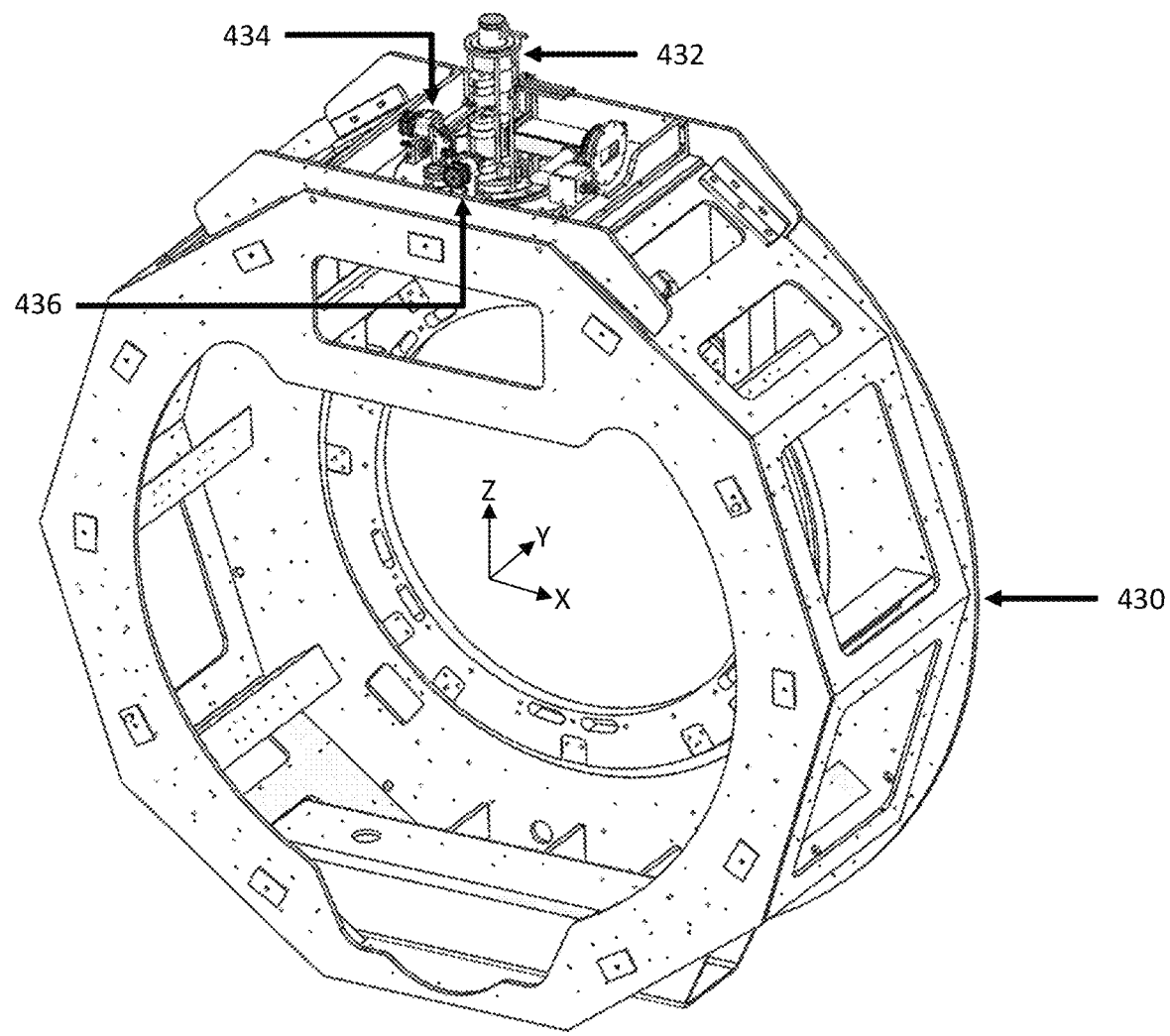
FIG. 4C is a perspective view of one variation of a gantry with a linac and mounting assembly.
Figure 4D:
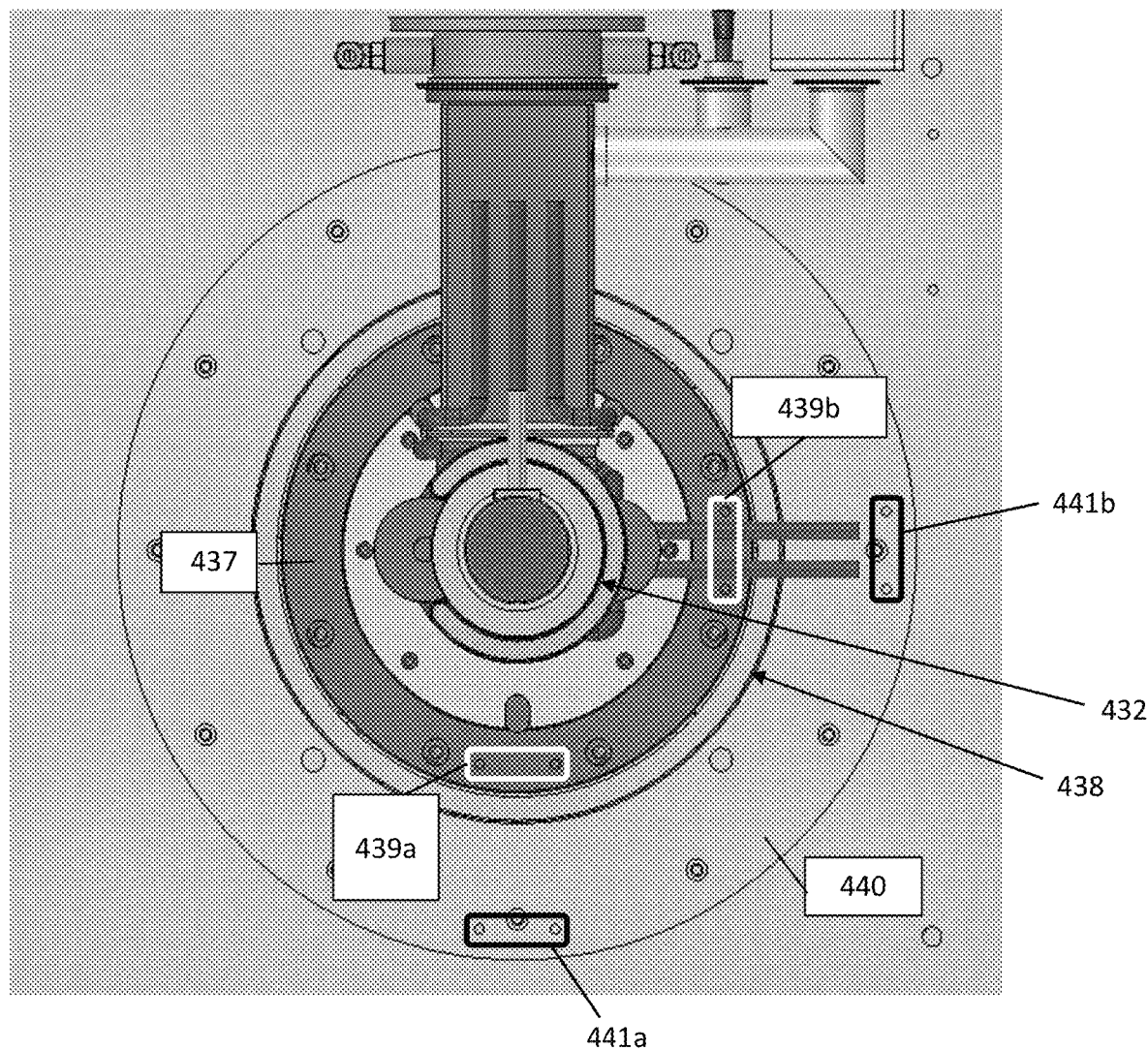
FIG. 4D is a top view of one variation of a linac position adjustment assembly.
Figure 4E:
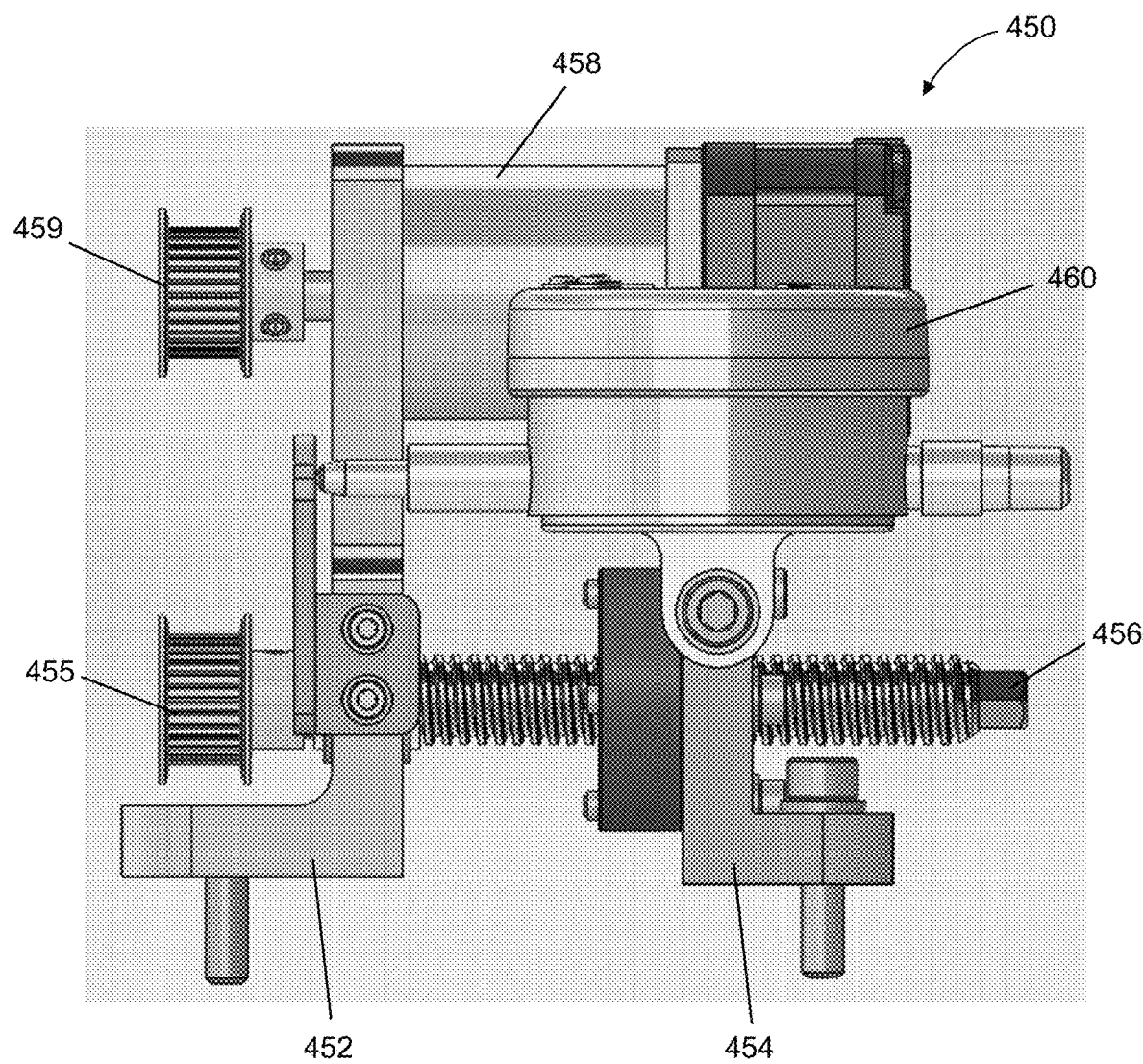
FIG. 4E is a side view of one variation of a linac position adjustment assembly.

FIGS. 4C-4E depict one variation of radiation source (linac) adjustment mechanism. FIG. 4C is a perspective component view of a rotatable gantry ring (430) and a linac (432) mounted to the gantry (430) where the linac beam path is along the Z-axis, an X-axis adjustment assembly (434), and a Y-axis adjustment assembly (436). The linac (432) may be mounted to a movable adjustor plate to which the X-axis adjustment assembly (434) and the Y-axis adjustment assembly (436) may be attached. The adjustment assemblies may also be attached to a linac base plate (440) that is fixedly mounted on the gantry ring (430), e.g., may be mounted to a primary collimator. FIG. 4D depicts a top view of the linac (432) mounted on the adjustor plate (438). The adjustor plate (438) may comprise plate adjustor mounts (437) comprising one or more mounting holes (439a) for the X-axis adjustment assembly (434) and one or more mounting holes (439b) for the Y-axis adjustment assembly (436). The adjustment assemblies may be attached to the adjustor plate and the linac base plate (440) with one or more screws that engage within the mounting holes on the adjustor plate (439a, 439b) and one or more holes (441a, 441b) on the linac base plate. While the adjustment assemblies may be coupled to the adjustor plate and base plate by one or more screws, it should be understood that the assemblies may be attached by welding, brazing, adhesives, etc. The adjustor plate (438) may be moved with respect to the baseplate (440) based upon actuation by the adjustment assemblies (434, 436).

FIG. 4E depicts a close-up side view of one variation of an adjustment assembly for positioning a linac. This adjustment assembly may be used for either the X-axis adjustment assembly or the Y-axis adjustment assembly, and may be used to adjust the position of any radiation source and/or detector, as appropriate. The adjustment assembly (450) may comprise a first mount (452) that is configured to attach to the adjustor plate (438), a second mount (454) that is configured to attach to the base plate (440), a screw (456) that connects the first mount and the second mount together, and a stepper motor (458) that rotates the screw (456) to adjust the distance between the first mount (452) and the second mount (454). The stepper motor (458) may be coupled to the screw (456) via a drive belt between the motor and the screw. For example, the screw (456) may comprise a first pulley (455) located at one end of the screw and the stepper motor (458) may comprise a second pulley (459) coupled to a rotating shaft of the motor, and a belt that spans both the first and second pulley such that rotation of the second pulley (459) causes rotation of the first pulley (455), thereby rotating the screw (456) to move the adjustor plate relative to the base plate. Some variations of a stepper motor may comprise a gear box that adjusts the generated torque to a level suitable for moving the adjustor plate and the linac mounted thereon. The adjustment assembly (450) may also comprise a dial indicator (460) that provides a mechanical reference for an operator to keep track of movement in the adjustment plane. In some variations, the alignment assembly may comprise a wireless transceiver in communication with a remote controller or processor so that activation of the motor and movement of the linac may be controlled from another room. Alternatively or additionally, the alignment assembly may be connected by one or more wires to a controller or processor in another room. The first mount (452) may be coupled to the adjustor plate (438) via screws, pegs or protrusions that correspond with the mounting holes (439) of the adjustor plate and the second mount (454) may be coupled to the base plate via screws, pegs or protrusions that correspond with the mounting holes (441) of the base plate. The adjustment assembly (450) may be used for adjusting the position of the linac along the X-axis and Y-axis. While adjustment assembly (450) uses a stepper motor that rotates a screw to move the linac adjustor plate, other variations may use other mechanisms to move the linac adjustor plate, for example, rack-and-pinion mechanisms, electromagnetic actuator mechanisms, and the like.

Figure 4F:
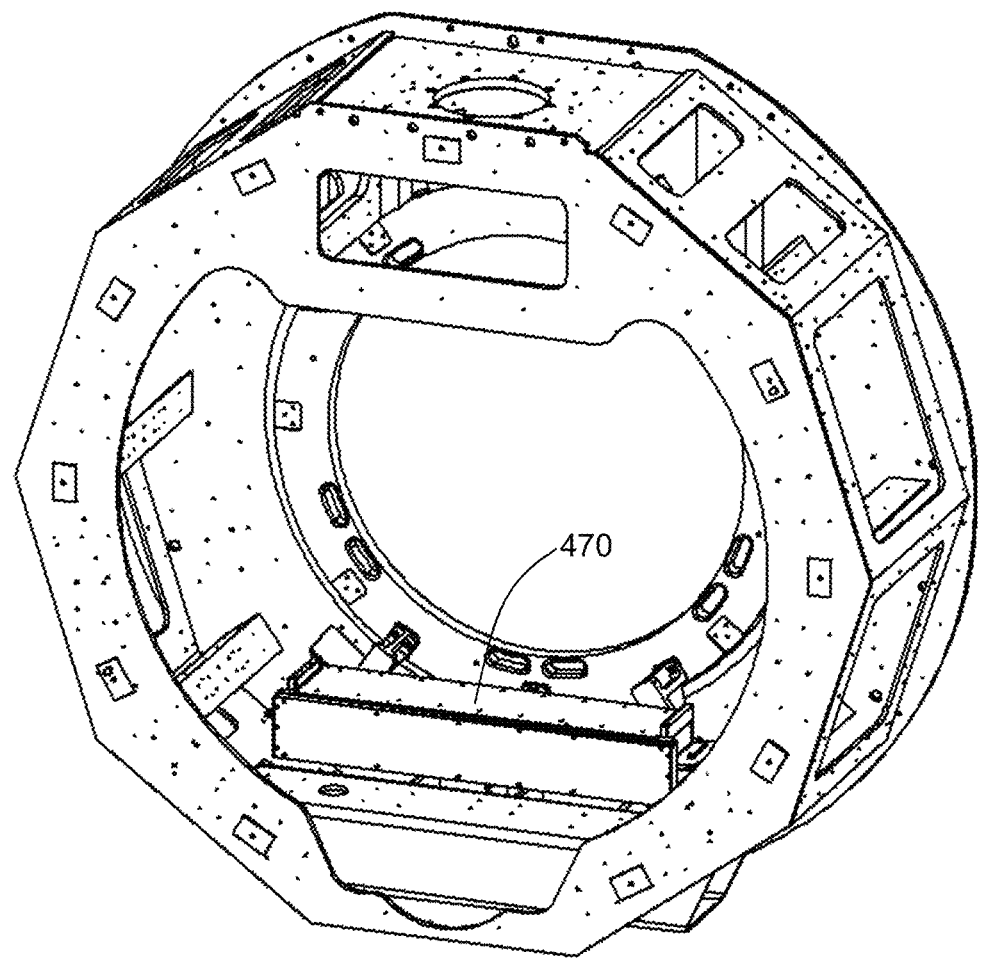
FIG. 4F is a perspective view of one variation of a gantry with a MV detector, mounting assembly and position adjustment assembly.

In some variations, the MV detector located across from the linac may also be adjusted to help ensure consistent alignment with the linac. For example, the linac and MV detector position may be adjusted together, and/or the position of the linac or MV detector may be checked when the position of the MV detector or the linac is adjusted to ensure that they are aligned (e.g., the center of the MV detector is across from the center of the linac beam). FIG. 4F depicts a gantry ring and a MV detector (470) mounted thereon. The linac may be mounted directly across from the MV detector (470), for example, over the opening across from the MV detector, using mounting and position adjustment mechanisms described above. The MV detector mounting mechanism may comprise a series of gantry mounting flanges and alignment or adjustor plates that are mounted with the flanges to the gantry ring to control the MV detector position along the X-axis, Y-axis and Z-axis (where the linac applies radiation along the Z-axis). Gantry mounting flanges may be configured to pivot or tilt the MV detector relative to isocenter, and may be used, for example, to establish a nominal Y-axis and Z-axis position relative to the MV beam source (e.g., linac). The co-mounted alignment plates may be configured to rotatably adjust the MV detector along the z-axis to align correctly to the plane established by the MV beam source. Optionally, the alignment or adjustor plates may optionally add adjustability for discrete y-axis positions offset from the nominal plane in both positive and negative directions (e.g., during testing or calibration sessions).

Figure 4G:
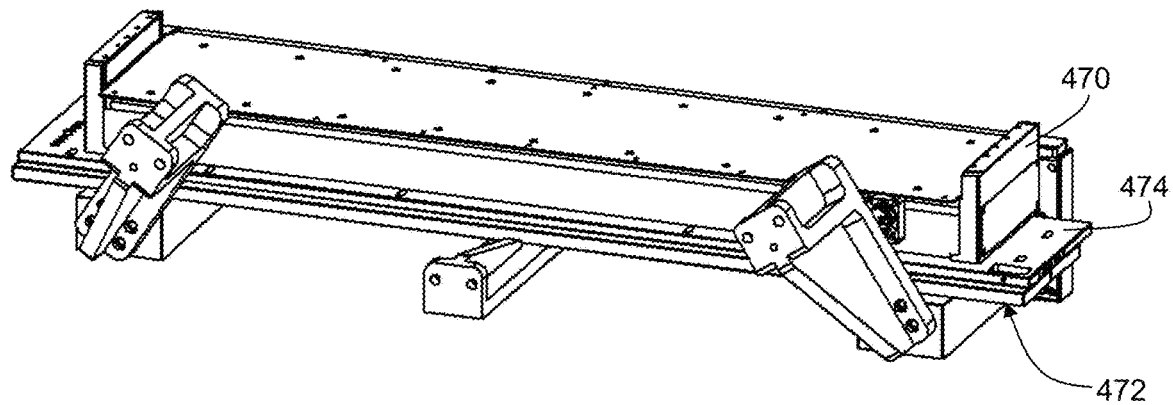
FIGS. 4G-4H depict a perspective view and an exploded perspective view of the MV detector and position adjustment assembly of FIG. 4F.
Figure 4H:
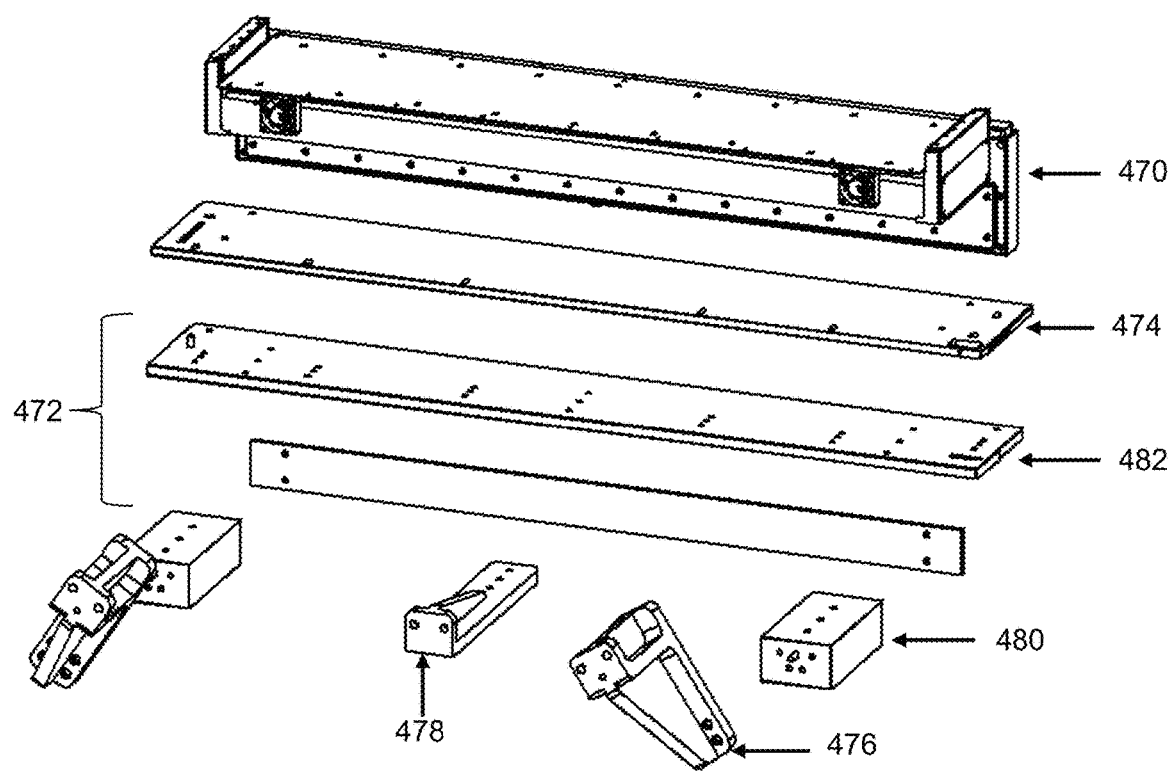
Figure 4I:
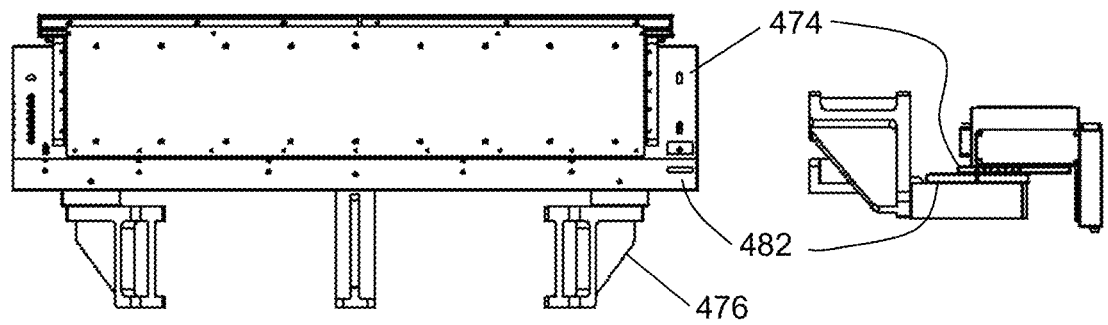
FIGS. 4I-4J depict various configurations of a MV position adjustment assembly.
Figure 4I:
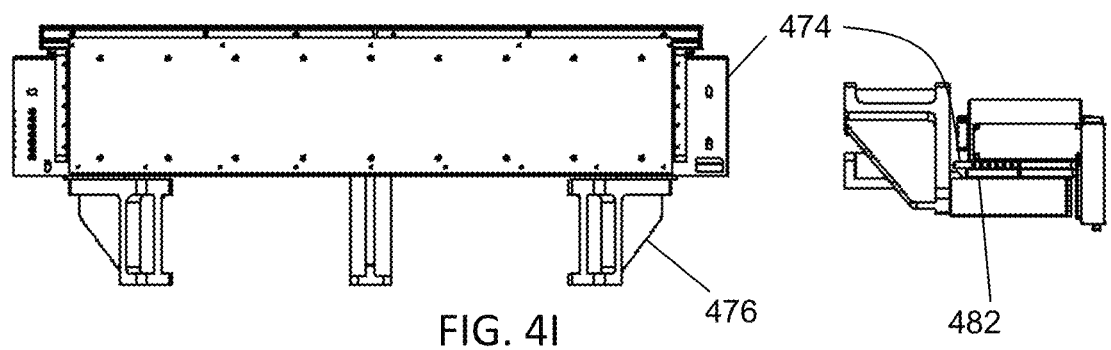
Figure 4J:
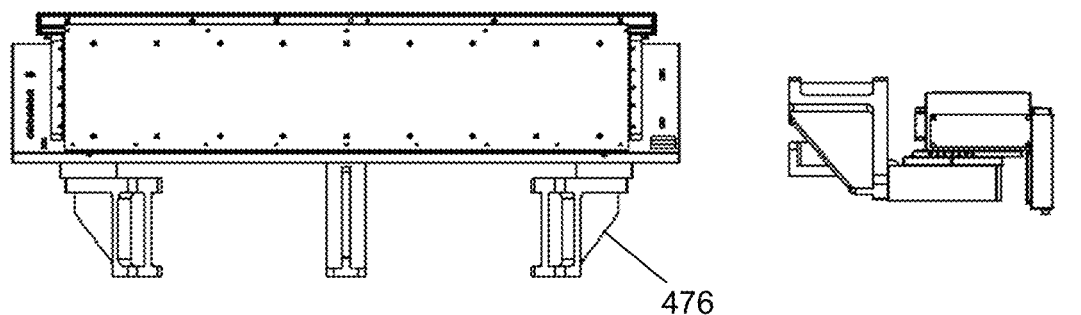
Figure 4J:
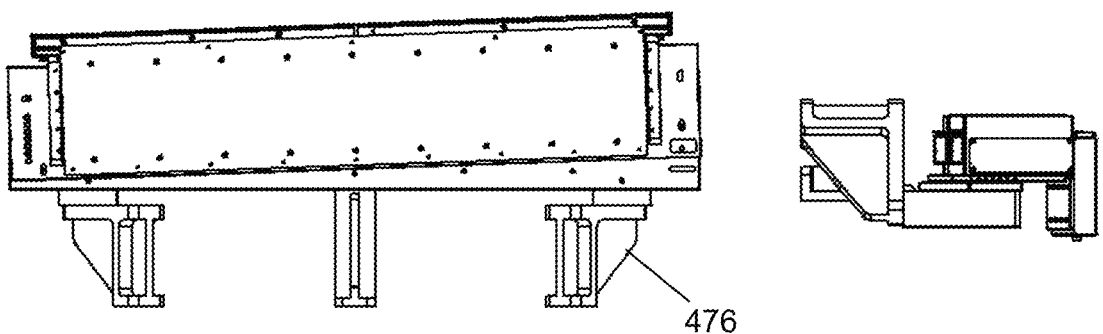

FIG. 4G depicts a perspective view of a MV detector (470) and its mounting and position adjustment assembly. The mounting and adjustment assembly may comprise alignment or adjustor plates (474) that are movably attached to a gantry mount assembly (472). The mount plate (472) may be fixedly attached to the gantry ring. FIG. 4H depicts an exploded view of the MV detector (470), alignment plate (474), and gantry mount assembly (472). The gantry mount assembly (472) may comprise an MV support plate (482) and support blocks (480) attached to the bottom surface of the MV support plate (482). The MV detector (470) may be mounted directly to the alignment plate (474). The MV support plate and support blocks may be fixedly attached to the gantry ring, e.g., via bolts and/or an alignment pin. The alignment plate (474) may be coupled to a mechanism (such as the mechanism described above with regard to the linac mounting and position adjustment assembly) that is configured to translate the MV detector along one axis (e.g., Y-axis) and/or may be coupled to a pivotable or rotatable mechanism that is configured to rotate the MV detector about one axis (e.g., Z-axis). The mounting and position adjustment assembly may also comprise mounting flanges (476, 478) that are coupled o the support blocks (480) and the support plate (482). FIG. 4I depicts two possible translation positions offset from the nominally aligned position shown in FIG. 4J (top diagram of FIG. 4I depicts the adjustment assembly in a fully extended configuration and the bottom diagram of FIG. 4I depicts the adjustment assembly in a full retracted configuration). FIG. 4J depicts the nominally aligned position of the MV detector assembly alongside one possible rotated or pivoted state (top diagram of FIG. 4J depicts the adjustment assembly in a nominal configuration and the bottom diagram of FIG. 4J depicts the adjustment assembly in a rotated or pivoted configuration).

Temperature Control

Figure 5A:
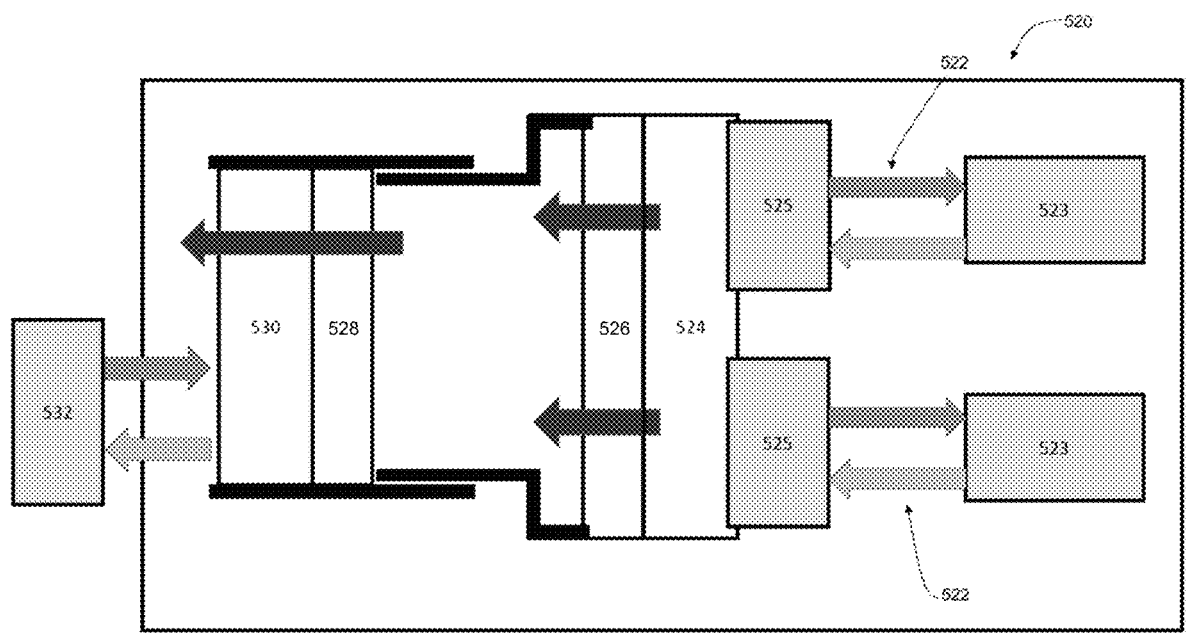
FIGS. 5A-5E are illustrative depictions of one variation of a temperature management system that may be used with a rotatable gantry.

Generally, the systems described herein may comprise a radiation therapy system comprising a temperature management system to help maintain a system temperature within an operable range. A continuously-rotating gantry for radiotherapy presents a challenging temperature or thermal management problem. A gantry that is capable of rotating at speeds from about 10 RPM to about 70 RPM may generate greater amounts of heat than a gantry rotating at slower speeds. For example, a continuously-rotating radiation therapy system can produce over 70 kW of heat. Many of the sensors in the radiation therapy system are sensitive to changes in temperature, and elevated temperatures may negatively impact patient comfort as well. Large-bore, continuously-rotating fluid unions, which have been used in radiation therapy systems with low-speed gantries (e.g., less than about 10 RPM), may not be suitable for use with high-speed gantries (e.g., about 20 RPM to about 70 RPM, about 60 RPM or more). In addition to removing heat from the gantry itself, a temperature management system may also need to remove the heat from the gantry enclosure and the treatment bunker. Temperature control may be managed at many levels by several methods. Methods for temperature control may include feedback loops with temperature and air flow sensors where sensor data may be used to adjust fan operation (e.g., speed control), rate of hot and cold liquid mixing on the rotatable ring and/or between the rotatable ring and stationary frame, and/or control of liquid flow on the rotatable ring. In some variations, a temperature management system for moving heat across the rotatable ring and/or to the stationary frame and/or to the clinic or facility heat sink may comprise multiple liquid branches or conduits on the rotatable ring, and/or fluid pumps or other regulators, and/or rotatable ring heat exchangers, and/or stationary heat exchangers, and/or contacting or mixing heated liquid from the rotatable ring with cooled liquid on the stationary frame. FIG. 5A is a block diagram that represents one variation of heat transfer from the rotatable ring to the stationary frame. Heat generated by the components on the rotatable ring may be transferred to a cooling fluid that may be circulated throughout the ring. The heat from transferred to the cooling fluid may be transferred to air that is circulated between the rotatable ring and the stationary frame via one or more forced-air heat exchangers (e.g., via air ducting with or without the aid of one or more fans). Heated air from the rotating ring (as well as heat from the components on the stationary frame) may be channeled to facility cooling fluid. Alternatively, heated air from the rotatable ring may be directly transferred to the facility cooling fluid, without the use of forced-air heat exchangers. In the variation depicted in FIG. 5A, the temperature management system (520) may comprise one or more fluid conduits (522) that circulate fluid between the components (523) on the rotatable gantry (e.g., linac, magnetron, collimator, jaws, PET detector array(s), MV detector, etc.) and one or more heat exchangers (524). The fluid conduit (522) may form a loop that transfers heated fluid from the components to the heat exchangers (524) where the fluid is cooled by one or more fans (526). The cooled fluid is then circulated back to the components (523). In some variations, a fluid flow controller (525) may be located on the rotatable ring to regulate fluid rate depending on data from temperature sensors on the rotatable ring. Heat from the fluid is transferred to the air via fans (526), which is then channeled to one or more stationary heat exchangers (530). Optionally, the rate of heated air flow between the rotatable ring and stationary frame may be expedited by a second set of fans (528) adjacent to the stationary heat exchangers. The stationary heat exchangers (530) may transfer the heat from the air to a facility cooling system (532). The facility cooling system may be an air-based or fluid-based cooling system, for example, circulating cooled air that mixes with the heated air in the stationary heat exchanger (530), or circulating cooled fluid in contact with the fluid in the stationary heat exchanger (530) that has been heated by the hot air from the heat exchanger (524).

One variation of a temperature management system for a radiation therapy system with a high-speed gantry may comprise two sets of heat exchangers and ducting. For example, a heat exchanger may comprise a copper substrate having a high surface-area-to-volume ratio and liquid ducting that is thermally coupled to the surface of the substrate. Heat from the rotating gantry may raise the temperature of the air surrounding the gantry, which heat may be transferred to the exchanger substrate, for example, via air flow provided by a fan or via radiative conduction. Heat from the substrate may then be transferred to cooled liquid within the ducting, which may then move the heat away from the gantry to a liquid reservoir. The cooled liquid may be, for example, water, and may be circulated locally (e.g., within or in proximity to the room or bunker where the therapy system is located) and/or may be circulated across the treatment facility. The first set of heat exchangers and ducting may be configured to transfer heat generated from the rotating ring to the stationary frame of the gantry, and the second set of heat exchangers and ducting may be configured to transfer the heat from the stationary frame to a closed-loop, facility liquid system. In this configuration, heat from the components mounted on the rotating ring may be removed with a rotatable, closed-loop water system. The rotatable water system may be configured to transfer the heat to ducting in the stationary frame using either forced-air heat exchangers or radiative heat exchangers. For example, the heat may then be transferred to chilled fluid (e.g., provided by the facility) via ducting in the stationary frame that may be coupled to a forced-air system. The forced-air system may be ducted through a second set of heat exchangers that may be coupled to chilled fluid. Some of this chilled, forced-air may be directed under the gantry enclosures to maintain a constant ambient air temperature. Variable speed fans or variable chilled fluid flow may be used to maintain the temperature of the stationary heat exchange system.

Figures 5B, 5C:
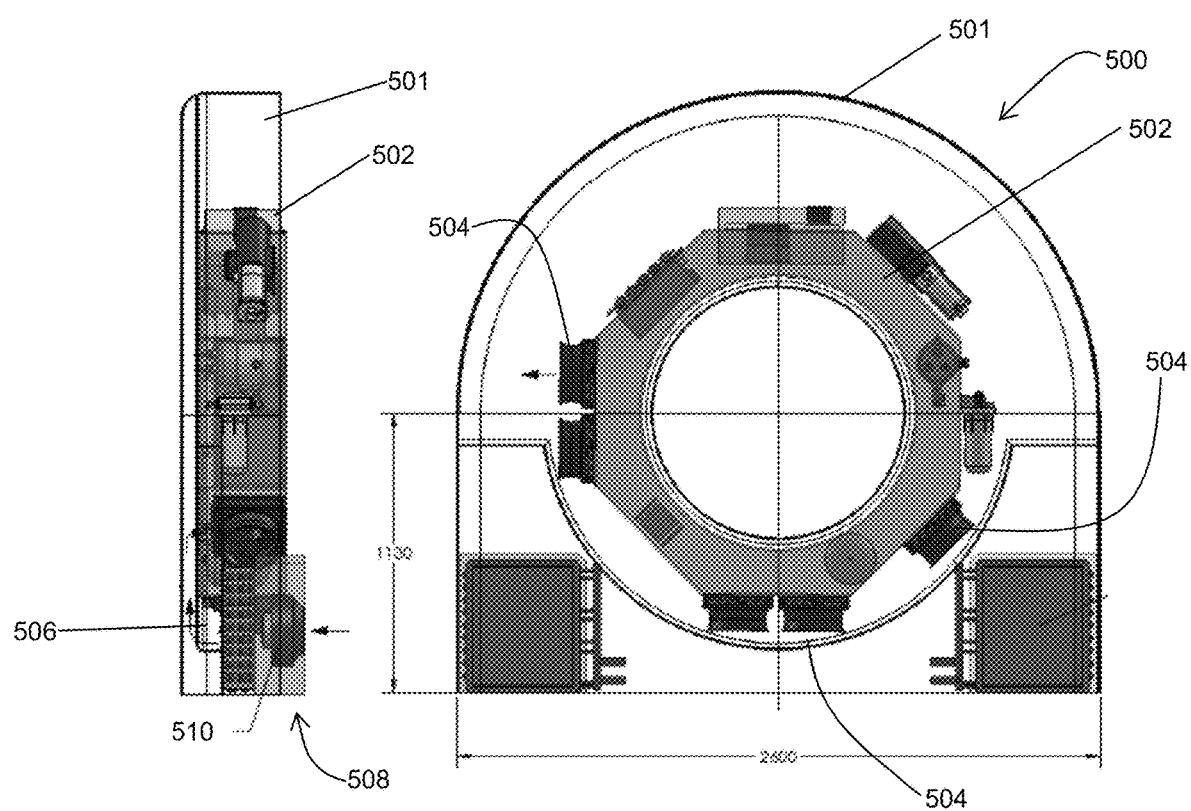
Figure 5D:
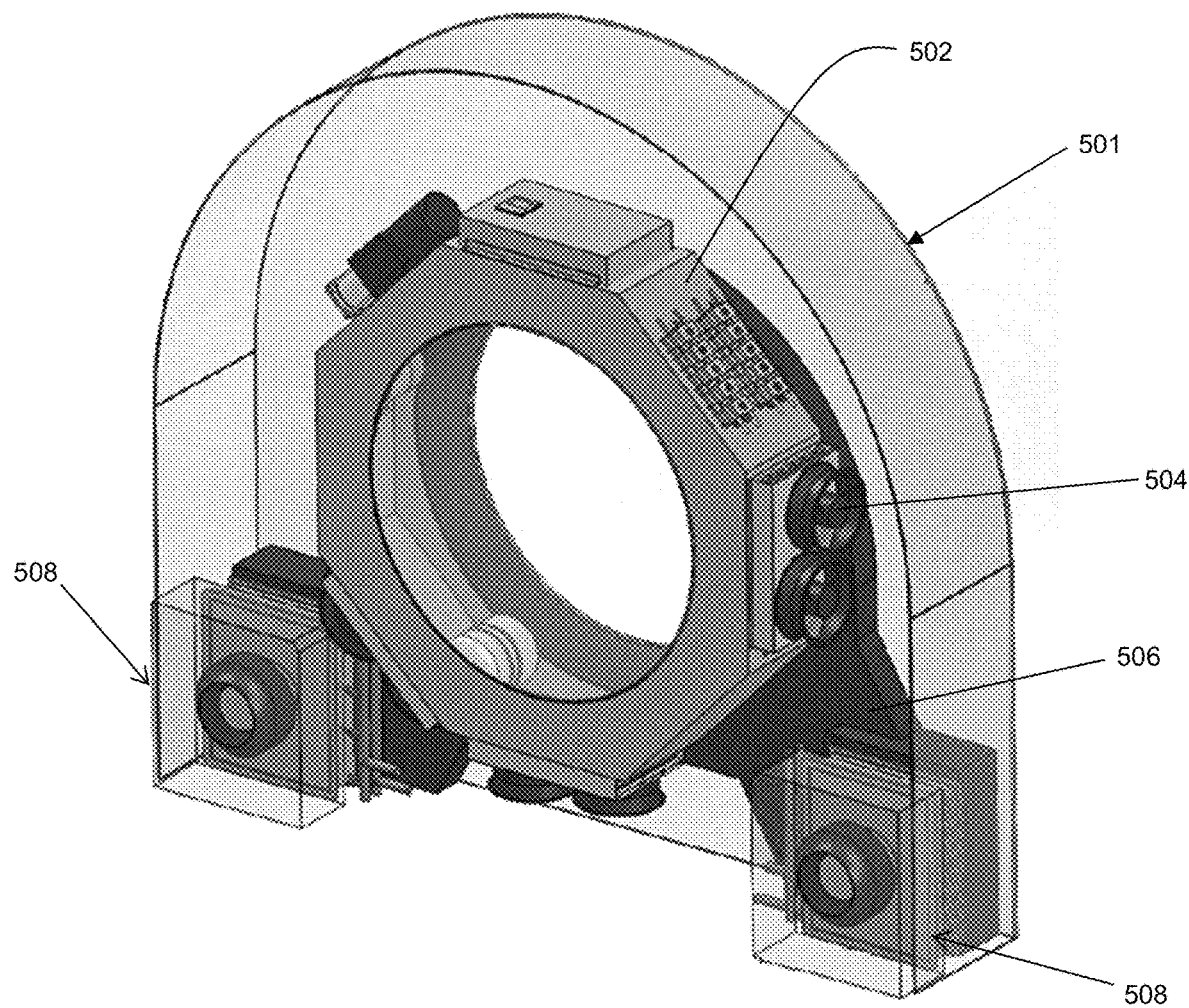
Figure 5E:
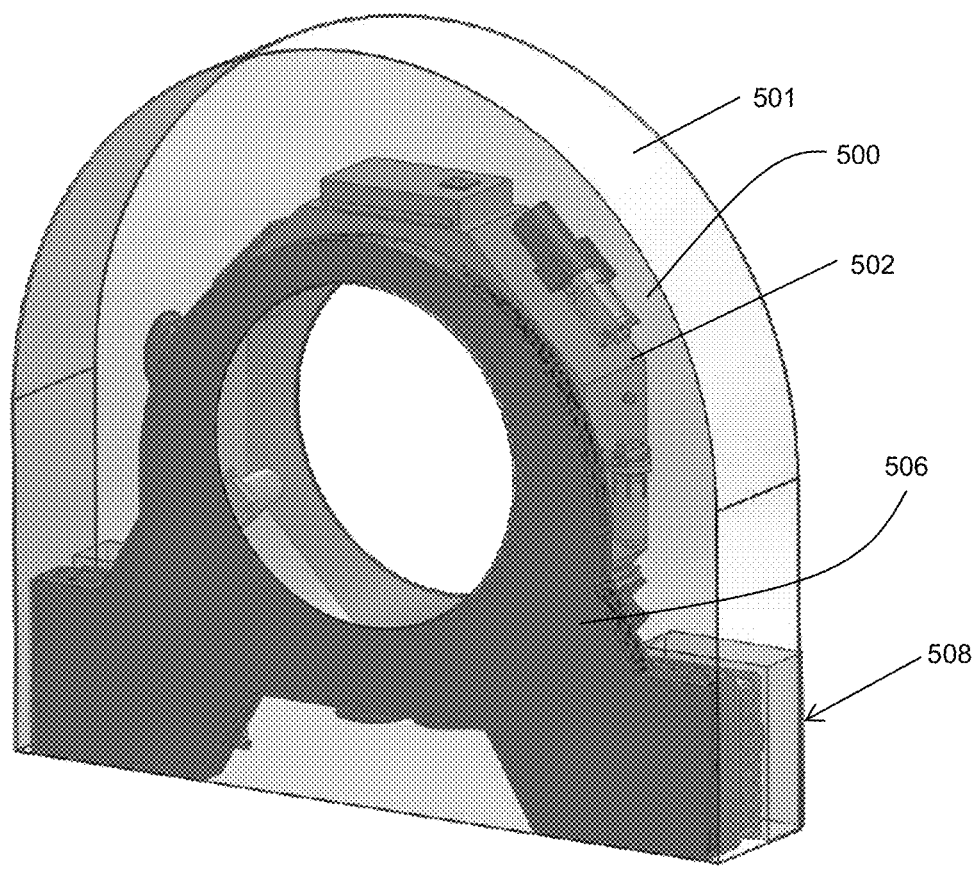

One variation of a temperature management system is depicted in FIGS. 5B-5E. FIG. 5B depicts a gantry (500) enclosed within a housing (501). The gantry (500) may comprise a rotatable ring (502) and a stationary frame (not depicted). A temperature management assembly may comprise a first heat exchange interface comprising one or more exhaust components (504) mounted on the rotatable ring (502) and a stationary duct (506) located within the enclosure of the housing (501). The rotatable ring (502) may be coupled or mounted to the stationary frame. The exhaust components (504) may be at one or more locations along the circumference of the rotatable ring (502). Any number of exhaust components (504) may be mounted on the rotatable ring, for example, one exhaust component, two or more exhaust components, three or more, four or more, five or more, or ten or more exhaust components. Additional exhaust components may be located near components with high thermal output. In some variations, a kV CT head may comprise a supplemental exhaust component. Exhaust components or forced-air heat exchangers may comprise one or more fans oriented such that the air flow direction is along a radial direction (i.e., perpendicular to the axis of rotation). Air flow that is parallel to the axis of rotation may not channel air as efficiently as radial air flow that is perpendicular to the axis of rotation. This may be particularly pronounced when the gantry is rotating at speeds of about 50 RPM or more (e.g., about 60 RPM). For example, the first heat exchange interface depicted in FIG. 5B comprises five exhaust components (504). Exhaust component (504) may transfer heat generated by the components on the rotatable ring (502) to the stationary duct (506), depicted in FIGS. 5D-5E. The stationary duct may have a shape similar to that of the rotatable ring (502), such that heat can be transferred from the exhaust components (504) to the stationary duct (506) while the ring (502) rotates. For example, as depicted in FIG. 5E, the stationary duct (506) may have a circular shape that corresponds with the shape of the rotatable ring (502). Heat generated by a component on the rotatable ring (502) may raise the temperature of the surrounding air, this heated air may be captured by the exhaust component (504) and moved toward the stationary duct (506). The temperature management system may further comprise a second heat exchange interface comprising the stationary duct (506) and air portal (508). The air portal (508) may be configured for unidirectional and/or bidirectional air flow and exchange and may be connected to a facility reservoir of cooled air or fluid. In the example depicted in FIGS. 5C-5E, the air portal (508) may comprise a fan (510) that transports cooled air from a facility reservoir into the enclosure of the housing (501) and transports heated air from the rotatable ring (502) out from the exhaust component (504). Optionally, some components on the rotatable ring may have a dedicated heat transfer or cooling pathway (i.e., a dedicated cooling fluid flow system and/or forced-air heat exchanger or exhaust to move heat to the stationary frame). For example, the magnetron may have a dedicated cooling pathway.

Gantry Bore

In some variations of the system, a radiotherapy device having a rotatable gantry may comprise a bore that is configured to reduce patient discomfort due to confinement within a small space (e.g., claustrophobia). In some variations, the gantry may provide a comfortable patient environment to reduce patient anxiety and increase patient compliance with radiotherapy treatment. For example, in some variations, the bore of a rotatable gantry may increase in diameter towards an end of the bore (i.e., a variable-diameter or stepped bore) to reduce claustrophobia and the perception of confinement (e.g., patient lying still during a procedure), thereby allowing the patient to remain still on a patient platform for a longer period of time.

Figure 6A:
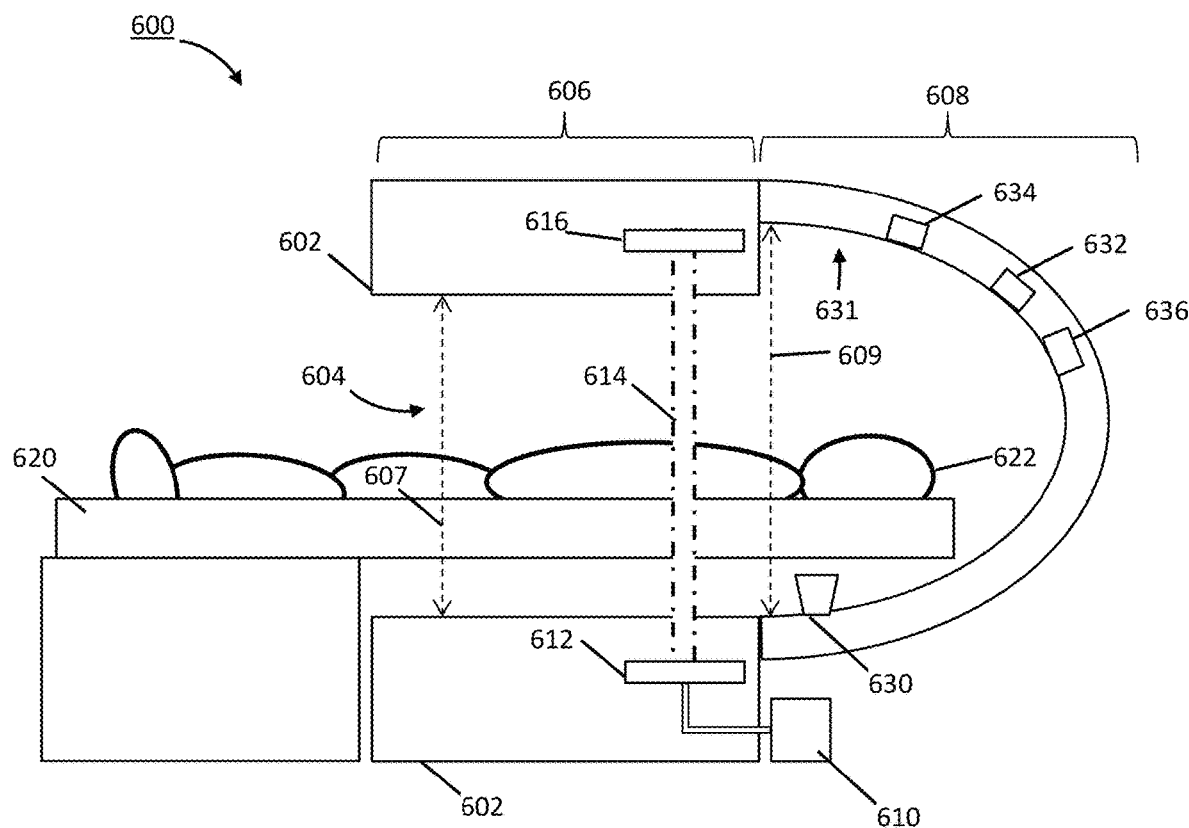
FIGS. 6A-6B are illustrative depictions of some other variations of a gantry.
Figure 6B:
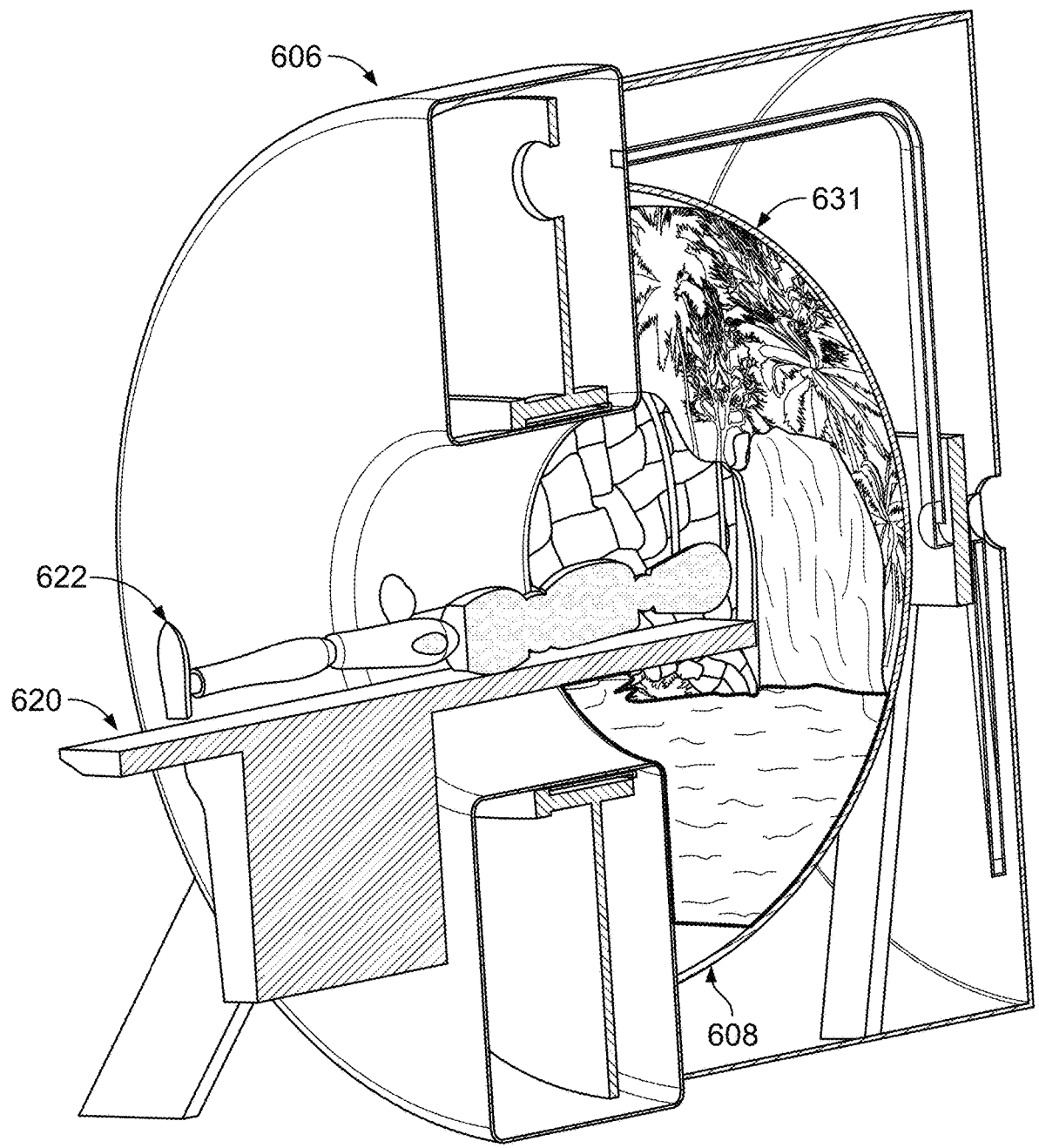

In some variations, the bore may be open on both ends (e.g., an open-bore gantry) while in other variations, the bore may be open on one end and closed on the other (e.g., a closed-bore gantry). One of the ends of the bore may be open in order to receive a patient on a patient platform for radiotherapy treatment. As described in detail below, the bore may be enclosed at one end while the perception of an enlarged space within the bore is maintained. FIGS. 6A-6B represent an exemplary radiotherapy device (600) comprising a closed-bore gantry (602), where the closed end of the bore (604) (second portion (608)) has a diameter that is greater than a diameter of the open end of the bore (604) (first portion (606)). In some variations, the gantry (602) may comprise a first portion (606) and a second portion (608). As depicted in FIG. 6A, a patient (622) disposed on a patient platform (620) may be advanced into the bore (604) from a circular opening of a first end of the first portion (606). A second end of the first portion (606) may be coupled to an enclosure of the second portion (608). The patient (622) may be advanced such that their head is positioned within the enclosure of the second portion (608). By increasing the diameter of the bore (604) where the patient's head is positioned during treatment, claustrophobia may be reduced as the patient's perception of confinement may be lessened without increasing a diameter along an entire length of the bore (604).

In some variations, the diameter (609) of the second portion (608) of the bore (604) may be up to four times larger than the diameter (607) of the first portion (606) of the bore (604). In some examples, the diameter (609) of the second portion (608) of the bore (604) may be about three times larger than the diameter (607) of the first portion (606) of the bore (604). In other variations, the diameter (609) of the second portion (608) of the bore (604) may vary as the diameter (607) of the first portion (606) of the bore (604) may be substantially constant. As shown in FIGS. 6A-6B, the second portion of the bore (604) may have an ellipsoid shape (e.g., hemispherical shape), and may be illuminated, as described in further detail below. The second portion (608) may comprise any shape configured to simulate an enlarged space. For example, the second portion (608) may comprise a cuboid shape, such as an open box shape. Furthermore, the second portion may enclose the patient (622) to the extent of the patient's field of view. For example, the bore (604) of the second portion (608) may be open from about below the patient's eye-level with respect to the patient platform (620) since the patient (622) cannot see underneath that point.

As shown in FIG. 6A, the first portion (606) may extend axially through a plane of the radiation beam (614) with the second portion (608) formed just beyond the radiation plane. In this manner, the patient (622) may receive the radiation beam (614) from the rotating first portion (606) while the perception of the enlarged space in the second portion (608) may be maximized. In FIGS. 6A-6B, the first portion (606) may be rotatable while the second portion (608) may be stationary. In these variations, a gap may be formed between the first portion (606) and second portion (608). It should be appreciated that the first portion (606) and second portion (608) may be both rotatable.

The gantry (602) may further comprise a multi-leaf collimator (612) and may be provided opposite a detector (616). The gantry (602) may be coupled to a radiation source (610). In some variations, the radiation source (610) may be mounted to the gantry (602) so as to rotate with a rotation of the gantry (602) about the patient (622). The radiation source (610) and collimator (612) may be configured to emit a radiation beam (614) in a plane perpendicular to a longitudinal axis of the patient platform (620).

In some variations, such as for an open-bore, rotatable gantry, the radiation source (610) may comprise a magnetron mounted on a rotatable ring of the first portion (606) of the gantry (602) (not shown). In other variations, such as for a closed-bore, rotatable gantry, the radiation source (610) may comprise a klystron that is not mounted on a rotatable ring of the first portion (606) of the gantry (602). The klystron may instead be mounted on a stationary frame of the gantry (602), and/or may be mounted separate from the gantry (602). A stationary klystron may provide higher-energy, higher-power and better reliability as compared to a magnetron that is mounted on a rotatable ring.

In some variations, one or more of visual, audio, and tactile sensory inputs may be provided to a patient (622) to simulate an enlarged space within the bore (604). In some variations, the radiotherapy device (600) may provide sensory output (e.g., visual, auditory, touch) configured to create the illusion of an enlarged space. For example, a display of an outdoor setting may be projected within a patient's visual field on the walls of the bore in combination with audio output of nature sounds and airflow over a patient's face. In some examples, the images displayed may change based on where the patient's eyes are looking using an optical eye tracker. The sensory output may be modified using the optical eye tracker data. Such sensory outputs may be used in open-bore systems as well as closed-bore systems, as patients in open-bore systems may also experience discomfort due to claustrophobia due to the length of the bore (i.e., the patient's head does not generally exit the bore during diagnostic or treatment session(s)).

In some variations, the gantry (602) may comprise one or more image projectors (630) disposed within the bore (604) of the gantry (602) and configured to illuminate (631) (e.g., provide lighting, images, video) an interior surface (e.g., ceiling) of the second portion (608) of the bore (604) within the patient's field of view. For example, FIG. 6B depicts an outdoor waterfall scene illuminated (631) on an interior surface of the second portion (608). The images displayed on the hemispherical shape of the second portion (608) may create the illusion of an enlarged space sufficient to reduce claustrophobia in the patient (622). In some variations, a lower resolution and/or unfocused image may be displayed on regions of the second portion (608) corresponding to the peripheral vision of the patient (622) to aid a user in maintaining their head in a fixed position. Similarly, an amount of illumination (e.g., lumens) may be maximized for a patient's central vision and progressively reduced radially outward from this position (e.g., towards a peripheral vision). In some variations, the position of the image displayed on an interior surface of the second portion (608) of the bore (604) may vary with a position of the patient (622) as the patient platform (620) translates and/or rotates through the bore (604). Additionally or alternatively, the interior surface of the second portion (608) of the bore (604) may comprise one or more displays (e.g., LED, OLED, LCD, CRT, etc.).

In some variations, an audio device (632) may be disposed anywhere within a bore (604) to output audio to a patient (622) to, for example, help create the illusion of an enlarged space in the bore (604). For example, an audio device (632) may be mounted to a stationary portion of the gantry (602) within one or more of the first portion (606) and second portion (608). The audio device (632) may comprise one or more speakers. The audio output by the audio device (632) may correspond and/or synchronized to illumination output by the image projector (630). For example, the waterfall images displayed to a user in FIG. 6B may be accompanied by corresponding waterfall noises that may add white noise and reduce the perception of noise from gantry (602) operation. As another example, an audio output may further comprise an echo to simulate an enlarged space. Additionally, the speakers may further output a noise cancellation signal, as discussed in more detail below.

In some variations, an airflow device (636) may be disposed in the bore (604) to direct airflow form a predetermined direction over a desired portion of the patient (622), such as a patient's face. In some variations, the airflow device (636) may comprise one or more fans disposed in the second portion (608). The fans may draw in air from within the bore (604) or externally with respect to the gantry (602). In some examples, the airflow device (636) may be coupled to an air conditioning system to provide cooled air to the patient (622). The airflow device (636) may provide positive or negative pressure.

In some variations, an optical eye tracker (634) may be disposed at any location within the bore (604) having a clear line of sight to a patient's eyes. The optical eye tracker (634) may comprise a non-contact optical sensor configured to determine eye gaze and/or eye position using one or more of corneal reflection, infrared, pupil tracking, etc. In some variations, an image projected by an image projector (630) may be repositioned based on the detected eye gaze and/or eye position from the optical eye tracker (634). In this manner, the patient (622) may be able to comfortably view images without moving their head.

Figure 6C:
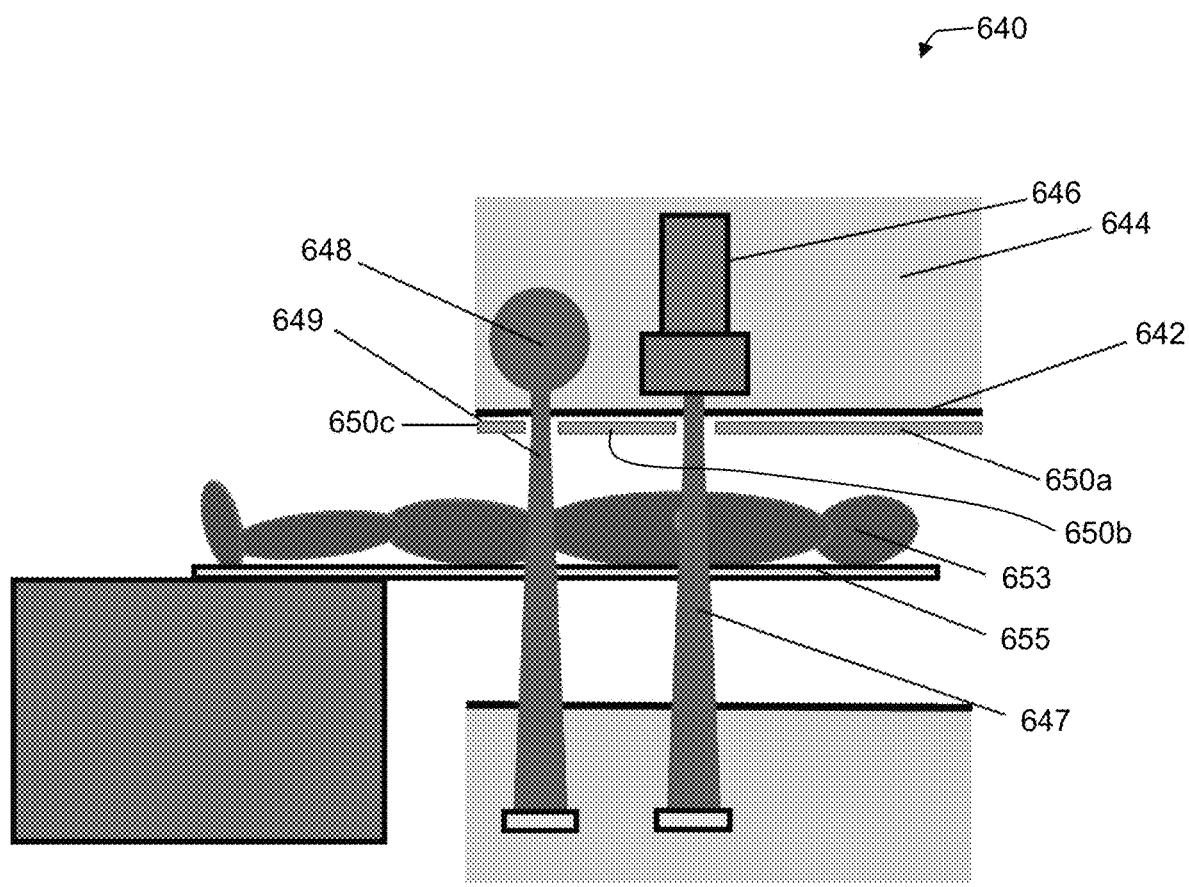
FIG. 6C is a schematic side view of one variation of a gantry with an in-bore display.
Figure 6D:
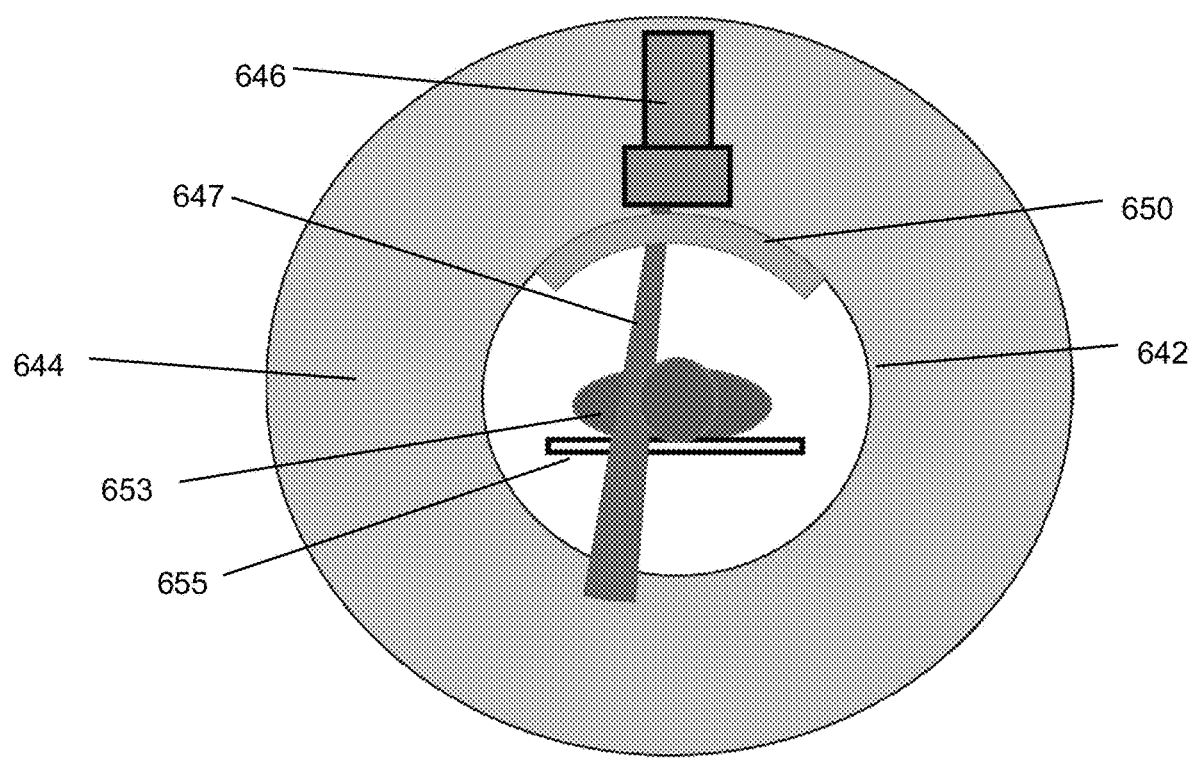
FIG. 6D is a front view (end view) of one variation of a gantry with an in-bore display.
Figure 6E:
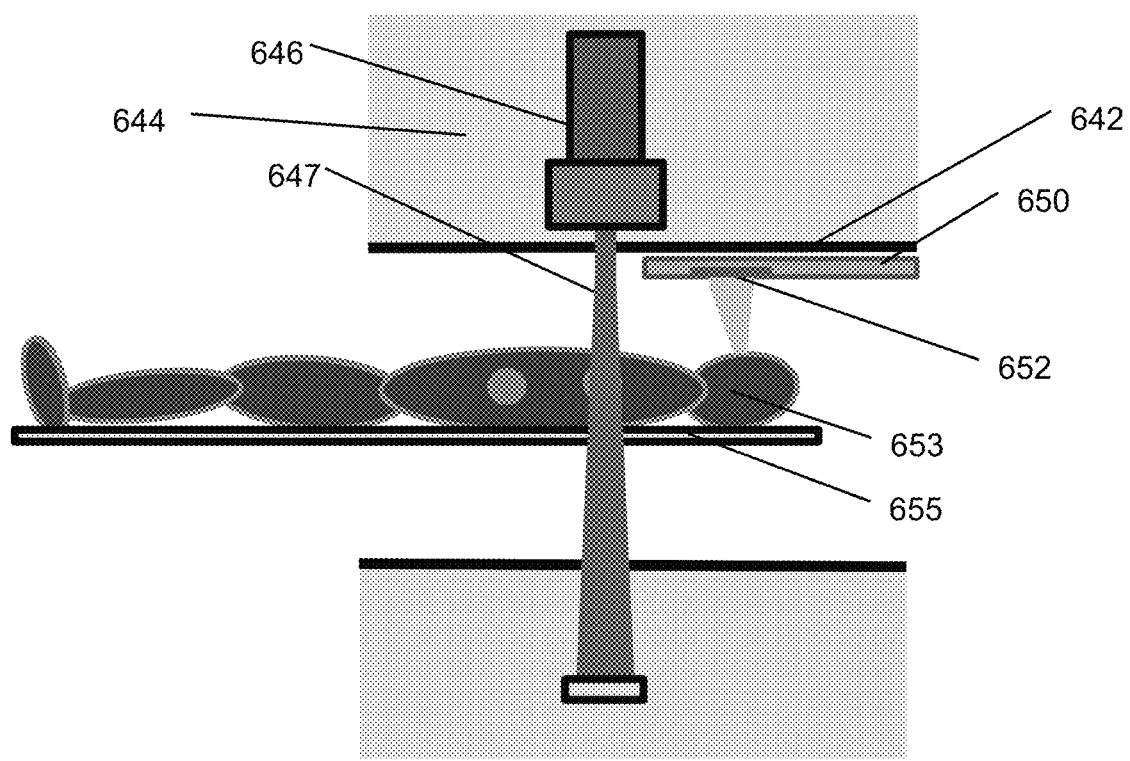
FIGS. 6E-6F are schematic side views of one variation of a gantry with an in-bore display.
Figure 6F:
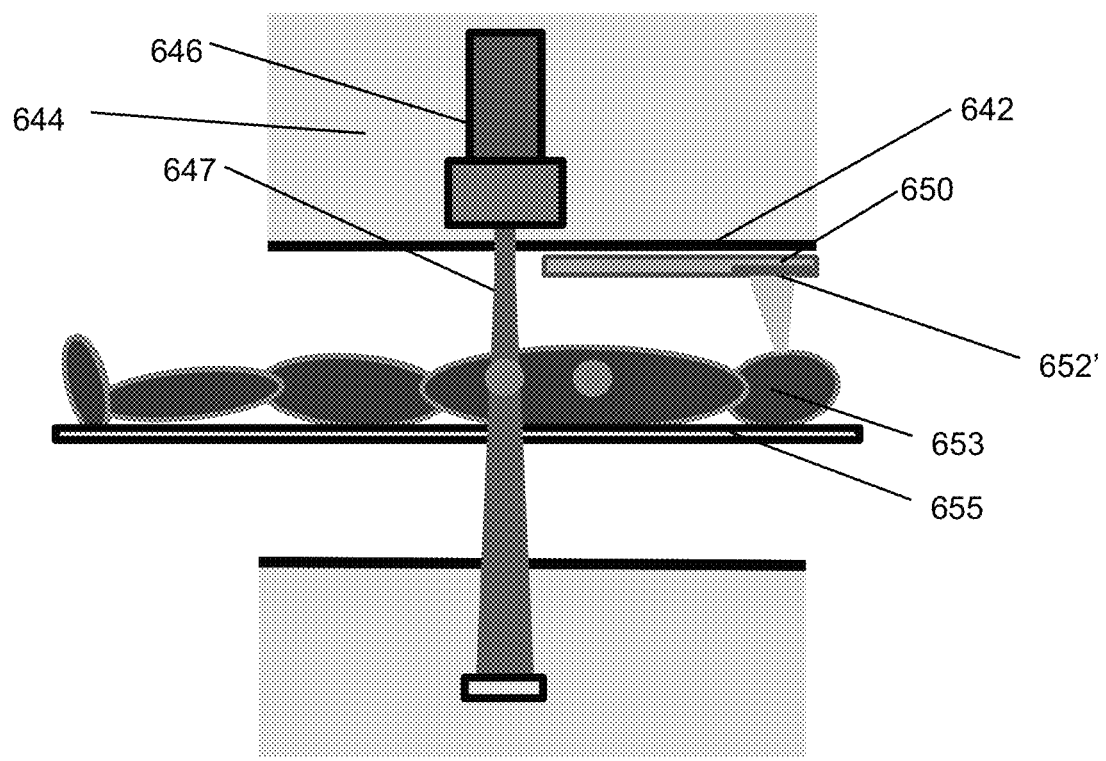

In one variation, a radiation therapy system may comprise one or more visual displays located within the bore. An image presented on the display may be moved along the bore as the patient is moved (by the couch) during a treatment session. Detected eye gaze and/or eye position from an optical eye tracker may optionally be used to move images along the bore so that the image is constantly within the visual field of the patient without requiring patient head motion. In some variations, the displays may be flexible displays that may be mounted along an interior surface of the bore such that they follow the curvature of the bore. For example, the displays may be organic light-emitting diode (OLED) displays. FIG. 6C depicts a cross-section of one variation of a radiation therapy system comprising one or more displays within the bore. The radiation therapy system (640) may comprise a rotatable gantry (644) with a longitudinal bore (642) extending through the gantry, a linac (646), a kV radiation source (648), and a plurality of displays (650a, 650b, 650c) mounted along the length of the bore (642) across from a couch top (655). The linac (646) may generate a therapeutic treatment beam (647) and the kV radiation source (648) may generate an imaging beam (649) that is at a different longitudinal location along the bore than the therapeutic treatment beam. The displays (650a, 650b, 650c) may be flexible displays that are have curvable according to the curvature of the bore (642), and may be, for example, OLED displays. The displays (650) may be mounted along the length of the bore except for the areas of the bore that are within the therapeutic treatment beam path or the imaging beam path. Avoiding the radiation beam paths may help prolong the life of the displays (650). FIG. 6D depicts an end view of the system of FIG. 6C, and as depicted there, the flexible display (650) may span across an arc that corresponds with a patient's visual field. The display (650) may span across from about 25% of the bore circumference to about 50% of the bore circumference, e.g., about 30% of the bore circumference. FIGS. 6E and 6F depict one variation of a system comprising a flexible display (650) located within the bore (642) where one or more images on the display track the position of the patient's eyes. For example, as the patient is moved from a more superficial location (FIG. 6E) to a deeper location (FIG. 6F) within the bore, an image (652) on the display (650) while the patient is at the superficial location may be replaced with another image (652') on the display (650) when the patient is moved to the deeper location. A series of images from the first image (652) to the second image (652') may be generated to create the illusion that the image is moving from one location to another. The location of the images on the display may be determined by the couch position, and/or optical eye tracker data, as described previously.

Audio System

The various components of the radiation therapy system, for example, the rotating gantry, movement of collimator leaves, temperature control systems, and other high-voltage components, may produce significant levels of mechanical noise. This mechanical noise may be amplified within the constrained confines of a gantry bore in which the patient is disposed. For example, operation of the gantry may generate a consistent background hum, along with intermittent mechanical and electrical noise associated with activation of one or more subsystems such as mechanical noise associated with the MLC leaf movement activated during therapy beam delivery. Elevated auditory noise levels may detract from patient comfort and may increase patient anxiety, which may result in patient movement (e.g., fidgeting, body repositioning, increased breathing rate, etc.). Reducing auditory discomfort may thus improve patient comfort and compliance. Noise cancellation headphones and other wearable solutions for noise management may interfere with, and/or may be damaged by, treatment beams. In some variations, a radiation therapy system may comprise an audio system mounted on the gantry, outside of the therapeutic and/or imaging radiation beam path. An audio system may comprise an array of microphones and speakers configured to use patient position data to produce noise-cancelling audio at the patient's ears as the patient moves though the bore of the gantry and/or receives radiation therapy treatment. A controller in communication with the microphone and speaker array may use methods based on phased array theory to map the machine noise, calculate a noise cancelling signal based on patient location data, and project the appropriate amplitude and phase of the noise cancelling signal from the speaker array. Generally, a processor may be configured to receive the ambient sound, generate a waveform signal that is the exact opposite of the ambient sound, and mix it with any desired audio signal to be output to the patient. For example, the noise cancelling signal may be 180° out of phase with equal amplitude as the noise received by the patient's ears.

Figure 7:
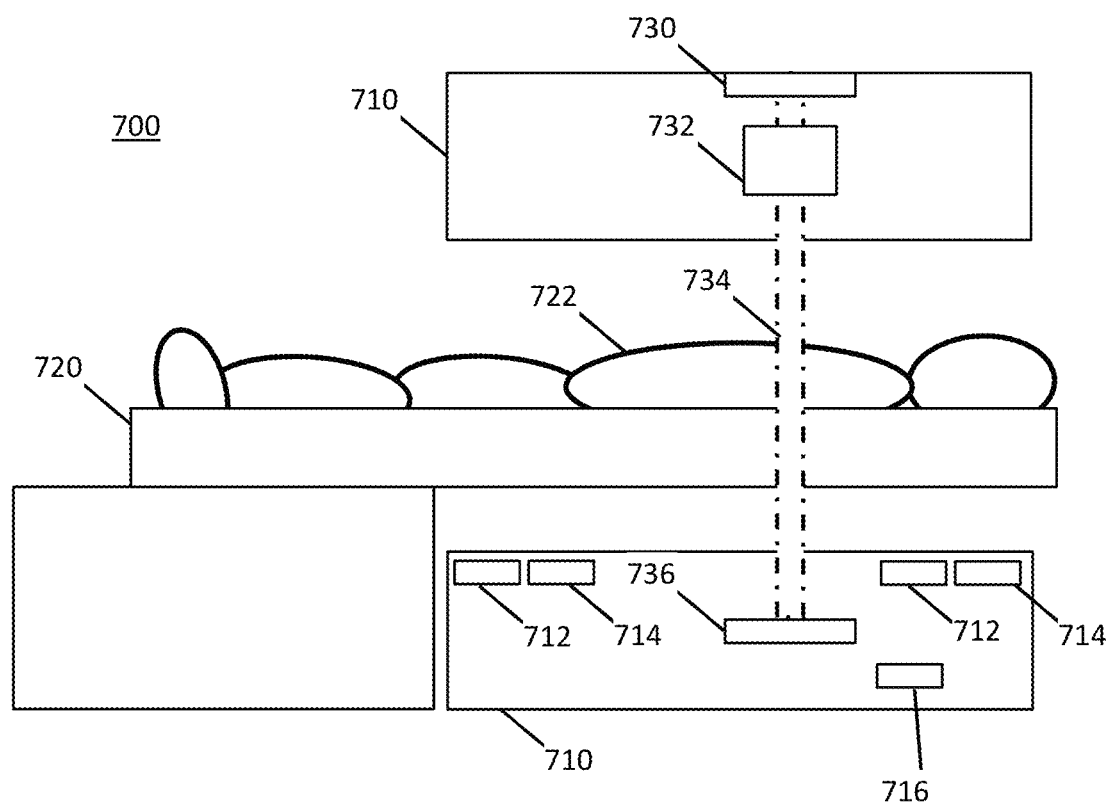
FIG. 7 is an illustrative cross-sectional view of a variation of a radiation therapy system.

FIG. 7 depicts one variation of an auditory noise management system that may be used with any of the radiation therapy systems described herein. In particular, a radiotherapy system (700) is illustrated in FIG. 7 and comprises a gantry (710) comprising a radiation source (730) coupled to a multi-leaf collimator (732). A detector (736) may be provided opposite the multi-leaf collimator (732) and receive a radiation beam (734) output from the collimator (732) and radiation source (730). The gantry (710) may comprise a patient region with a bore of the gantry (710) configured to receive a patient (722) on a patient platform (720). The gantry (710) may further comprise a speaker array (712) and microphone array (714) within the patient region and disposed on a stationary frame (not shown) of the gantry (710). As depicted in FIG. 7, the speaker array (712) and microphone array (714) may be disposed in one or more ends of the gantry (710). In some variations, one or more of the speaker array (712) and microphone array (714) may be disposed on an inner radial surface of a stationary frame within the bore of the gantry (710) near the patient's ears. Additionally or alternatively, one or more of the speaker array (712) and microphone array (714) may be disposed outside the bore of the gantry (710), such as, for example on an external surface of the gantry (710) opposite the inner radial surface.

In variations where the microphone array (714) is located away from a patient's ears, a noise cancellation signal generated based on the sound received at the microphone array (714) may be out of phase such that the detected ambient noise is not effectively cancelled where the patient (722) is located. Accordingly, a processor may generate a noise cancellation signal that also compensates for differences in location between the patient's ears, speaker array, and microphone array. For example, the gantry (710) may comprise a controller having a processor (716) configured to receive patient location data from a patient location system and generate a noise cancellation signal using the audio received by the microphone array (714) and patient location data. The processor (716) may use the patient location data to compensate for the difference between the microphone location and the patient ear location when generating the noise cancellation signal. The speaker array (712) may be configured to output the noise cancellation signal.

Accordingly, the system (700) may further comprise a location determination system configured to locate the patient (and their ears) in the patient region. In some variations, the location determination system may use patient position registration data (e.g., from PET imaging, kV CT imaging) to determine a location of a patient's ears. In other variations, the patient (722) may be positioned along the patient platform (720) at a predetermined position such that the ear location is known. For example, the patient (722) may be coupled to a fixed location on the patient platform (720) such as by a head fixation device. Once the patient's ears have been located, the processor (716) may generate a noise cancellation signal that compensates for any differences between the location of the patient, speaker array (712), and microphone array (714).

Additionally or alternatively, the speaker array (712) may be used to output audio in the bore of the gantry (710) for the patient (722) to increase patient comfort and reduce anxiety. For example, the processor (716) and speaker array (712) may be configured to output voice audio (e.g., live operator voice, prerecorded voice) providing treatment status and/or other information. Providing audio to the patient (722) may occupy the patient's attention during a radiation therapy procedure and may be useful during long treatment sessions (e.g., 20 minutes, 30 minutes, 60 minutes). In other examples, the processor (716) and speaker array (712) may output one or more of music, white noise, natural sounds, and other sounds to reduce the perception of mechanical noise generated by a radiotherapy system.

Collimator System

As described previously, radiation therapy systems may comprise a multi-leaf collimator disposed in the beam path of the MV X-ray source or therapeutic radiation source. In some variations, the multi-leaf collimator may be a binary multi-leaf collimator, such as any of the binary multi-leaf collimators described in U.S. patent application Ser. No. 15/179,823, filed Jun. 10, 2016, which is hereby incorporated by reference in its entirety. In one variation, the multi-leaf collimator may comprise a plurality of leaves and a corresponding number of pneumatic leaf actuation mechanisms. Each leaf actuation mechanism may be configured to independently move its corresponding leaf, and a compressed air source may be coupled to one or more of the pneumatic leaf actuation mechanisms. Each of the pneumatic leaf actuation mechanisms may comprise a barrel comprising a longitudinal lumen, a first side opening, and a second side opening, and a piston that extends within the longitudinal lumen of the barrel. The piston may comprise a shaft and a piston seal coupled to the shaft within the barrel, where movement of the piston within the barrel translates the collimator leaf between the first location and the second location. The first and second openings may be fluidly connected to a compressed air source. The pneumatic mechanism may further comprise a first valve between the first opening and the fluid source and a second valve between the second opening and the compressed air source. The first and second valves may selectively regulate fluid flow into and out of the barrel lumen. Compressed air may be distributed to each of the leaf pneumatic mechanism barrels (one for each leaf) via a grid or array of air conduits, where each valve of each pneumatic leaf actuation mechanism may be individually controlled to regulate the air flow into each barrel. The compressed air supplied to each pneumatic leaf actuation mechanism is provided by an air supply grid that comprises separately and independently-controlled valves (i.e., first and second valves of a plurality of pneumatic leaf actuation mechanisms). The compressed air within the air supply grid may be provided by a compressor or compressed air source mounted on the rotatable ring of the gantry. Compressed air sources mounted on a rotatable gantry, such as a high-speed, continuously-rotating gantry may be subject to elevated levels of vibrations as compared to air sources mounted on non-rotating (or slow-speed) gantries. A high-speed gantry may comprise a scroll or screw compressor, which may be less susceptible to vibrations and sounds as compared to a piston compressor. In some variations, the scroll or screw compressor may be mounted on vibration-isolating feet on the rotatable ring and may be configured to convert ambient air having a pressure of about 1 ATM to pressurized air having a pressure of about 10 ATM. Some variations of an on-board compressor system may comprise accumulator tanks, filters, dryers, and after-coolers. Systems that comprise an optional kV radiation source for imaging and/or patient position registration may comprise a similar multi-leaf collimator having pneumatic leaf actuation mechanisms, which may be driven by the same or different compressed air system as for the MV X-ray source or therapeutic radiation source.

Generally, a therapeutic radiation beam may be generated by a linac and shaped by one or more beam shaping components. In some variations, the one or more beam shaping components may comprise one or more of the following: a primary collimator, a secondary collimator, a multi-leaf collimator, a first jaw, and/or second jaw. A primary collimator and/or a secondary collimator may comprise a fixed beam-shaping aperture (e.g., shape and/or size of the aperture is constrained to a predetermined shape or size) or a variable beam-shaping aperture (e.g., shape and/or size of the aperture may be varied as desired before, and/or during and/or after treatment). In some variations, the primary collimator may comprise a tungsten substrate or base with a trapezoidal-shaped slot that may define a general shape of the radiation beam. Similarly, the first jaw and/or second jaws may comprise a fixed beam-shaping aperture or a variable beam-shaping aperture. The collimators and/or jaws may shape the beam along two axes (e.g., x-axis and y-axis) or may shape the beam along one axis (e.g., x-axis only or y-axis only). The multi-leaf collimator may be configured to shape the beam along two axes (e.g., x-axis and y-axis), and/or may be configured to shape the beam along one axis (e.g., x-axis only or y-axis only). An X-ray beam emitted by a linac may result from accelerating electrons into a target (such as a tungsten target), which then converts the energy from the electron-target collision into an X-ray beam. For a system comprising a linac mounted on a rotatable ring (e.g., a continuously rotatable ring), the electron source (e.g., an electron gun), the microwave source (e.g., a magnetron), the pulsed power source and the RF circulator may be provided on a rotatable ring of a gantry.

The radiation therapy system (800) may further comprise a target converter comprising a target and a primary collimator, a dose chamber, upper jaws, a multi-leaf collimator (e.g., a binary MLC), and lower jaws. The primary collimator, upper jaws, the binary MLC, and lower jaws may shape the radiation beam emitted by the linac. The upper and lower jaws may move on curved rails that loosely focus to the virtual point spot of the target converter.

Figure 8A:
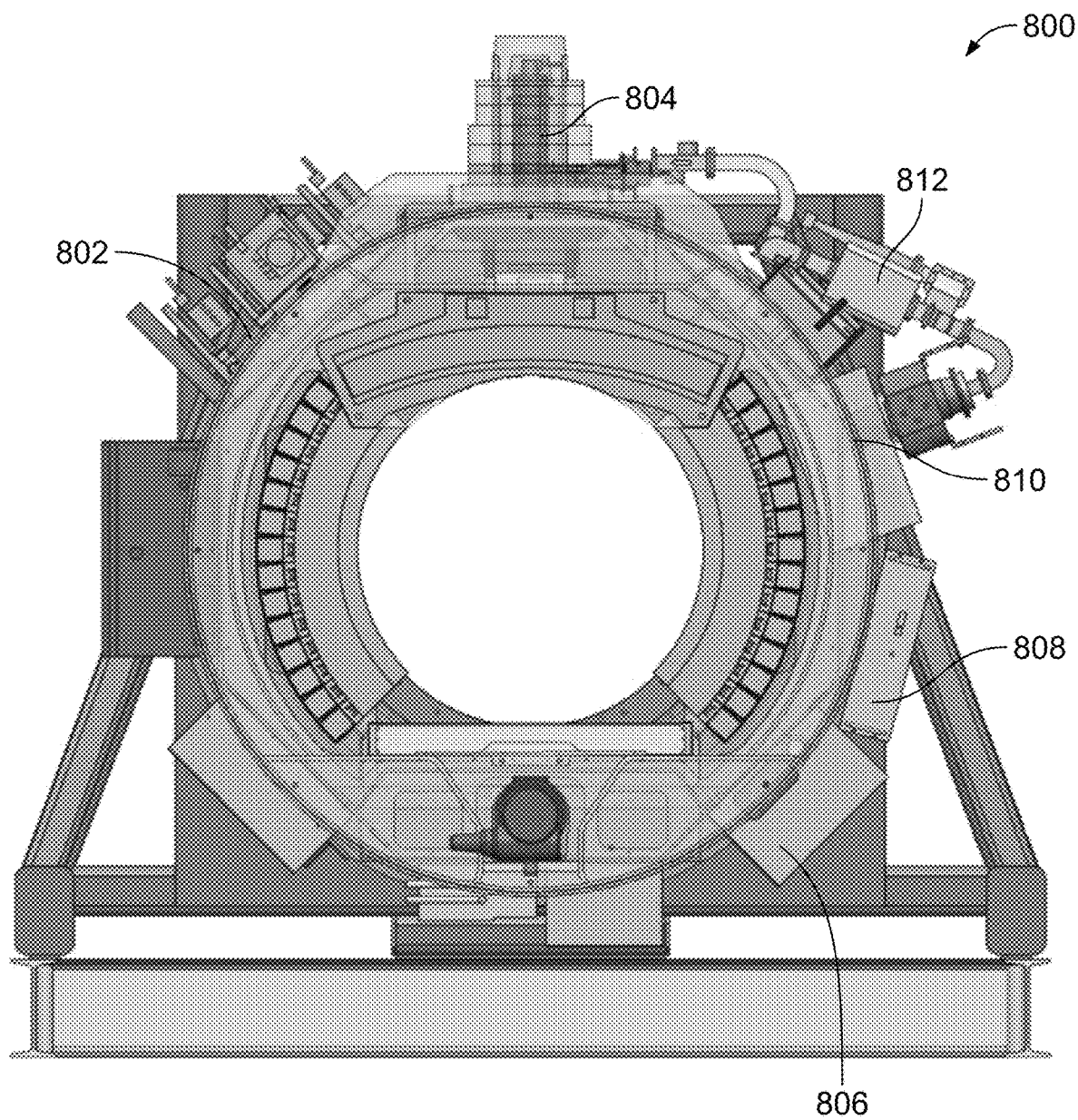
FIG. 8A is a front view of the gantry.

FIG. 8A depicts one variation of a radiation therapy system (800) comprising a rotatable gantry (802), a linac (804) configured to emit a therapeutic radiation beam, a pulsed power supply (806), an electron gun (808), a magnetron (810) and a RF circulator, where the linac, pulsed power supply, electron gun, magnetron and RF circulator are mounted on a rotatable ring of the gantry. The pulsed power supply (806) may be connected to the electron gun (808), which may generate pulses of electrons that correspond with the temporal characteristics (e.g., frequency, duty cycle, etc.) of the power pulses from the supply (806). The microwaves generated by the magnetron (810) and the RF circulator accelerate electrons from the gun (808) in the waveguide of the linac (804).

Figure 8B:
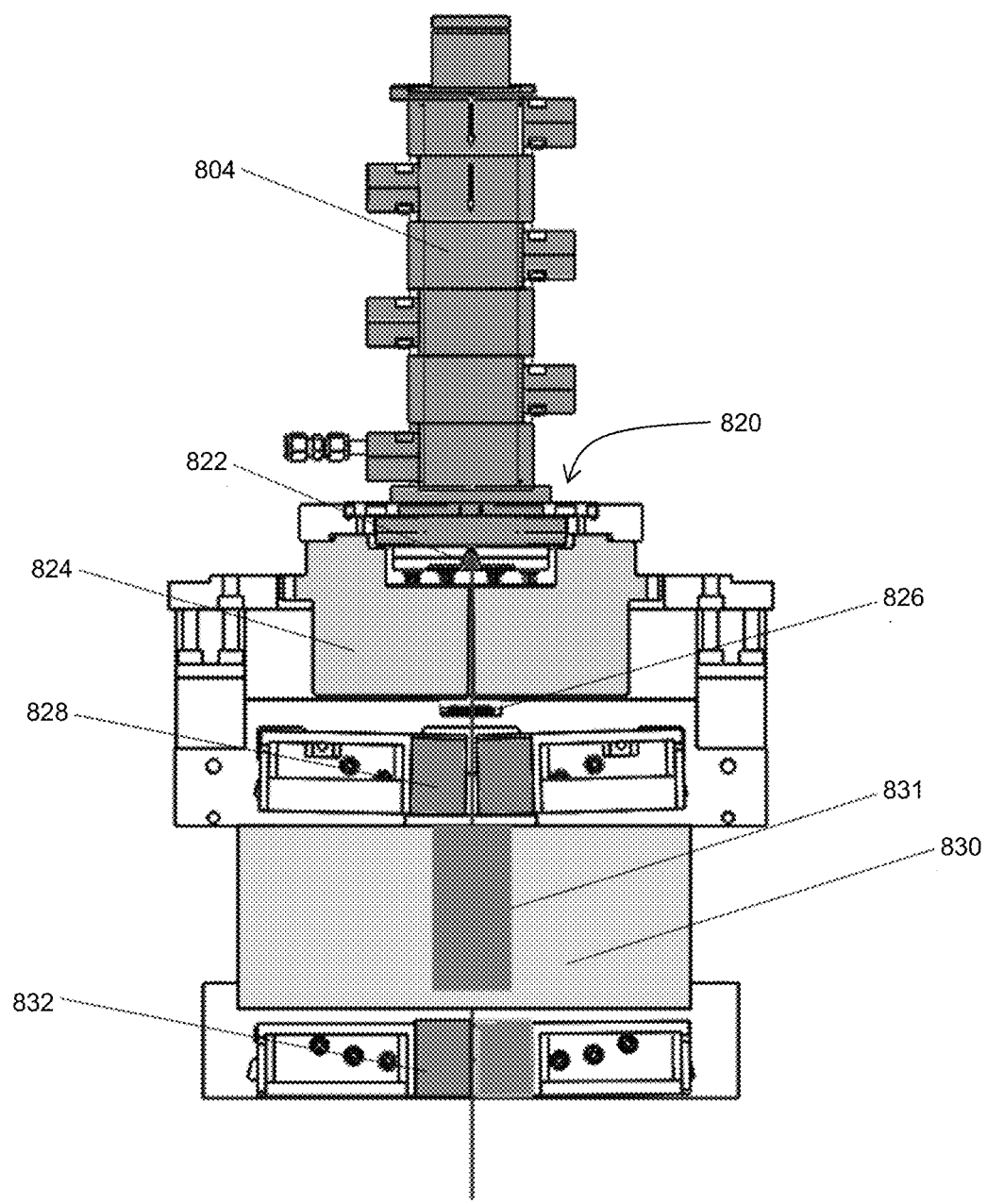
FIG. 8B is a cross-sectional front view of one variation of the radiation beam path and beam-shaping components mounted on the gantry of FIG. 8A.
Figure 8C:
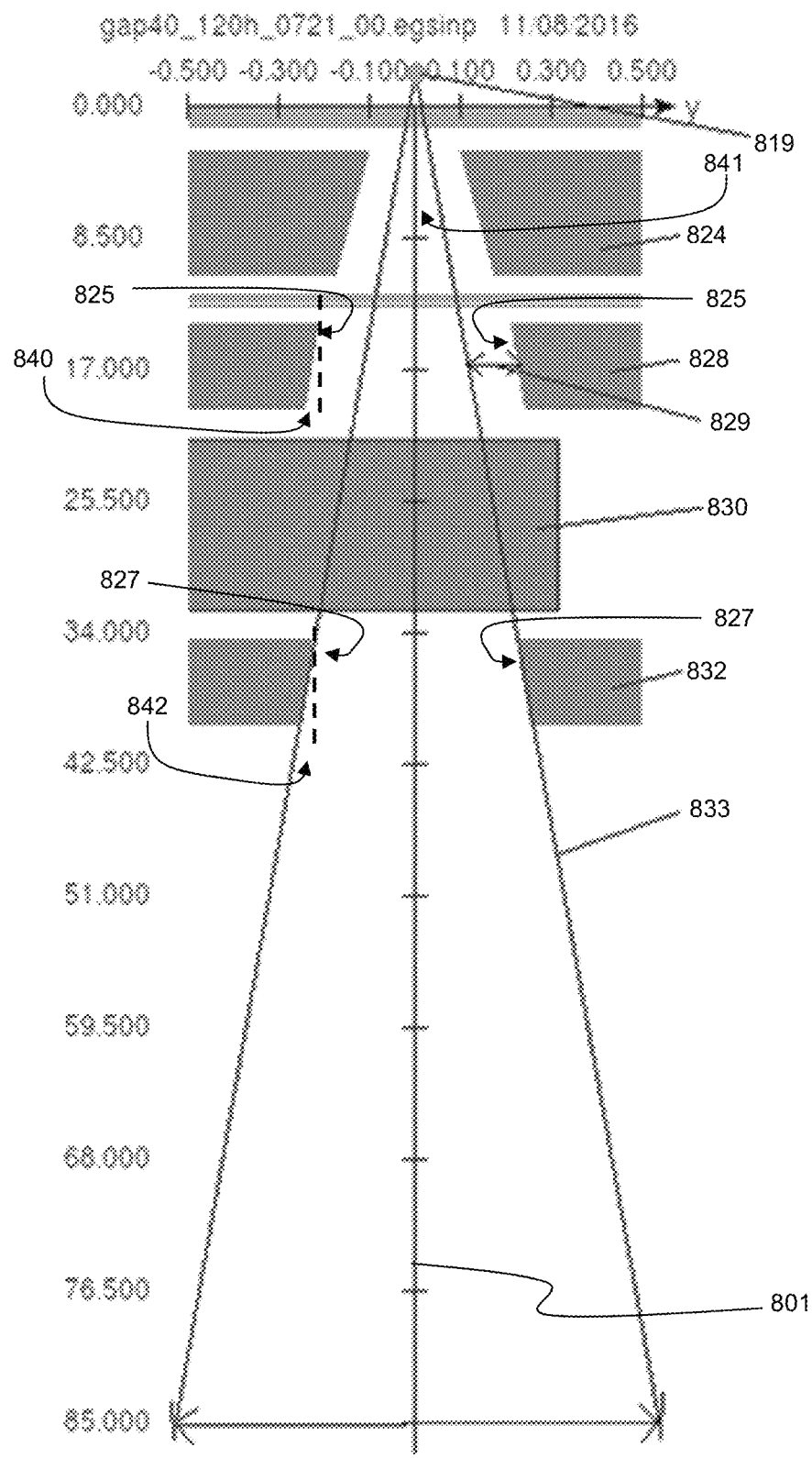
FIG. 8C is a schematic cross-sectional view of the radiation beam path and beam-shaping components of FIG. 8B.
Figure 8D:
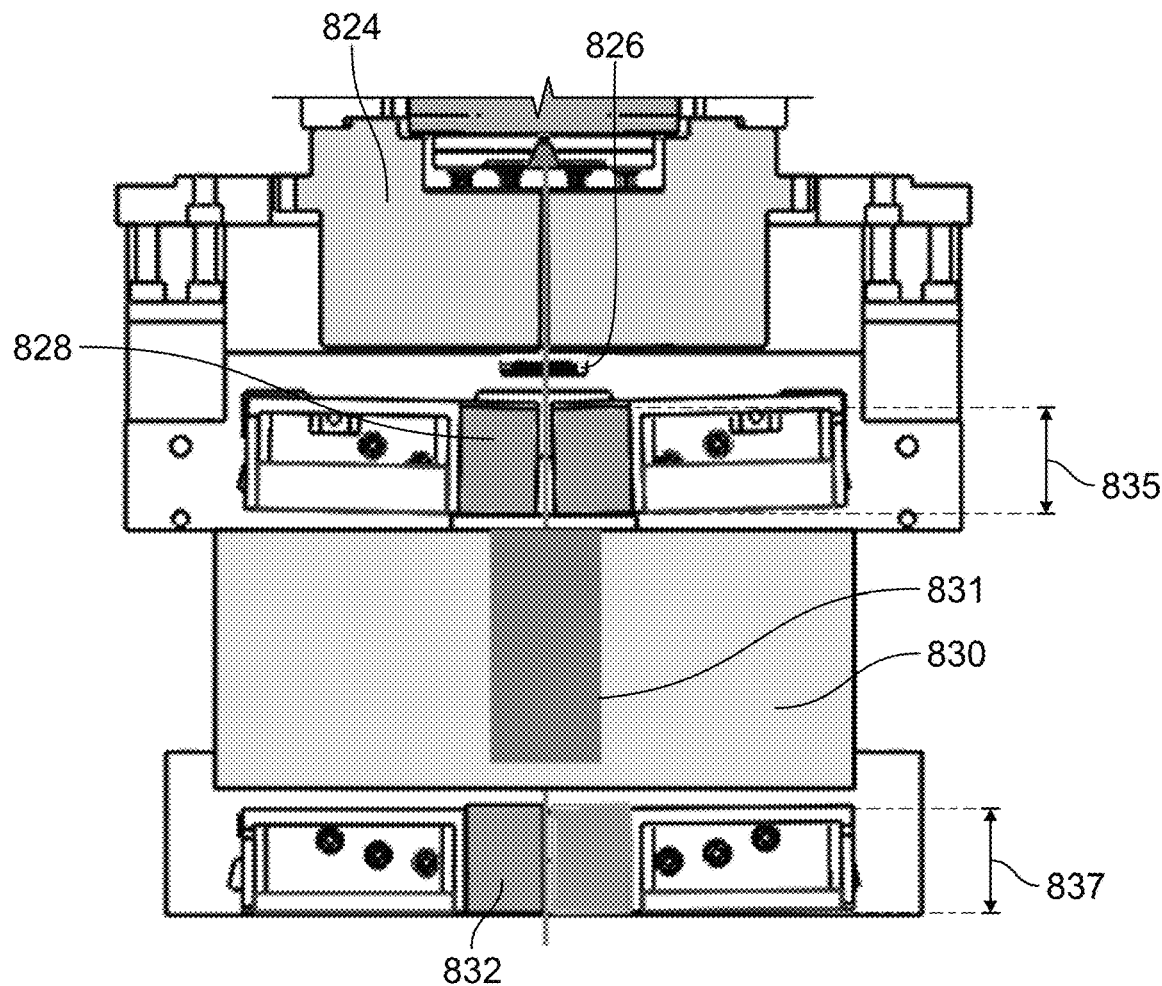
FIG. 8D is a close-up view of the radiation beam path and beam-shaping components of FIG. 8B.

FIG. 8B depicts one variation of a radiation beam path. The accelerated electrons from the linac (804) may collide with a target (822) (e.g., made of tungsten) of a beam converter (820), converting the energy from the collision into an X-ray radiation beam. The radiation beam is first shaped by a primary collimator (824), passes through a dose chamber (826), and then is shaped by an upper beam-limiting block or jaws (828) along a first axis (e.g., y-axis), shaped by the leaves of the binary MLC (830) along a second axis (e.g., x-axis), and finally shaped by a lower beam-limiting block or jaws (832) along the first axis (e.g., y-axis) before the radiation beam enters the patient treatment area. The primary collimator (824) may be directly mounted to the rotatable ring and aligned to the isocenter of the radiation therapy system. FIG. 8D depicts a close-up view of the beam-limiting components in the radiation beam path. More generally, the size and shape of the opening(s) or slot(s) in one set of collimators or jaws may define the radiation beam in one axis (e.g., the x-axis) while the size and shape of the opening(s) or slot(s) in another set of collimators or jaws may define the beam along another axis (e.g., the y-axis). One aspect of these beam limiting devices is how well they create a gradient from full radiation beam to fully attenuated radiation beam; full attenuation may be a function of material thickness and the radiation blocking ability of that material (Half Value Layer attenuation) and may be referred to as the penumbra. In some examples, penumbra may be defined as the distance between the 80% radiation level and the 20% radiation level along this gradient and in some other examples, penumbra may be defined as the distance between 90% and 10% radiation levels. A smaller penumbra may allow for a sharper beam edge, such that a greater portion of the beam has a uniform fluence (e.g., a flatter beam profile) as compared to a beam with a larger penumbra. Improved beam homogeneity may help increase the precision of the treatment. Since the beam-shaping components for the x-axis and y-axis components are not in the same plane, there may be a tradeoff in improving the penumbra in the x-axis (or y-axis) edge as the cost of enlarging the penumbra in the y-axis (or x-axis) edge. The typical approach is to select for which edge (either the x-axis or y-axis) should the penumbra be smallest and then this beam-shaping component is placed at the bottom (i.e., furthest from the linac, closest to the patient).

One way to balance the quality of the penumbra in both the x-axis and y-axis dimensions is to split the y-axis beam-limiting component so that a first portion of the y-axis beam-limiting component is located above the x-axis beam-limiting component and a second portion of the y-axis beam-limiting component is located below the x-axis beam-limiting component. One variation of a jaw assembly in a split-jaw configuration is depicted in FIG. 8B. As depicted there, the beam-limiting components for the y-axis dimension (i.e., upper jaws (828) and lower jaws (832)) are located above and below the beam-limiting component (i.e., leaves (831) of multi-leaf collimator (830)) for the x-axis dimension. This functionally "splits" the y-axis beam-limiting component such that one portion is above the x-axis beam-limiting component and the other portion is below. The opposing portions of the upper jaws and lower jaws may be independently adjusted such that the opening or slot in the jaws may have different widths. In the variation of FIG. 8B, the upper jaws (828) and the lower jaws (832) can be thought of as a single jaw that has been split so that the upper portion is located above the binary MLC and the lower portion is located below the binary MLC (830). This may result in smaller penumbras in both the x-axis and y-axis dimensions than if the entire y-axis beam-limiting component were located above the x-axis beam-limiting component, or if the x-axis beam-limiting component were located above the y-axis beam-limiting component. As depicted in FIG. 8C, the inward face (825) of the upper jaws (828) may and the inward face (827) of the lower jaws (832) may each be oriented at an angle (840, 842) with respect to a vertical axis parallel to the radiation beam path (801). The angle (840) of the face (825) of the upper jaws (828) may be larger than the angle (842) of the face (827) of the lower jaws (832). For example, the angle (840) may be about from about 0.3 degrees to about 2 degrees as the IEC Y field size ranges from 1 cm to 5 cm, while the angle (842) may range from about 0.8 degrees to about 8 degrees as the IEC Y field size range from 1 cm to 5 cm. The angles (840, 842) may be determined at least in part on the desired field size (e.g., about 1 cm to about 5 cm) at a plane (e.g., isocenter plane) located at a desired distance (e.g., about 85 cm) from a radiation source (e.g., a point or virtual source), and/or the thicknesses (835, 837) of the upper and lower jaws, and/or the size (e.g., width) and shape of the opening or slot of the primary collimator (824), and/or radiation source or beam energy, and/or other beam-generating or beam-shaping components. In some variations, the angle (840) of the inward face (825) of the upper jaw may be approximately the same as the angle (841) of the focal line (833) with respect to a vertical axis. The focal line (833) of a radiation beam may represent the boundary of the radiation beam spread from a linac (which may be approximated as a point or virtual source (819)). The angles (840, 842) of the inward faces of the upper and lower jaws may be the same as, or different from, the angle (841) of the focal line. For example, the inward face angle (840) may be greater than the focal line angle (841) while the angle (842) may be the same as the focal line angle (841). In some variations, the angles (840, 842) of the inward faces of the jaws may be adjustable.

Figure 8E:
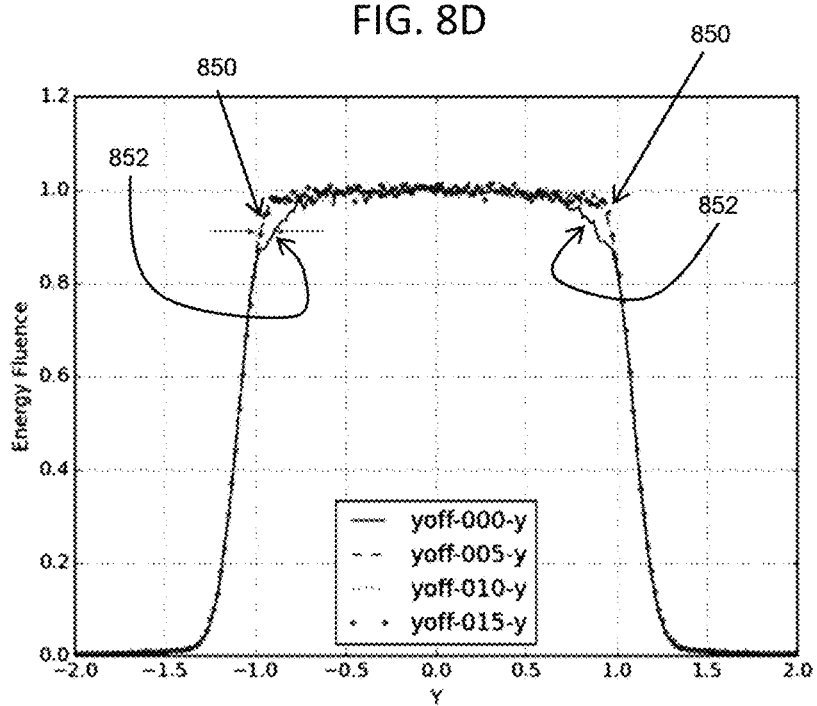
FIG. 8E is a plot of the y-axis radiation dose or fluence profile for different offset values of the upper jaws.

In some variations, the inward faces (825) of the upper jaws (828) may be offset from the focal line (833). That is, the inward faces (825) of the upper jaws (828) may be set back from the focal line (833) by an offset value (829). As depicted in FIG. 8C, the inward faces (827) of the lower jaws (832) may be aligned along the focal line (833), i.e., having an offset value of 0. The inward faces (825) of the upper jaws (828) may be located a distance (i.e., offset) away from the focal line (833), for example, having an offset value (829) from about 0.5 mm to about 2 mm, e.g., about 1 mm. In some variations, the inward faces of the upper and lower jaws are not aligned with each other (i.e., have different offset values). FIG. 8E is a simulation plot of the energy fluence along the y-axis penumbra as a function of the offset of the upper jaws (where the offset of the lower jaws is 0, i.e., the inward faces of the lower jaws is aligned with the focal line). The beam profile where the upper jaw offset is 0.5 mm or more is represented by line (850) and the beam profile where the upper jaw offset is 0 is represented by line (852). The 90% penumbra of a beam where the upper jaws have an offset greater than about 0.5 mm (e.g., about 1 mm) is smaller than the 90% penumbra of a beam where the upper jaws have no offset. That is, the beam attains 90% fluence more rapidly (i.e., sharper slope or edge) when the upper jaws have an offset of 0.5 mm or more than when the upper jaws have no offset or an offset less than 0.5 mm. This indicates a smaller 90%-10% penumbra, calculated as the difference between the beam half widths at 10% level and 90% levels, respectively. A rectangular-shaped beam profile, with sharper beam edges, may improve the dosimetric properties of the beam, because the central portion of the beam (e.g., about 80% of the beam profile) is flatter or more uniform. When there is an non-zero offset of the upper jaws (828) from the focal line (833), the angle (840) and the distance of all the points on face (825) may be calculated such that the upper jaws (828) projects to a slightly larger field size in the place of machine isocenter, due to its offset (829) and larger angle (840) between the face and the central axis. For example, when the lower jaw projects to 2 cm at the isocenter plane, and the upper jaw has an offset of 1 mm from the focal line, the upper jaw then may project to about 2.8 cm field size. The plot in FIG. 8E are simulation results for upper jaws having a thickness (835) of about 55 mm and lower jaws having a thickness (837) of about 55 mm. In some variations, the thickness (835) of the upper jaw may be greater than the thickness (837) of the lower jaw, while in other variations, the thickness (835,837) may be the same, and in either case, may be from about 30 mm to about 70 mm, e.g., about 40 mm, about 55 mm. The offset of the inward faces of the upper jaws and/or lower jaws may be determined by a number of factors, for example, at least in part by the energy level of the radiation beam, the thickness, location and composition of the target, and/or thickness of the upper and lower jaws, and/or distance between the upper and/or lower jaws from the target or virtual source, and/or the thickness of the multi-leaf collimator.

Figure 8F:
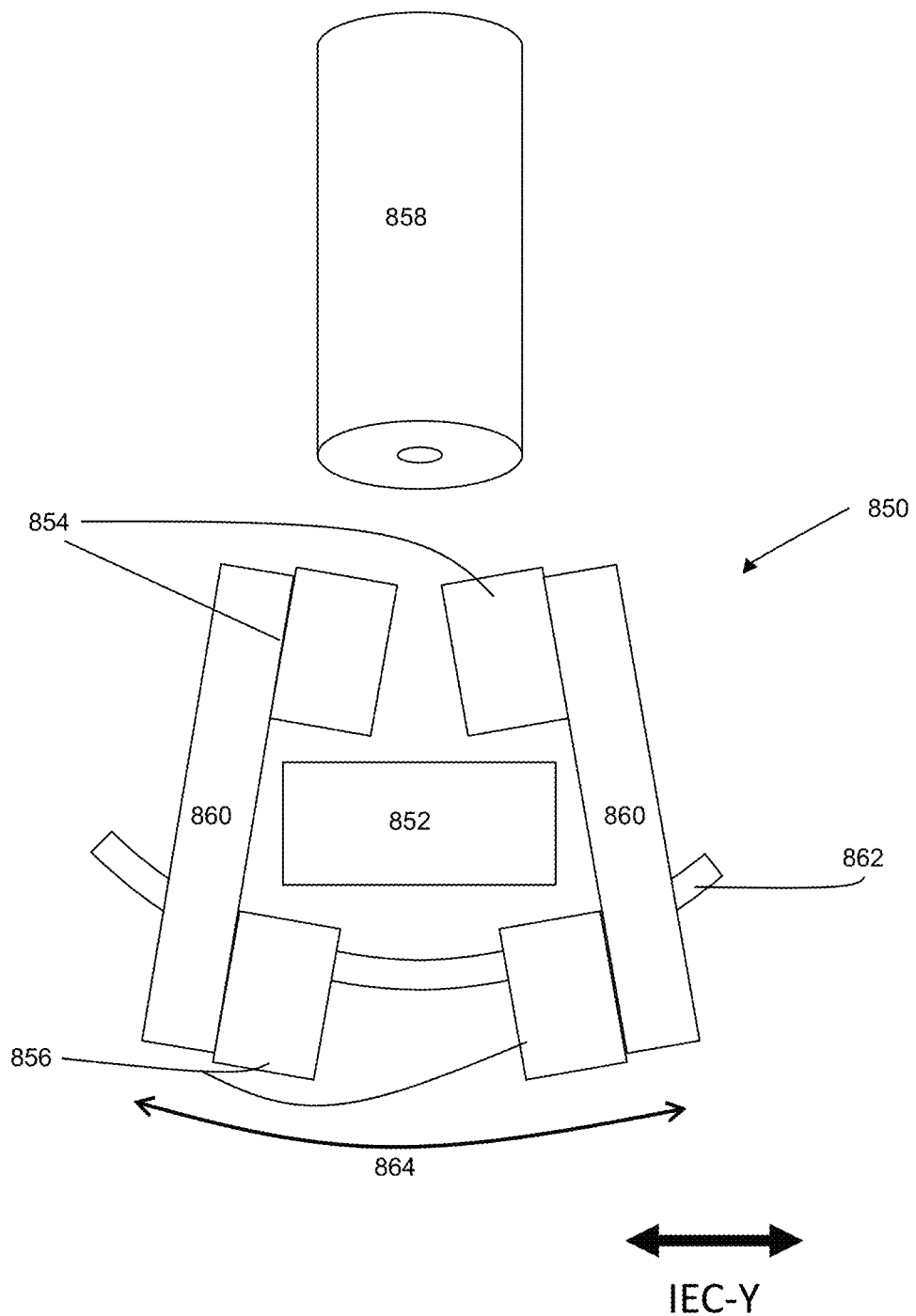
FIG. 8F depicts one variation of beam-shaping components mounted on curved rails.

In some variations, one or more of the beam-shaping components (e.g., the primary collimator, upper jaws, the binary MLC, and lower jaws) may be mounted on curved rails. FIG. 8F is a schematic depiction of one variation of a beam-shaping module comprising a split jaw (850) and a MLC (852). The dynamic MLC (852) may be a binary MLC. The split jaw (850) may comprise upper jaws (854) located between the therapeutic radiation source (858) (e.g., linac) and the MLC (852), and lower jaws (856) located below the MLC (852). The upper jaws (854) and the lower jaws (856) may be coupled together by one or more plates (860) or frames. The jaw may be mounted on one or more curved linear rails. For example, the split jaw (850) may be slidably mounted on one or more curved linear rails (862). The one or more plates or frames of the split jaw may have one or more slots that are sized and shaped to be larger than the cross-sectional size of the rails such that the slots can slide over the rails (as indicated by arrow (864)). Optionally, there may be an additional rail orthogonal to the rail (862) to provide further support to the jaw. The rails (862) are curved in this example, but they may not be curved (i.e., they may be straight, without any curves) in other variations. The jaw may be coupled to an actuator or motor that moves the position of the jaw along the curved linear rail. Movement of the jaw along the rail may result in a corresponding shift of a treatment plane along the IEC-Y axis (i.e., parallel to the axis of motion of the patient platform). In other variations, the jaw may instead be mounted to the gantry via one or more movable or rotatable attachment mechanisms, such as one or more hinges or pivots. The jaw may be able to move from about 0.5 cm to about 2 cm to the right or to the left of the isocenter, with a total range of movement (end-to-end) from about 1 cm to about 4 cm. This may correspond to a similar shift in the treatment plane, where the treatment plane may shift along the longitudinal axis of the patient platform with a total range of movement of from about 1 cm to about 4 cm. It should be understood that the total range of movement along the longitudinal axis of the patient platform (e.g., IEC-Y) may be from about 1 cm to about 12 cm, e.g., about 1 cm, about 2 cm, about 3 cm, etc. In some variations, a binary MLC may comprise 64 leaves that define an axial plane (e.g., IEC-XZ) that are each 0.6 cm in width at isocenter leading to a field-of-view (FOV) of ~40 cm. The jaw actuator may be configured to move the jaw at a speed of about 0.25 cm/s to about 2 cm/s, e.g., about 0.5 cm/s, about 1 cm/s, etc. The jaw actuator may comprise, for example, an electromagnetic actuator. In some variations, the speed of the jaw may be greater than the speed of the patient platform. While the beam-shaping module depicted and described in FIG. 8F comprises a split jaw and a MLC that are not movably attached to each other (i.e., moving or shifting the jaw does not necessarily move to shift the MLC), in other variations, the jaw and the MLC may be movably attached to each other (i.e., the jaw and the MLC move or shift together in concert).

Magnetron

Figure 9A:
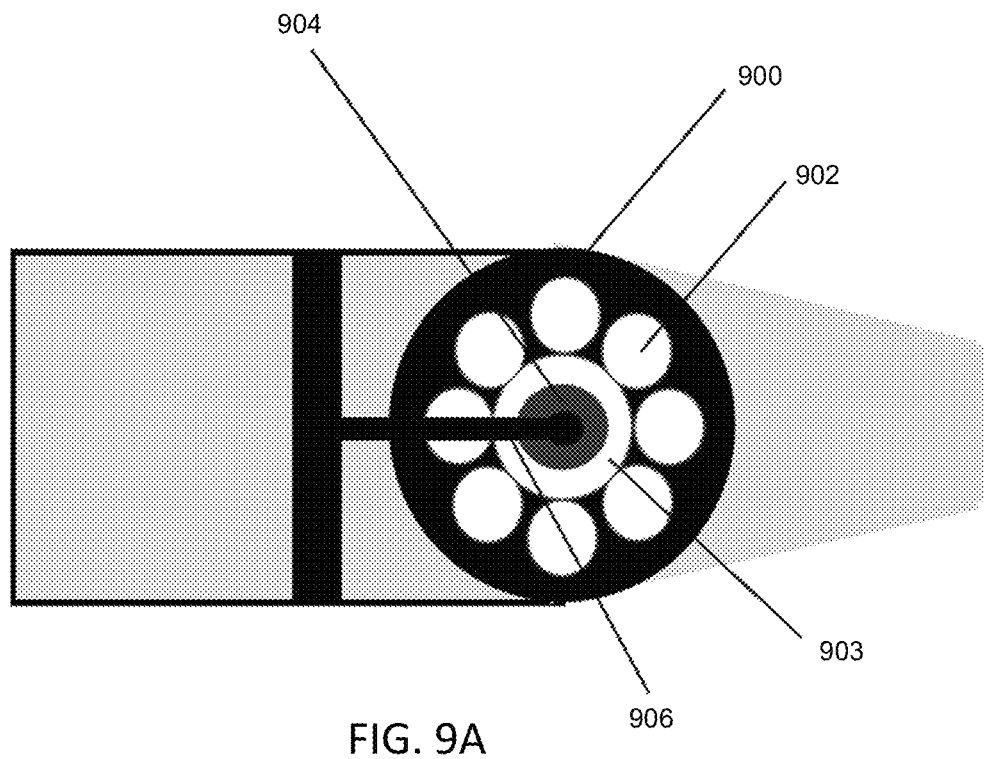
FIGS. 9A-9B are illustrative depictions of a variation of a magnetron.
Figure 9B:
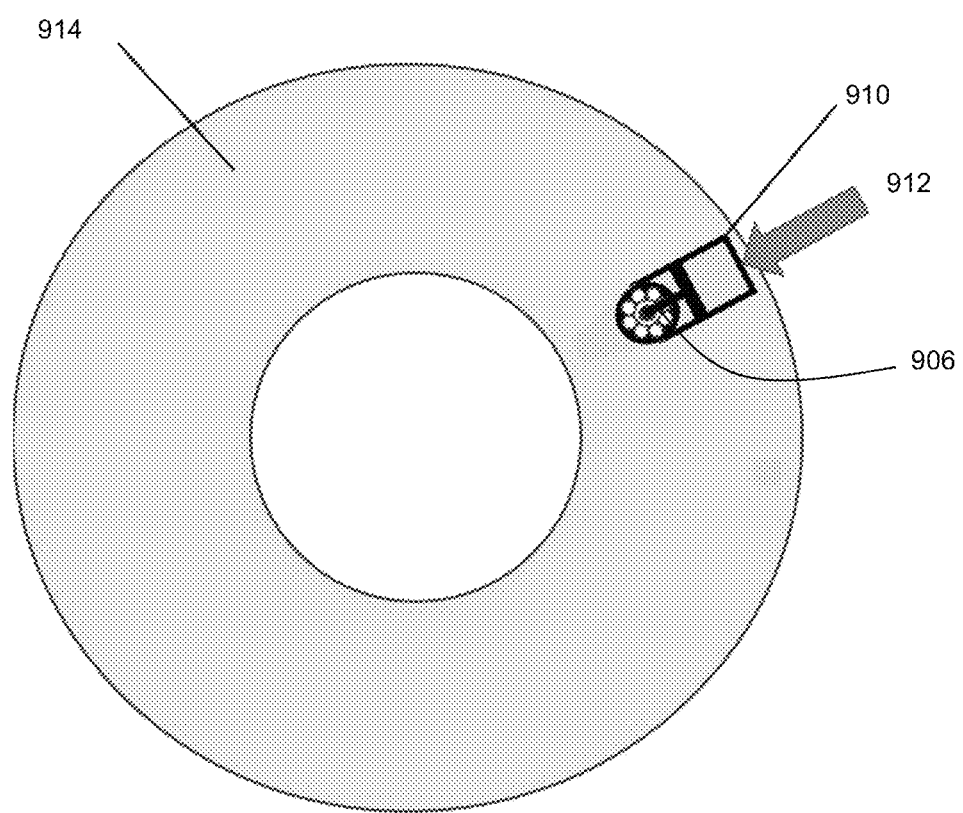

Magnetrons are source devices that convert high voltage, DC power to radio frequency electromagnetic power. As described above, the magnetron may be mounted on the rotatable ring of a gantry. High-speed rotation of the gantry may cause instabilities in the magnetron due to increased levels of centripetal forces as compared to stationary gantries (or gantries that rotate at a slower speed). A magnetron may include a ring anode (900) featuring a cavity structure (902) and a central cathode (904) with a gap (903) therebetween, as depicted in FIG. 9A. The cathode (904) must be supported without interfering with the field structure, and as such, the cathode may be weakly supported by an axle or bracket (906), and/or may not reliably withstand the rotational forces (e.g., centripetal and/or centrifugal) and sinusoidal gravitational forces from the rotating ring, resulting in undesirable movement of the cathode relative to the magnetron. Cathode movement may affect the field structure in the magnetron and may adversely affect its ability to produce RF fields. FIG. 9B depicts one variation where the magnetron (910) is radially mounted, so that the cathode support (906) is aligned with the direction (912) of the centripetal force (e.g., along the radius toward the center of the ring). As shown there, the cathode support or axel (906) may be oriented substantially radially with respect to the rotatable ring (914) of the gantry. In this arrangement, the centripetal force may be relatively constant, and the cathode support (906) may only need to withstand sinusoidal gravitational forces to support the cathode (904). Alternatively, some radiation therapy systems may comprise a klystron mounted on the rotatable ring, instead of a magnetron.

Beam Converter

Figure 11:
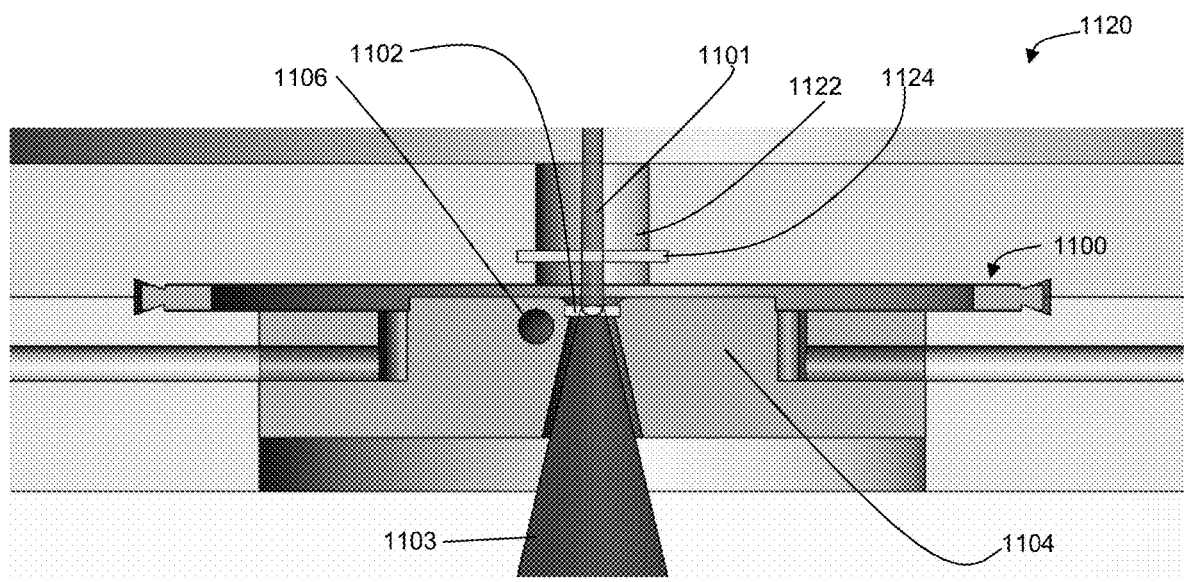
FIG. 11 is an illustrative depiction of a variation of a beam converter.

The magnetron may accelerate electrons from an electron source (e.g., an electron gun) to create an electron beam. This electron beam may be directed through the cavity of a linac to a beam converter comprising a hi-Z material, such as tungsten or tantalum. Collision of the electrons in the beam converter results in the emission of high-energy photons (e.g., X-ray beam). One variation of a beam converter assembly (1100) that is coupled to a linac (1120) is depicted in FIG. 11. As depicted there, the beam converter assembly (1100) may comprise a beam converter (1102) mounted within a recess of a substrate (1104). An electron beam (1101) traveling within a vacuum cavity (1122) may pass through a linac window (1124) and may be directed at one side of the beam converter (1102). The interaction of the electron beam with the beam converter may generate an X-ray beam (1103) that is emitted from the other side of the beam converter. The substrate (1104) may be made of a conductive material, such as copper. The substrate (1104) may comprise one or more heat removal channels (1106) within the body of the substrate. In some variations, the heat removal channel (1106) may be located adjacent to the beam converter, and a cooling fluid (e.g., gas or liquid) may be circulated through the channel (1106). Heat generated by the incidence of electrons on the beam converter (1102) may be transferred to the conductive substrate (1104), which then transfers the heat to the cooling fluid within the channel (1106). While the systems described herein may comprise the beam converter assembly of FIG. 11, it should be understood that other beam converter assemblies (e.g., with other substrate geometries, heat removal channel configurations and beam converter materials) may be used.

CT System

In some radiation therapy systems, a kV radiation source and corresponding detector may be provided for imaging purposes (e.g., CT imaging). The kV radiation source and detector may be located on the rotating ring of the gantry, but at a different longitudinal location from the MV or therapeutic radiation source such that the fan beam generated by the kV radiation source is in a different plane from the MV radiation source. As with the MV or therapeutic radiation source, alignment of the imaging radiation source (e.g., imaging linac) may also be motorized. Imaging data collected may be used to register the position of the patient relative to the gantry and the therapeutic radiation source. Accurate registration of the patient to the radiotherapy system facilitates the accurate delivery of the radiation treatment. It may be desirable to register the patient quickly and accurately. Images and/or data from the kV radiation source may also help to identify the positions of target volumes and sensitive structures that are to be avoided.

In some variations, a kV system may comprise a kV radiation source, a kV detector, and a series of static and dynamic collimator elements to control the shape of the radiation beam emitted from the kV radiation source. For example, a series of two static collimators may define an aperture profile along two axes (e.g., X-axis, Y-axis) whose geometry may be defined by their relative location to isocenter and the kV detector. Additionally, a kV system may comprise a rotatable collimation mechanism configured to control irradiation of the beam onto the patient and kV detector. The rotatable collimation mechanism may comprise an electrical actuator, a rotatable collimator comprising beam-limiting elements, and a position-sensing circuit. The rotatable mechanism may be configured to rapidly adjust the position of its beam-limiting elements via an electrical actuator and position sensing circuit.

Figure 13A:
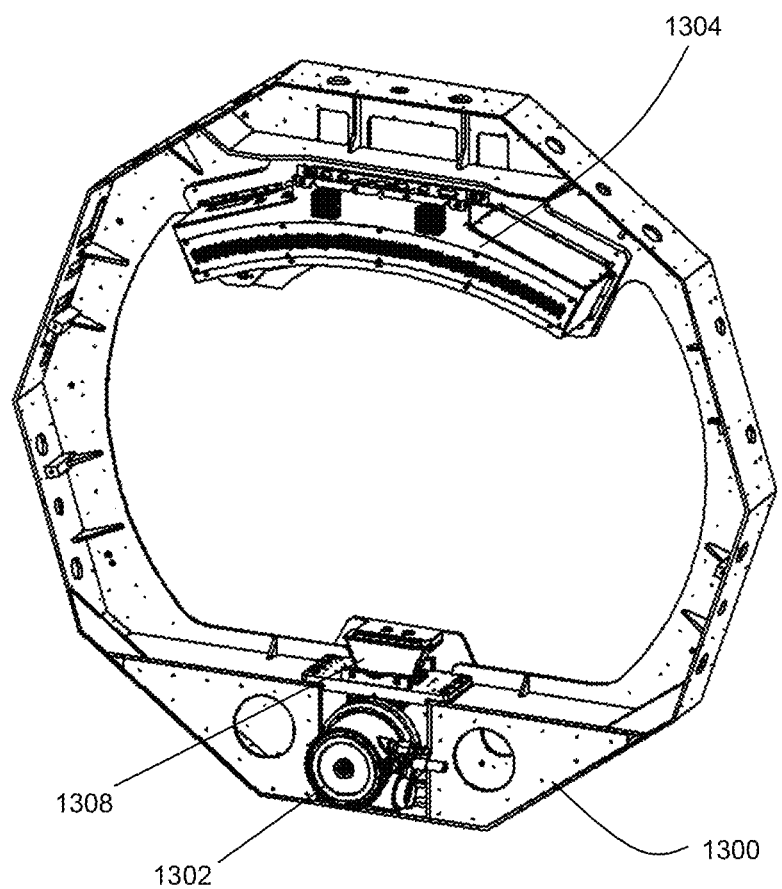
FIG. 13A depicts one variation of a kV CT gantry ring.
Figure 13B:
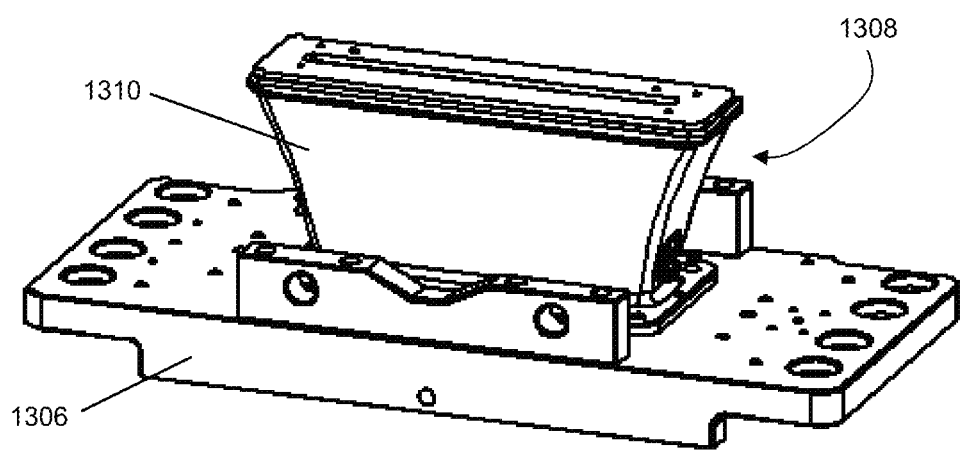
FIG. 13B depicts one variation of a kV radiation source collimator for a kV imaging system.
Figure 13C:
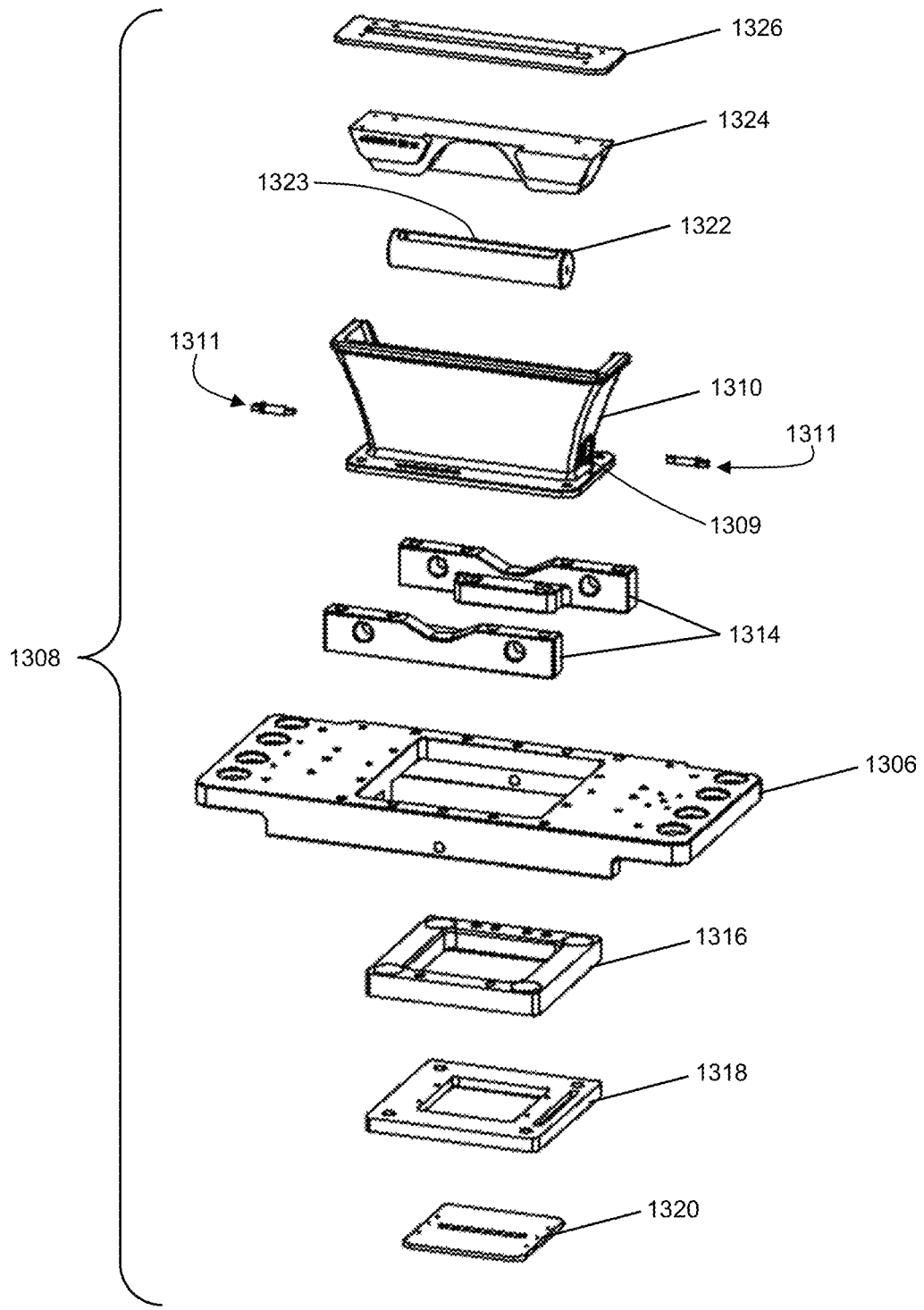
FIG. 13C is a perspective exploded view of the kV radiation source collimator of FIG. 13B.

FIG. 13A depicts one variation of a kV imaging gantry (1300) that may comprise a kV radiation source (1302), kV detector (1304), kV support structure (not depicted) and a collimation assembly (1308). The kV imaging gantry (1300) may be attached to the rotatable ring to which the therapeutic radiation source, MV detector, and PET detectors are attached. The kV imaging gantry may be attached to the rotatable ring using a plurality of bolts and/or weld points. FIG. 13B depicts one variation of a kV radiation source support (1306) and a collimation assembly (1308). The collimation assembly (1308) may comprise a radiation shield (1310). FIG. 13C depicts an exploded view of the collimation assembly (1308), kV radiation source support (1306) and radiation shield (1310) of FIG. 13B. Turning to FIG. 13C, the collimation assembly may comprise a support structure (1306) upon which an X-axis mounting stage (1314) and the radiation shield (1310) are mounted. It may further comprise an alignment plate (1316) and a Y-axis mounting stage (1318) mounted beneath the X-axis mounting stage (1314). An initial beam limiting or shaping device (1320) may be mounted on the Y-axis mounting stage (1318). This may help to maintain the relative positioning between the kV radiation source, kV detector and any additional beam shaping devices.

Figure 14A:
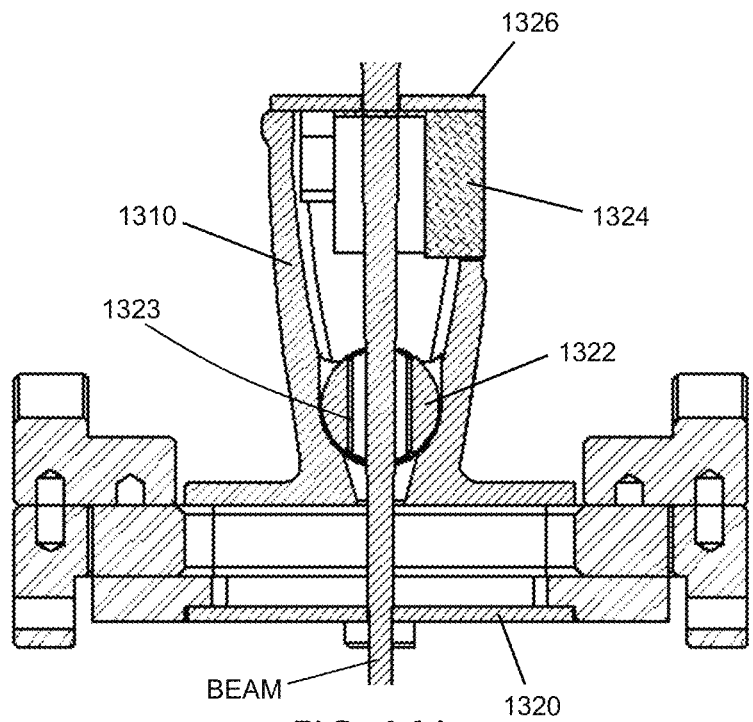
FIG. 14A is a cross-sectional view of a first configuration of a kV radiation source collimator.
Figure 14B:
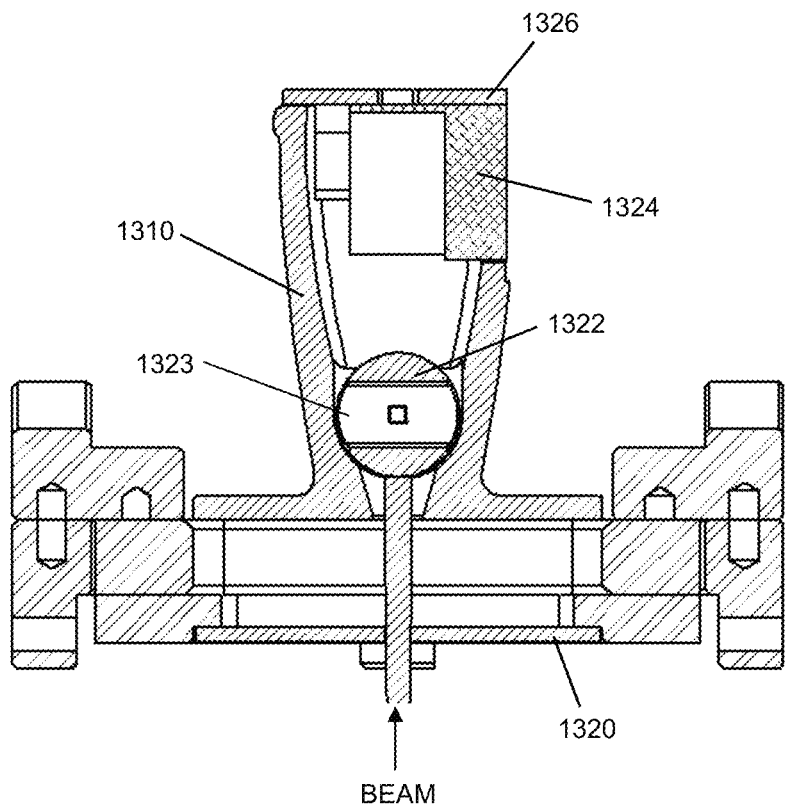
FIG. 14B is a cross-sectional view of a second configuration of the kV radiation source collimator of FIG. 14A.

The radiation shield (1310) may be disposed over the kV radiation source and may have a shape that corresponds to the expanding kV radiation source beam. Wall portions of the shield (e.g., side wall portions) may provide support for a rotatable collimator (1322), beam shaping filter (1324) and final beam limiting or shaping device (1326). For example, there may be two side openings (1309) on the side wall portion of the shield (1310), which may be configured to rotatably retain two axles (1311). The axles (1311) may be cylindrical and may be connected to the two ends of the rotatable collimator (1322), serving as an axis of rotation for the collimator. For example, the rotatable collimator (1322) may comprise a dowel or cylinder made of a radiation-blocking material, such as tungsten or lead. The dowel or cylinder may have a longitudinal axis and a central aperture opening (1323). The central opening (1323) may extend transversely through the cylinder (e.g., perpendicular to its longitudinal axis) and/or may have a length along the longitudinal axis that may correspond with a desired beam width. For example, the central opening may extend through the entire diameter or thickness of the collimator, and may have a length that approximates the length of the collimator. The aperture opening may be configured to shape the beam along two axes (e.g., X-axis and Y-axis), and/or may be configured to shape the beam along one axis (e.g., X-axis). The two axles or shafts (1311) may be connected to either end of the dowel or cylinder such that rotation of the axles (1311) also rotates the rotatable collimator (1322). The rotatable collimator may have two configurations and rotation of the collimator may transition between these two configuration. In the first configuration, which is depicted in FIG. 14A, the aperture (1323) is aligned with a radiation beam from the kV radiation source, and allows the kV radiation beam to pass through. Upon rotation of a certain angle (e.g., about 90 degrees), the collimator may be transitioned to a second configuration, depicted in FIG. 14B. In this configuration, the aperture (1323) is not aligned with the radiation beam and the wall portion of the cylinder or dowel, which is made of a radiation-blocking material, may impede or block the kV radiation beam.

A kV radiation beam collimator may help attain and maintain precise and/or accurate imaging beam performance. In some variations, the alignment between the kV radiation beam and the collimator may be within a predetermined tolerance threshold of about 10 microns or less. The alignment of the kV radiation beam to the collimator may be checked in several circumstances, for example, in the factory, upon delivery of the system to a clinic or customer, and in the event that the kV radiation source or kV detector is serviced or repaired.

II. Methods

Also described here are methods for emission-guided high-energy photon delivery using the systems and devices described above. In some variations, the methods may be used to deliver a radiation dose to a desired region of a patient. Generally, the methods described here comprise registering a patient loaded onto a patient platform and treating the patient using a radiotherapy system. Increasing the efficiency of a patient registration and treatment may help to increase the number of patients that may be treated by a single radiation therapy system over the course of a time period (e.g., a day).

In some variations, a method of processing radiotherapy patients may comprise registering the patient to a patient platform using a registration system in a registration room. The patient may then be moved to a different room having a radiotherapy system where the patient is treated by the radiotherapy system. By performing registration and radiation treatment in separate rooms, a patient may receive a radiation dose while another patient is being registered in a different room. Thus, the preparation of a patient for treatment may occur in parallel with the treatment session of another patient, while maintaining privacy and without compromise to treatment quality. In some examples, the workflow may begin in an administering room where the patient is administered a radioisotope (e.g., a PET tracer). The patient may wait in the administering room until the room having the registration system is vacated.

In some variations, patient registration may optionally comprise applying an external radioactive fiducial to a patient. The external radioactive fiducial may help improve the accuracy and/or precision of patient registration for a number of treatment modalities (e.g., EGRT, SBRT, IMRT). In some examples, the radioactive fiducial may be used to provide an initial coarse registration helpful in reducing patient dose received from subsequent kV imaging. The radioactive fiducial may be inserted into the body and/or combined with other fiducials (e.g., radiopaque tattoo on a patient skin). In other examples, the radioactive fiducial may remain coupled to the patient during radiation treatment and allow detection of patient motion during treatment.

In some variations, a movement speed of one or more of a gantry, collimator, and patient platform may be adaptively adjusted in real-time according to an intensity modulation of radiation beams prescribed in a treatment plan in order to reduce radiation treatment procedure times. For example, the movement speed of a rotating gantry and a patient platform may be reduced for radiation beam delivery to a tumor requiring a higher level of modulation (e.g., a tumor having an irregular shape). In another example, a patient platform speed may be increased when the radiation beam is off and moving between different tumors. In this manner, speed of one or more of the gantry, collimator, and patient platform may be increased while operating the radiotherapy system within mechanical limits and without compromise to treatment objectives. In some variations, the patient platform may be moved to a pre-determined location, stopped at the pre-determined location while therapeutic radiation is applied to the patient, and then moved to another pre-determined location (e.g., step-and-shoot motion). Applying therapeutic radiation in such matter may help mitigate dose delivery imperfections and/or magnetron arcs that are often encountered when radiation is delivered to a continuously moving patient platform.

In some variations, a radiotherapy system may be configured to output a noise cancellation signal to a patient undergoing a procedure in a bore of a gantry to reduce the perceived mechanical noise generated by the system during operation. A reduction in the perceived noise may increase patient comfort and consequently reduce patient movement on a patient platform (e.g., patient shifting), thereby improving patient compliance. In some examples, ear location data of a patient may be used to generate the noise cancellation signal. The radiotherapy system may comprise an audio system having one or more microphones to receive the noise to be cancelled and speakers to output the noise cancellation signal.

Radiation Therapy Workflow

A radiation therapy system is a high-cost expenditure that can treat only a limited number of patients in the course of a day. Bunker time is expensive and it is therefore desirable to reduce the amount of bunker time spent on treatment tasks that do not require the use of the radiation therapy system. For example, IMRT and SBRT procedures typically deliver a radiation dose over a number of fractions. Some IMRT procedures may deliver about 60 Gy to about 80 Gy over about 30 to about 40 fractions (e.g., 2 Gy per fraction). Delivery of each IMRT fraction may take about 15 to about 20 minutes with about 10 of those minutes devoted to patient setup. Some SBRT procedures may deliver about 40 Gy to 80 Gy over about 3 to about 5 fractions. Delivery of each SBRT fraction may take about 40 minutes to about 90 minutes with about 15 minutes to about 40 minutes of patient setup depending upon the number and location of lesions. The differences in patient setup time between IMRT and SBRT may be because generally, an IMRT fraction is delivered for a single lesion while an SBRT fraction may be delivered for one or more lesions. Under these patient workflow constraints, a radiotherapy system may deliver about 30 to about 40 IMRT fractions per day and about 6 to about 10 SBRT fractions per day. The patient workflow processes described in detail below may improve allow a radiotherapy system to deliver up to about 60 IMRT fractions per day and up to about 12 SBRT fractions per day.

Figure 12:
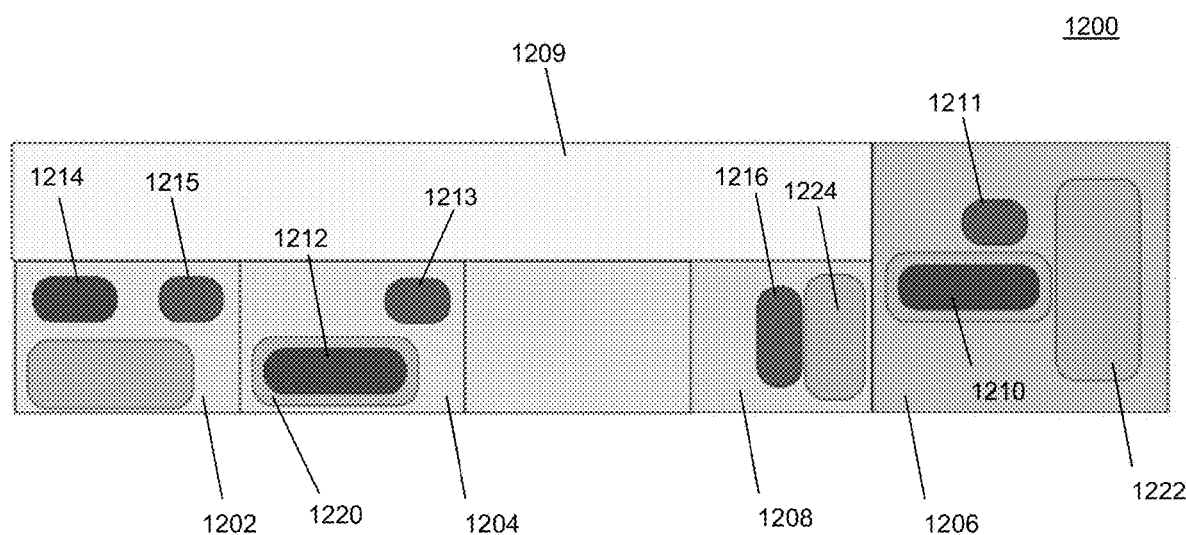
FIG. 12 is an illustrative schematic of a variation of patient workflow for a radiation therapy system.

The radiation therapy system as described herein may treat patients in different rooms in parallel, thereby maintaining privacy and increasing bunker usage efficiency and patient throughput. For example, patient uptake of a radioisotope may be performed in a first room while patient imaging and registration may be performed in a second room. The patient may then be moved into a third room comprising the radiation therapy system to receive radiation therapy treatment. Accordingly, patients do not occupy the third room until ready to receive radiation therapy treatment. Workflow may be improved by performing tasks in parallel, thus allowing three patients in the workflow simultaneously (at different stages of treatment). FIG. 12 is a schematic depiction of patient workflow for a radiation therapy facility (1200) comprising a first room (1202), second room (1204), third room (1206), control room (1208), and hallway (1209) connecting each of the rooms. The first room (1202) may be configured for radioisotope administration and uptake. For example, the first room (202) may be configured to be a quiet, comfortable space for a patient to wait while biological uptake occurs. For example, the uptake for a PET tracer such as FDG may take about 60 minutes. The second room (1204) may comprise a registration system and be configured for patient registration of a patient to a patient platform. For example, the second room (1204) may comprise an imaging system (e.g., kV CT, MR, PET/CT) configured to image and register the patient to the patient platform. Various types of patient platforms may be used, for example, the patient platforms described and depicted in a co-pending U.S. Application entitled "RADIATION THERAPY PATIENT PLATFORM", U.S. patent application Ser. No. 15/814,276, filed on Nov. 15, 2017, which is hereby incorporated by reference in its entirety. The patient registration process may generally take about 10 minutes. The third room (1206) may comprise a radiation therapy system and be configured to treat the patient. Treatment times in the third room (1206) may vary based upon the type of treatment being performed, type of lesion, and number of lesions. For example, radiation dose delivery for a simple IMRT lesion may be performed in about 5 minutes while radiation dose delivery for a complicated, multi-lesion patient may be performed in about 60 minutes. In some variations, a technician (1211, 1213, 1215) (e.g., healthcare professional) may be assigned to a respective patient (1210, 1212, 1214). In some variations, a control room (1208) may comprise an operator console (1224) and an operator (1216) to control patient registration and radiation therapy in the second room (1204) and third room (1206). In other variations, each of the second room (1204) and third room (1206) may comprise an operator.

In some variations of the methods described herein, a radiation therapy patient process may comprise administering a radioisotope to the first patient (1210) in a first room (1202), and moving the first patient (1210) from the first room (1202) into the second room (1204). Once in the second room (1204), the first patient (1210) may be loaded onto a first patient platform. The loaded first patient platform may then be moved into a registration region of the registration system and location data of the first patient's body may be generated using the registration system. For example, diagnostic imaging of the first patient (1210) and first patient platform may be generated and used to register the first patient's body to the first patient platform. Then, the first patient (1210) coupled to the first patient platform may be moved out of the second room (1204) through hallway (1209) and into the third room (1206). The patient should restrict their movement on the first patient platform after registration until treatment is completed.

In some variations, the patient platform may comprise a set of wheels for movement while in other variations, the patient platform may be coupled to a rail system of the facility (1200) connecting the registration system of the second room (1204) to the radiation therapy system of the third room (1206). For example, a rail system may be disposed on the floor and guide the patient platform from the second room (1204) to the third room (1206). The patient platform may be manually moved and/or driven by a motor. The first patient platform having the registered first patient may then be docked to the radiation therapy system. In some variations, a patient platform including a transportable base may be moved from room to room such that the base docks to each system. In other variations, the patient platform may be transferred to a different base in each room. For example, the patient platform may be transported on a first base and then the transferred to a fixed base fixed to the gantry of a radiation therapy system. Docking the first patient platform to the radiation therapy system registers the position of the patient to the radiation therapy system. The patient registration must remain unchanged as the patient is moved from room to room and may be monitored using a sensor system.

The registered first patient platform may then be moved into a treatment region of the radiation therapy system and the first patient may be treated using the radiation therapy system. Each of the above steps may be performed for a second patient and a second patient platform after completing the each step by the first patient. In other words, once the first patient vacates a room, another patient may enter the room to create a continuous pipeline of patients. Likewise, each step of the above steps may be performed for a third patient and a third patient platform after completing the step by the second patient. It should be appreciated that a single radiation source (e.g., accelerator) may be coupled to a plurality of radiation therapy systems (e.g., a fourth room comprising a second radiation therapy system). In some variations, the imaging and treatment may be done in the same room on separate imaging and treatment systems Patient Registration Patient registration to a radiotherapy system is important to the accuracy of dose delivery and constitutes a significant amount of the time in a patient procedure. Intensity modulated radiation therapy (IMRT) procedures commonly utilize external fiducials for the initial registration of the patient. These are often in the form of small tattoos on the skin. These tattoos may be visually aligned to lasers in a treatment room that are aligned to the radiotherapy system. The resulting alignment is generally to within 5 mm of structures inside the body. However, tattoo registration may be manually intensive and time consuming. In some variations, a patient may be registered to both a radiotherapy system and a diagnostic imaging machine using external fiducials. An external fiducial may be, for example, small radioactive point source (about 500 kV) attached to a patient. A plurality of PET detectors in the radiation therapy system may detect the external fiducial and register the patient. In some examples, the external fiducial may be left attached to the patient for the entirety of the procedure, while in other situations, the point source may be attached as needed to the patient and aligned to a permanent or semi-permanent tattoo on the skin.

An external PET fiducial may be useful in patient registration for EGRT, SBRT, and IMRT systems. PET detectors of an EGRT system may be used to register patients to the system quickly and with reasonable accuracy for patients that have or have not received a PET tracer injection by using an external PET fiducial. For example, a PET detector system may provide coarse patient registration while an integrated kV imaging system may provide fine patient registration. The coarse PET registration may improve patient registration by reducing subsequent kV imaging coverage, dose, and time.

In variations where a patient body structure is located using an external radioactive fiducial as described in detail herein, a radioactive fiducial may be coupled to an external portion of the patient. The external portion may be one or more of skin, an orifice of the patient, a sternum, and a hip. A diagnostic image may be generated by a PET/CT diagnostic system using the radioactive point sources coupled to the skin. The external fiducials may be left on for the entirety of the procedures and/or used to locate a permanent or semi-permanent tattoo. The radioactive fiducial may be disposed in a patch and placed over the sternum and/or hips of the patient. In some variations, the radioactive fiducial may comprise a small, rigid, high-energy photon transparent well having an adhesive backing to couple to the patient. Accordingly, the radioactive fiducial corresponds to the patient body structure. In some examples, the patient may be marked at a first skin location corresponding to the patient body structure (e.g., by permanent/semi-permanent tattoo on the sternum and hips), and the radioactive fiducial coupled to the patient at the first location. The radioactive fiducial and the patient coupled to the patient platform may then be located using, for example, PET/CT diagnostic imaging. The patient body structure may be registered to the patient platform using the location of the radioactive fiducial. The fiducial may remain applied to the patient during radiation therapy treatment. In some examples, the external radioactive fiducial may register the patient to better than 5 mm. For an IMRT procedure where the patient does not receive a PET tracer injection, this registration may be adequate. For an EGRT procedure where the patient receives a PET tracer injection, further registration of the tumor volumes and sensitive structures can be done using the internal PET signals to increase registration accuracy. The radioactive fiducial (e.g., PET fiducial) may be any source that produces an approximately 500 kV event localized to a point under PET imaging (e.g., a 500 kilovolt point source). For example, the radioactive fiducial may comprise Na22, PET tracers, and other kV sources.

In some variations, the patient may be treated using a radiotherapy beam with the radioactive fiducial coupled to the patient. It should be appreciated that the radioactive fiducial may be located in parallel with treatment steps being performed, as this may allow determination of movement of the patient body structure during treatment. In other variations, the diagnostic image may be a kV CT image and the external fiducial coupled to the patient may be a small, dense metal bead configured to show contrast on kV images. In some variations, a metal fiducial may be coupled to an external portion of the patient. Similar to the radioactive fiducial, the metal fiducial may correspond to the patient body structure on which it is placed. The metal fiducial may be located by imaging. The metal fiducial may then by removed prior to radiotherapy treatment or remain attached during radiation therapy treatment.

The radioactive fiducial may comprise an orifice block configured for insertion in the orifice. In some examples, the orifice block may comprise a bite block to three-dimensionally locate a patient's bony structures. For example, the bite block may comprise a head fixation device that further allows for registration of a patient body structure in three dimensions. Additionally or alternatively, the radioactive fiducial may be coupled to patient clothing configured to be worn on the patient.

In some variations, the external radioactive fiducial may be coupled with an optically dense housing or well that shows contrast in kV images and may be imaged using a PET detector system integrated with a kV imaging system. The optically dense housing may be coupled to the patient using, for example, an adhesive. For a kV CT diagnostic scan, the housing may be coupled to the patient without a radioactive source. The dense material under kV CT imaging may be easily resolved and registered. For PET/CT imaging, the dense housing may comprise the radioactive source such that the dense material may be resolved by the kV CT and the radioactive source resolved by the PET. The PET sensing may provide gross alignment to within around 5 mm so that the kV imaging coverage may be reduced. A reduction in kV imaging reduces the registration time and X-ray dose to the patient.

In variations where a patient body structure is located using an internal radioactive fiducial as described in detail herein, an internal region of interest of a patient may be located, and a radioactive fiducial may be implanted into the region of interest. The radioactive source may be implanted internally using a surgical procedure or a large needle. The radioactive source may be a point source. In some variations, the radioactive source may have a resolution below that of the PET system (e.g., a point source having a diameter of about 4 mm). The radioactive fiducial and the patient coupled to a patient platform may be located using, for example, kV imaging. The region of interest may be registered to the patient platform using the location of the radioactive fiducial. In some variations, the implanted radioactive fiducial may comprise one or more of a hydrogel and a tracer. The implanted fiducial may allow for accurate tracking of a region of interest and/or sensitive structures so that dose delivery margins may be reduced. This may spare healthy tissue from an unnecessary dose which may allow for treatment of more lesions and/or at higher doses, and/or more maintenance sessions.

Adjustable Platform and Gantry Speeds

Helical tomotherapy is a type of intensity-modulated radiation therapy (IMRT). An IMRT system may comprise a radiation beam source that rotates about a longitudinal axis of a gantry, a collimator comprising a plurality of leaves shaping a radiation beam, and a patient platform that moves relative to the gantry. A patient may receive a helical or spiral radiation dose during simultaneous operation of the rotatable gantry, collimator, and patient platform (e.g., gantry spinning around its longitudinal axis and patient platform moving longitudinally). In helical radiation therapy, intensity modulation may be achieved by varying an intensity of the radiation beam at each gantry angle and each patient platform position while the gantry and the patient platform simultaneously move. In order for the intensity modulated dose to be delivered very accurately during helical tomotherapy, collimator leaves (e.g., multi-leaf collimator (MLC)) must open at precise times corresponding to a precise gantry angle position and patient platform position. Helical radiation beam intensity modulation therefore depends on the accuracy of the timing of the MLC transitions (between open and closed positions), gantry and patient platform speeds.

When the gantry rotates relatively slow, such as in the range from 1 RPM to 10 RPM and when there is a relatively large angular difference between gantry firing positions, such as 7 degrees, there is generally sufficient time for the leaves to close or open in between the gantry positions such that radiation therapy treatment may follow a treatment plan with a high level of fidelity and precision. Some conventional tomotherapy systems may comprise 51 gantry firing positions (7 degree spacing between each firing position) and comprise gantry rotation speeds during patient treatment range between about 1 RPM and about 5 RPM. However, when gantry speeds are much higher than about 10 RPM, and especially for EGRT systems that may reach gantry speeds of about 60 RPM with 100 firing angles (3.6 degree spacing between each firing position), the MLC transitions must be much faster to provide an accurate dose. As gantry speeds increase and angular differences between gantry firing positions are reduced, MLC transition times may reach their mechanical and electronic limits, thus placing a limit on the level of achievable intensity modulation for a given gantry rotation speed and/or patient platform speed. Radiation therapy treatment quality may be compromised if the MLC, gantry, and patient platform are operated at speeds near the system's mechanical limits, especially if a treatment plan requires a high level of modulation. For example, an increase in the gantry speed while keeping the angular separations of the firing positions fixed may require either re-calculating the treatment plan by potentially sacrificing the dose prescription constraints on the planning treatment volumes (PTV) and/or organs at risk (OAR) volumes.

The radiation therapy systems described herein may provide variable and real-time gantry and/or patient platform speeds to increase or decrease modulation during radiation beam delivery. The systems may comprise a rotatable gantry, a patient platform disposed in a patient region of the gantry, a collimator mounted to the gantry and comprising a plurality of leaves, and a radiation source coupled to the collimator. The patient platform may move relative to the gantry (e.g., longitudinally through a bore of the gantry) and the leaves of the collimator may open and close from a plurality of gantry angles. For example, when less modulation (e.g., lower rate of MLC transitions) is required (per the treatment plan), the gantry and/or patient platform may speed up, and when more modulation is required, the gantry and/or patient platform may slow down. In another example, when the radiation beam is off, such as when moving between different tumors at different locations in the body, the speed of the gantry and/or patient platform may be varied (e.g., increasing the speed of the patient platform and reducing the speed of the gantry). Alternatively or additionally, the platform speed may be adjusted based on data acquired by the PET detectors during a treatment session. In this manner, treatment objectives may be achieved while reducing treatment times.

A tumor comprising an irregular shape may require more modulation to deliver the dose with the proper shape. For example, the prostate axial view has a horseshoe shape, which is concave around the rectum. As the shape of the tumor becomes more irregular, increased modulation may be desirable. Therefore, a speed of the gantry rotation and/or patient platform may be reduced when the collimated fan beam irradiates a target with a high degree of irregularity. In some variations, data acquired by the PET detectors may be used to adjust the platform speed. For example, areas with elevated levels of PET emissions may be irradiated for longer periods of time than areas with lower levels of PET emissions. Accordingly, the platform speed may be reduced to increase the dwell time of regions with elevated levels of PET emissions in the fan beam, and the platform speed may be increased to decrease the dwell time of regions with lower levels of PET emissions in the fan beam.

In some variations, a method of operating a radiotherapy system as described herein to reduce treatment times may comprise receiving a treatment plan of a patient comprising a set of open leaves and corresponding gantry angles. The beamlet firing positions given by the open leaves and gantry angles of the treatment plan corresponds to an intensity modulation. A radiation beam may be output from the collimator using the radiation source and the treatment plan while a speed of one or more of the patient platform and gantry may be varied using the treatment plan. Thus, intensity modulation of any level may be preserved as prescribed by the treatment plan by adaptively adjusting one or more of the gantry speed and patient platform speed.

In some variations, a speed of the collimator may be prioritized over the speed of the patient platform and gantry in response to the level of modulation required by the system to the treatment plan. For example, a speed of the collimator may be maintained and/or set at as desired while the speed of one or more of the patient platform and gantry is varied. When the MLC transitions times are unable to keep up with a particular combination of the gantry speed, and/or number of gantry firing positions and/or patient platform speed, the gantry speed and/or couch speed may be slowed down with a dose rate is kept constant. Thus, when there is little modulation required, the gantry and/or patient platform are made to go faster, but when more modulation is required, the gantry and/or patient platform are made to go slower in order to achieve the desired level of intensity modulation. In some examples, the gantry speed may be held constant while the patient platform speed varies. Conversely, the patient platform speed may be held constant while the gantry speed varies.

A radiation therapy procedure for some patients may include treating multiple, distinct tumors. In addition to varying the speed of gantry rotation and/or the patient platform in response to the modulation levels of a tumor, the speed of the patient platform may be varied between tumors. For example, the patient platform speed may be increased in absence of radiation beam emission. As there is no dose to be delivered between tumors, the patient platform speed may be set to a first speed (e.g., set to a maximum speed) between tumors to reduce an overall treatment time. In some variations, the first speed of the patient platform and/or gantry may be any desirable speed when there is no beam emission, but as the patient platform reaches a margin of the tumor, the patient platform and/or gantry may accelerate/decelerate to reach the operational speed prescribed by the treatment plan. For example, a margin (e.g., 0.5 cm, 1 cm, 1.5 cm, 2 cm) may be provided around the tumor to allow the patient platform to decelerate for higher modulation at the tumor.

Dose Rate

There are situations in radiotherapy delivery where it is desirable to vary or gate the dose rate. In some variations, the linac may utilize an injected electron beam pulse from the injector gun and an RF pulse from the RF source (e.g., magnetron). The injector beam pulse and RF pulse may usually be aligned (i.e., the electron beam pulse and the RF pulse are in-phase). Either or both of the pulses can be misaligned (i.e., phase-adjusted to be out-of-phase) or shortened to gate or vary the dose rate. For systems that use magnetrons for the RF source, it may be desirable to not change the RF pulse. In these systems, the RF pulse from the magnetron may be consistent, but the radiation beam pulse rate may be varied by changing the injector (e.g., electron gun) pulse rate.

Figure 10:
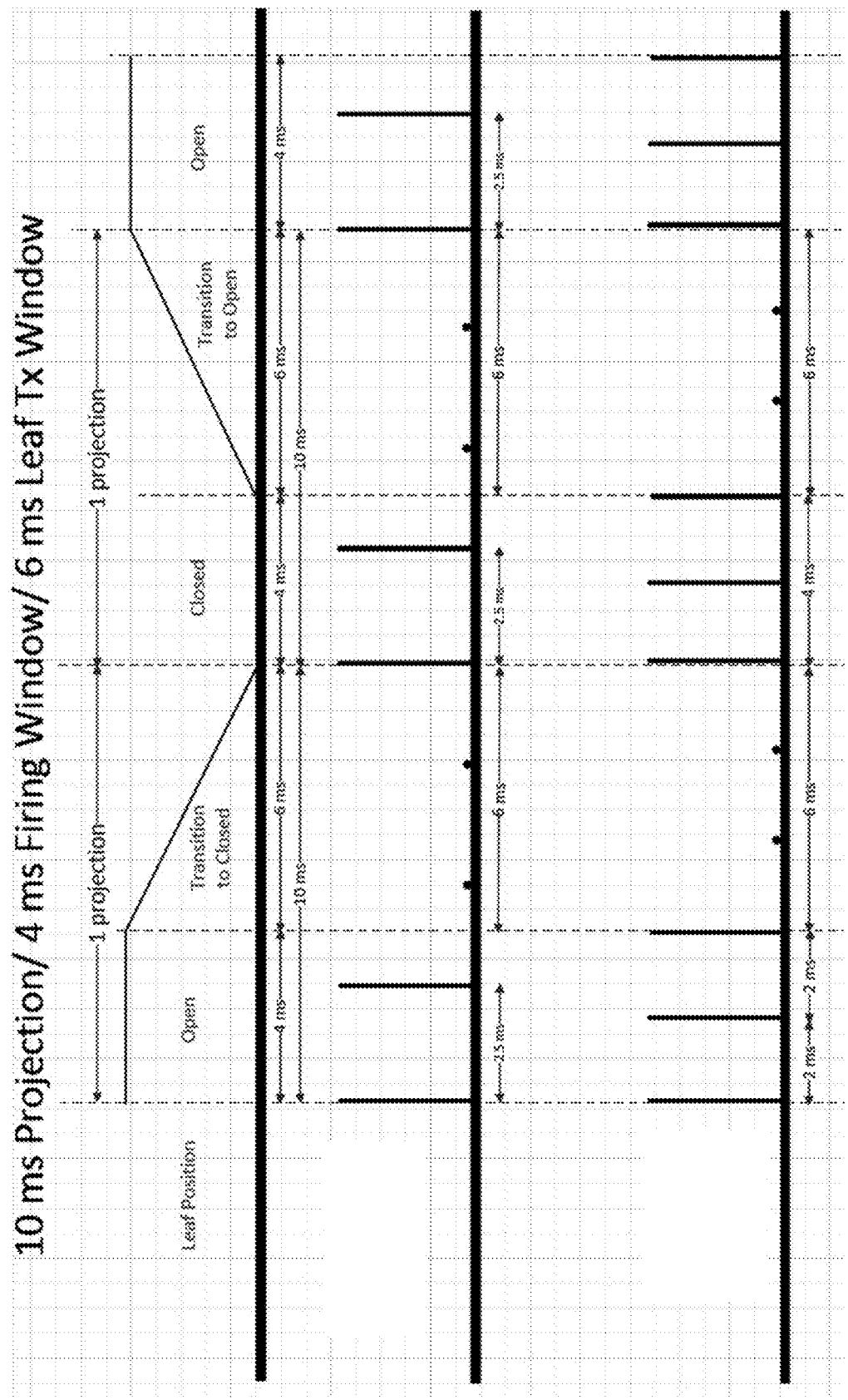
FIG. 10 is an illustrative depiction of a variation of a collimator timing diagram.

A radiotherapy system comprising a binary multi-leaf collimator may output multiple linac pulses per projection. One example is depicted in FIG. 10. Here, a projection is a section of rotation that includes the binary MLC leaf transition time and a window to deliver radiation. This firing algorithm may be suited to a ring gantry that is rotating fast enough to respond to normal patient movements such as breathing. For example, a ring gantry rotating at 60 RPM, divided into 100 projections leaves 10 milliseconds per projection. A leaf transition time of 5 milliseconds then leaves 5 milliseconds per projection for radiation delivery. A linac pulse rate of 300 Hz (3.3 milliseconds apart) would only allow for two pulses in the 5 millisecond window. Whereas a 400 Hz pulse rate (2.5 milliseconds apart) would allow for three pulses in the 5 millisecond windows (one at the beginning of the window, one in the center of the window, and one at the end of the window. For a radiotherapy system where the linac fires at a constant rate as the ring gantry system rotates, the leaf openings and transitions may be timed to maximize the number of linac triggers that are delivered by grouping projections where no leaves are required to transition. In these methods, the number of linac triggers that are not delivered because there are leaves transitioning are minimized. In variations where there are more than one pulses per firing window, the dose rate may be modulated by varying the number of pulses fired per firing window. For example, at 400 Hz it is possible to fire up to three pulses in a 5 millisecond window. This is in contrast to typical linac systems, which operate at a consistent repetition rate, where the time delay between every pulse is the same. Varying the time delay between pulses may allow the radiation generation system to compress the same number of pulses into a firing window while staying below the thermal-average threshold of some of the radiation generating components such as the RF source, linac, RF windows, and target converter.

Noise Cancellation

In some variations, a radiation therapy system may comprise an audio system useful for reducing auditory discomfort from mechanical noise generated by the system that may reduce patient comfort and increase patient anxiety. In some variations, a method of noise cancellation for a radiotherapy system may comprise receiving ear location data of a patient disposed in a patient treatment area of a radiotherapy system. For example, the ear location data may be determined using patient registration data (e.g., from PET imaging, kV CT imaging) or the patient may be positioned at a predetermined location such that the ear location may be known. The noise generated from the radiotherapy system may be received using a microphone. A noise cancellation signal may be generated using the ear location data and the received noise. The cancellation signal may then be output from a speaker. The ambient noise mixed with the cancellation signal at the patient's ears will cancel each other out (e.g., destructive interference) to reduce the volume of the perceivable noise to the patient.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

The invention claimed is:

1. A radiation therapy system comprising:
a circular gantry having a radial axis; and
a therapeutic radiation source mounted on the gantry and comprising a linear accelerator (linac) and a magnetron for accelerating electrons in the linac,
wherein the magnetron comprises: a ring anode having a central cavity; a cathode located in the central cavity; and a cathode support substantially aligned along the radial axis of the gantry that couples the cathode to the ring anode.

2. The system of claim 1, further comprising one or more positron emission tomography (PET) detectors mounted on the circular gantry.

3. The system of claim 1, wherein the circular gantry comprises a bore, wherein the bore comprises a first portion and a second portion, wherein a second portion diameter is greater than a first portion diameter.

4. The system of claim 1, wherein the circular gantry comprises a bore and an image projector configured to illuminate at least a region of the bore.

5. The system of claim 4, wherein the illumination comprises one or more of an image and video.

6. The device of claim 4, further comprising an audio device configured to output sound within the bore.

7. The device of claim 4, further comprising an airflow device configured to direct airflow through the bore.

8. The device of claim 4, further comprising an optical eye tracker configured to detect one or more of an eye position and eye gaze of a patient in the bore, and a processor configured to change the illumination using the eye position and the eye gaze.

9. The system of claim 1, wherein the gantry comprises a bore and a flexible display disposed along a surface of the bore.

10. The system of claim 9, wherein the flexible display is an organic light-emitting diode (OLED) display.

11. The system of claim 1, wherein the ring anode further comprises a plurality of cavities surrounding the central cavity.

12. The system of claim 1, wherein the circular gantry comprises a rotatable ring that generates a centripetal force during rotation, and wherein the cathode support is aligned along a direction of the centripetal force.

13. The system of claim 12, wherein the radial axis extends toward a center of the ring.

* * * * *